US009441239B2

(12) United States Patent
Waterhouse et al.

(10) Patent No.: US 9,441,239 B2
(45) Date of Patent: *Sep. 13, 2016

(54) METHODS AND MEANS FOR OBTAINING MODIFIED PHENOTYPES

(75) Inventors: Peter Michael Waterhouse, Canberra (AU); Ming-Bo Wang, Kaleen (AU); Michael Wayne Graham, Jindalee (AU)

(73) Assignee: Commonwealth Scientific & Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/364,183

(22) Filed: Mar. 1, 2006

(65) Prior Publication Data

US 2006/0178335 A1  Aug. 10, 2006

Related U.S. Application Data

(63) Continuation of application No. 10/755,328, filed on Jan. 13, 2004, now abandoned, which is a continuation of application No. 09/287,632, filed on Apr. 7, 1999, now Pat. No. 8,598,332.

(60) Provisional application No. 60/198,254, filed on Aug. 3, 1998, provisional application No. 60/198,240, filed on Apr. 8, 1998.

(51) Int. Cl.
*C12N 15/11* (2006.01)
*C12N 15/82* (2006.01)
*A61K 48/00* (2006.01)

(52) U.S. Cl.
CPC ....... *C12N 15/8283* (2013.01); *C12N 15/8218* (2013.01); *C12N 15/8247* (2013.01); *C12N 15/8282* (2013.01); *A01K 2217/05* (2013.01); *A61K 48/00* (2013.01)

(58) Field of Classification Search
CPC . C12N 15/113; C12N 15/63; C12N 2310/14
See application file for complete search history.

(56) References Cited

U.S. PATENT DOCUMENTS

| | | | |
|---|---|---|---|
| 5,034,323 A | 7/1991 | Jorgensen et al. | |
| 5,190,931 A | 3/1993 | Inouye | |
| 5,231,020 A | 7/1993 | Jorgensen et al. | |
| 5,283,184 A | 2/1994 | Jorgensen et al. | |
| 5,349,126 A * | 9/1994 | Chappell et al. | 800/265 |
| 5,365,015 A | 11/1994 | Grierson et al. | |
| 5,530,192 A | 6/1996 | Murase et al. | |
| 5,597,718 A | 1/1997 | John et al. | |
| 5,624,803 A * | 4/1997 | Noonberg et al. | 435/6 |
| 5,801,154 A | 9/1998 | Baracchini et al. | |
| 5,850,026 A | 12/1998 | DeBonte et al. | |
| 5,859,347 A | 1/1999 | Brown et al. | |
| 5,939,600 A | 8/1999 | Goldbach et al. | |
| 5,952,546 A | 9/1999 | Bedbrook et al. | |
| 6,150,585 A | 11/2000 | Goldbach et al. | |
| 6,350,575 B1 | 2/2002 | Lusky et al. | |
| 6,423,885 B1 | 7/2002 | Waterhouse et al. | |
| 6,451,603 B1 | 9/2002 | Atkins et al. | |
| 6,506,559 B1 | 1/2003 | Fire et al. | |
| 6,573,099 B2 | 6/2003 | Graham | |
| 7,138,565 B2 | 11/2006 | Waterhouse et al. | |
| 7,538,095 B2 * | 5/2009 | Fire | A61K 31/7105 435/320.1 |
| 7,622,633 B2 * | 11/2009 | Fire | A61K 31/7105 435/468 |
| 8,598,332 B1 * | 12/2013 | Waterhouse | C12N 15/8218 435/455 |
| 2003/0074684 A1 | 4/2003 | Graham | |
| 2003/0159161 A1 | 8/2003 | Graham | |
| 2004/0180439 A1 | 9/2004 | Graham | |
| 2004/0237145 A1 | 11/2004 | Graham | |
| 2004/0266005 A1 | 12/2004 | Graham | |
| 2005/0250208 A1 | 11/2005 | Graham | |
| 2005/0251877 A1 | 11/2005 | Waterhouse et al. | |
| 2006/0014715 A1 | 1/2006 | Graham | |
| 2007/0056057 A1 | 3/2007 | Waterhouse et al. | |
| 2008/0044906 A1 | 2/2008 | Waterhouse et al. | |

FOREIGN PATENT DOCUMENTS

| | | |
|---|---|---|
| AU | 20891/97 | 10/1997 |
| EP | 0223399 | 5/1987 |
| EP | 0240208 | 10/1987 |
| EP | 240208 | 10/1987 |
| EP | 0467349 | 1/1992 |
| EP | 467349 | 1/1992 |

(Continued)

OTHER PUBLICATIONS

Acosta-Garcia and Vielle-Calzada, "A Classical Arabinogalactan Protein is Essential for the Initiation of Female Gametogenesis in Arabidopsis", The Plant Cell, 16:2614-28, 2004 (Am. Soc. of Plant Biologists, USA).

Agami, R., "RNAi and related mechanisms and their potential use for therapy", Current Opinion in Chemical Biology, 2002, vol. 6, pp. 829-834.

Anderson, W.F., "Human gene therapy", Nature, 1998, vol. 392, No. 6679 Suppl., pp. 25-30.

Barry et al., "Methylation Induced Premeiotically in Ascobolus: Coextension with DNA Repeat Lengths and Effect on Transcript Elongation", Proc. Natl Acad Sci., 1993, vol. 90, pp. 4557-4561.

Baulcomb, "Mechanisms of Pathogen-Derived Resistance to Viruses in Transgenic Plants", Plant Cell, 1996, vol. 8, pp. 1833-1844.

(Continued)

*Primary Examiner* — Brian Whiteman
(74) *Attorney, Agent, or Firm* — Buchanan Ingersoll & Rooney PC

(57) ABSTRACT

Methods and means are provided for reducing the phenotypic expression of a nucleic acid of interest in eucaryotic cells, particularly in plant cells, by introducing chimeric genes encoding sense and antisense RNA molecules directed towards the target nucleic acid, which are capable of forming a double stranded RNA region by base-pairing between the regions with sense and antisense nucleotide sequence or by introducing the RNA molecules themselves. Preferably, the RNA molecules comprises simultaneously both sense and antisense nucleotide sequence.

66 Claims, 2 Drawing Sheets

(56) References Cited

FOREIGN PATENT DOCUMENTS

| | | |
|---|---|---|
| EP | 0522880 | 1/1993 |
| EP | 0647715 | 4/1995 |
| EP | 0779364 | 6/1997 |
| EP | 0426195 B1 | 10/2001 |
| EP | 0458367 B1 | 10/2001 |
| WO | 89/10396 | 11/1989 |
| WO | 90/14090 | 11/1990 |
| WO | 91/02069 | 2/1991 |
| WO | 91/16426 | 10/1991 |
| WO | 91/16440 | 10/1991 |
| WO | 92/04456 | 3/1992 |
| WO | 92/11375 | 7/1992 |
| WO | 92/11376 | 7/1992 |
| WO | 92/13070 | 8/1992 |
| WO | 92/17596 | 10/1992 |
| WO | 92/18625 | 10/1992 |
| WO | 92/21757 | 12/1992 |
| WO | 93/05159 | 3/1993 |
| WO | 93/10251 | 5/1993 |
| WO | 93/23551 | 11/1993 |
| WO | 94/01550 A1 | 1/1994 |
| WO | 94/09143 | 4/1994 |
| WO | 94/17194 | 8/1994 |
| WO | 94/18337 | 8/1994 |
| WO | 94/29465 | 12/1994 |
| WO | 95/07993 | 3/1995 |
| WO | 95/09920 | 4/1995 |
| WO | 97/01952 | 1/1997 |
| WO | 97/13865 | 4/1997 |
| WO | 97/16559 | 5/1997 |
| WO | 98/05770 | 2/1998 |
| WO | 98/53083 | 11/1998 |
| WO | 99/15682 | 4/1999 |
| WO | 99/29879 | 6/1999 |
| WO | 99/32619 | 7/1999 |
| WO | 99/49029 | 9/1999 |
| WO | 99/61631 | 12/1999 |
| WO | 99/61632 | 12/1999 |

OTHER PUBLICATIONS

Braun and Hemenway, "Expression of Amino-Terminal Portions or Full-Length Viral Replicase Gene in Transgenic Plants Confers Resistance to Potato Virus X Infection", Plant Cell, 1992, vol. 4, pp. 735-744.
Brederode et al., "Replicase-Mediated Resistance to Alfalfa Mosaic Virus", Virology, 1995, vol. 207, pp. 467-474.
J.A. Brussian et al., "An Arabidopsis Mutant with a Reduced Level of cab140 RNA is a Result of Cosuppression", The Plant Cell, vol. 5, Jun. 1993, p. 667-677, American Society of Plant Physiologists, Rockville, MD, USA.
Byzova et al., "Transforming petals into sepaloid organs in Araidopsis and oilseed rape: implementation of the hairpin RNA mediated gene silencing technology in an organ-specific manner", Planta, 218:379-87, 2004, (Springer-Verlag).
Cameron et al., "Inhibition of gene expression by a short sense fragment", Nucleic Acids Research, 1991, vol. 19, No. 3, pp. 469-475.
Caplen., "N.J. A new approach to the inhibition of gene expression", Trends in Biotechnology, 2002, vol. 20, No. 2, pp. 49-51.
Carr et al., "Resistance to Tobacco Mosaic Virus Induced by the 54-kDa Gene Sequence Requires Expression of the 54-kDa Protein", Mol. Plant-Microb. Interact., vol. 5, pp. 397-404.
Chen et al., "Temporal and spatial control of gene silencing in transgenic plants by inducible expression of double stranded RNA", The Plant Journal, 36:731-40, 2003, (Blackwell Publishing, USA).
de Carvalho Niebel et al., "Post-Transcriptional Cosuppression of -1,3-Glucanase Genes does not Affect Accumulation of Transgene Nuclear mRNA", Plant Cell, 1995, vol. 7, pp. 347-358.
E.C. Dale et al., "Intra- and Intermolecular Site-Specific Recombination in Plant Cells Mediated by Bacteriophage P1 Recombinase", Gene, vol. 91, pp. 79-85, 1990, Elsevier Science Publishers B.V. (Biomedical Division) NY USA.

D.R. Dorer et al, "Expansions of Transgene Repeats Cause Heterochromatin Formation and Gene Silencing in *Drosophila*," Cell, 77(7):993-1002 (1994).
D.R. Dorer et al., Transgene Repeat Arrays Interact With Distant Heterochromatin and Cause Silencing in *cis* and *trans*, Genetics, vol. 147, pp. 1181-1190 (Nov. 1997), Genetics Society of America.
W.G. Dougherty et al., "Transgenes and Gene Suppression: telling us something new?", Current Opinion in Cell Biology, 1995, vol. 7, p. 399-405; Current Biology, London, UK.
English et al., Suppression of Virus Accumulation in Transgenic Plants Exhibiting Silencing of Nuclear Genes Plant Cell, 1996, vol. 8, pp. 179-188.
M. Faske et al., "Transgenic Tobacco Plants Expressing Pea Chloroplast *Nmdh* cDNA in Sense and Antisense Orientation", Plant Physiol., 1997, vol. 115, p. 705-715, Am. Soc. of Plant Physiologists, Lancaster, PA.
A. Fire et al, "Production of Antisense RNA Leads to Effective and Specific Inhibition of Gene Expression in *C. elegans* Muscle", Development, vol. 113, pp. 503-514 (191, The Company of Biologists Limited, Great Britain.
Fire et al., Potent and Specific Genetic Interference by Double-Stranded RNA in *Caenorhabditis elegans*, Nature, 1998, vol. 391:806-811.
Goodwin et al., "Genetic and Biochemical Dissection of Transgenic RNA-Mediated Virus Resistance", Plant Cell, 1996, vol. 8, pp. 95-105.
M.W. Graham et al., "Co-suppression, Anti-sense and Synthetic Viral Resistance: a Common Mechanism!", Symposium 4-3, Abstract for talk given by Michael Graham at the Lorne Genome Conference, Victoria, Australia in Feb. 1996.
Guo et al., "A chemical regulated inducible RNAi system in plants", The Plant Journal, 34:383-92, 2003, (Blackwell Publishing, USA).
Hobbs et al., "The Effect of T-DNA Copy Number, Position and Methylation on Reporter Gene Expression in Tobacco Transformants", Plant Mol. Biol. 1990, vol. 15, pp. 851-864.
Ingelbrecht et al., "Posttranscriptional Silencing of Reporter Transgenes in Tobacco Corrects with DNA Methylation", 1994, vol. 91, pp. 10502-10506.
Jorgensen et al., "Do Unintened Antisense Transcripts Contribute to Sense Co-Suppression in Plants", Trends in Genetics, 1999, vol. 15, No. 1, pp. 11-12.
R. Jorgensen et al., "T-DNA is Organized Predominantly in Inverted Repeat Structures in Plants Transformed with *Agrobacterium tumefaciens* C58 Derivatives," Mol. Gen. Genet. 207:471-477 (1987).
M. Katsuki et al, "Conversion of Normal Behavior to Shiverer by Myelin Basic Protein Antisense cDNA in Transgenic Mice", Science, vol. 241, Jul. 29, 1988, p. 593-595, Am. Assn for the Advancement of Science, Washington, DC.
Kawcheck et al., "Sense and Antisense RNA-Mediated Resistance to Potato Leafroll Virus in Russet Burbank Potato Plants", 1991, vol. 4, pp. 247-253.
C.A. Kelton et al., "The cloning of the human follicle stimulating hormone receptor and its expression in COS-7, CHO, and Y-1 cells", Molecular and Cell. Endocrin., 1992, vol. 89, No. 1-2, pp. 141-151.
Y.H. Kook et al., "The Effect of Antisense Inhibition of Urokinase Receptor in Human Squamous Cell Carcinoma on Malignancy", The EMBO Journal, vol. 13, No. 17, p. 3938-3991, 1994, Oxford University Press, Oxford, England.
A. Kuipers, et al., "Factors Affecting the Inhibition by Antisense RNA of Granule-Bound Starch Synthase Gene Expression in Potato," Mol. Gen. Genet. 246:745-755 (1995).
M.H. Kumagai et al, "Cytoplasmic Inhibition of Carotenoid Biosynthesis With Virus-Derived RNA", Genetics, Proc. Natl. Acad. Sci. USA, vol. 92, pp. 1679-1683, Feb. 1995, National Academy of Sciences, Washington, D.C.
Lee et al., "Making a better RNAi vector for *Drosophila*: use of intron spacers", Methods, 30:322-9, 2003, (Elsevier Science).
J.A. Lindbo et al., "Virus-Mediated Reprogramming of Gene Expression in Plants", Current Opinion in Plant Biology, vol. 4, p. 181-185, 2001, Elsevier Science Ltd., Amsterdam, Holland.

(56) References Cited

OTHER PUBLICATIONS

Lindbo and Dougherty, "Pathogen-Derived Resistance to a Potyvirus: Immune and Resistant Phenotypes in Transgenic Tobacco Expressing Altered Forms of a Potyvirus Cost Protein Nucleotide Sequence", Mol. Plant Micr. Int., 1992a, vol. 5, pp. 144-153.
Lindbo and Dougherty, "Untranslatable Transcripts of the Tobacco Etch Virus Coat Protein Gene Sequence can Interfere with Tobacco Etch Virus Replication in Transgenic Plants and Protoplasts", Virology, 1992b, vol. 189, pp. 725-733.
Lindbo et al., "Induction of a Highly Specific Antiviral State in Transgenic Plants: Implications for Regulation of Gene Expression and Virus Resistance", Plant Cell, 1993, vol. 5, pp. 1749-1759.
Li et al., "The Cotton ACTIN1 Gene is Functionally Expressed in Fibers and Participates in Fiber Elongation", The Plant Cell, 17:859-75, 2005, (Am. Soc. of Plant Biologists, USA).
J. Lisziewicz et al, "Inhibition of Human Immunodeficiency Virus Type 1 Replication by Regulated Expression of a Polymeric Tat Activation Response RNA Decoy as a Strategy for Gene Therapy in AIDS", Medical Sciences, vol. 90, pp. 8000-8004, Sep. 1993, Proc. Natl. Acad. Sci. USA, Washington D.C.
Longstaff et al., "Extreme Resistance to Potato Virus X Infection in Plants Expression a Modified Component of the Putative Viral Replicase" EMBO J., 1993, vol. 12, pp. 379-386.
Marathe, "CIS-Repeat Induced Gene Silencing in Tobaco", Ph.D. Thesis, University of South Carolina, 1997.
M. Matzke et al., "How and Why Do Plants Inactivate Homologous (Trans)genes?", Plant Physiol. (2995) vol. 107, pp. 679-685, American Society of Plant Physiologists, Lancaster, PA.
M. Matzke et al, "Epigenetic Silencing of Plant Transgenes as a Consequence of Diverse Cellular Defence Responses" CMLS, Cell. Mol. Life Sci. vol. 54 (1998) pp. 94-103, Birkhauser, Basil, Switzerland, Boston.
Metzlaff and O'Dell, "RNA-Mediated RNA Degradation and Chalcone Synthase a Silencing in Petunia", Cell, 1997, vol. 88, pp. 845-854.
P. Meyer, "Understanding and Controlling Transgene Expression", Tibtech, Sep. 1995, vol. 13, p. 332-337, Elsevier Science, Amsterdam, Holland.
P. Meyer, "Homology-Dependent Gene Silencing in Plants", Annu. Rev. Plant Physiol. Plant Mol. Biol., 1996, vol. 47, p. 23-48, Annual Reviews, Inc., Palo Alto, California.
M. Montgomery et al., "Double-stranded RNA as a Mediatory in Sequence-Specific Genetic Silencing and Co-suppression", TIG Jul. 1998, vol. 14, No. 7, pp. 255-258, Elsevier Science Ltd., Oxford, England.
M.K. Montgomery et al., "RNA as a Target of Double-stranded RNA-mediated Genetic Interference in Caenorhabditis elegans" Proc. Natl. Acad. Sci. USA, vol. 95, Dec. 1998, p. 15502-15507, the National Academy of Sciences, Washington, D.C.
M.C. Moroni et al, "EGF-R Antisense RNA Blocks Expression of the Epidermal Growth Factor Receptor and Suppresses the Transforming Phenotype of a Human Carcinoma Cell Line", The Journal of Biological Chemistry, vol. 267, No. 5, issue of Feb. 5, 1992, p. 2714-2722, American Society for Biochemistry and Molecular Biology, Baltimore, MD.
Mueller et al., "Homology-Dependent Resistance: Transgenic Virus Resistance in Plants Related to Homology-Dependent Gene Silencing", Plant J. 1995, vol. 7, pp. 1001-1003.
C. Napoli et al., "Introduction of a Chimeric Chalcone Synthase Gene into Petunia Results in Reversible Co-Suppression of Homologous Genes in trans", the Plant Cell, vol. 2, Apr. 1990, p. 279-289, American Society of Plant Physiologists, Rockville, MD.
Nellen and Lichtenstein, "What Makesan mRNA Anti-sensitive", Trends in Biochemical Sciences, 1993, vol. 18, No. 11, pp. 419-423.
O'Brien, "Molecular analysis of the stylar-expressed Solanum chacoense small asparagine-rich protein family related to the HT modifier of gametophytic self-incompatibility in Nicotiana", The Plant Journal, 22:985-96, 2002 (Blackwell Publishing).

Pang et al., "Post-transcriptional Transgene Silencing and Consequent Tospovirus Resistance in Transgenic Lettuce are Affected by Transgene Dosage and Plant Development", Plant J. 1996, vol. 9, pp. 899-909.
Powell-Abel et al., "Delay of Disease Development ion Transgenic Plants that Express the Tobacco Mosaic Virus Coat Protein Gene", Science, 1986, vol. 232, pp. 738-743.
Powell et al., "Protection Against Tobacco Mosaic Virus Infection in Transgenic Plants Requires Accumulation of Coat Protein Rather than Coat Protein RNA Sequences", Virology, 1990, vol. 175, pp. 124-130.
C. Proud, "PKR: a New Name and New Roles", TIBS Jun. 20, 1995, pp. 241-246, Elsevier Science, Oxford, England.
Que et al., "Distinct Patterns of Pigment Suppression are Produced by Allelic Sense and Antisense Chalcone Synthase Transgenes in Petunia Flowers", The Plant Journal, 1998, vol. 13, pp. 401-409.
F. Ratcliff et al., "A Similarity Between Viral Defense and Gene Silencing in Plants", Science, vol. 276, Jun. 6, 1997, pp. 1558-1560, Amer. Assn. for the Advancement of Science, Washington, D.C.
K. Redenbaugh et al., "Safety Assessment of Genetically Engineered Fruits and Vegetables—A Case Study of the FlavrSavr™ Tomato," CRC Press (1992).
Samuel and Ellis, "Double Jeopardy: Both Overexpression and Suppression of a Redox-Activated Plant Mitogen-Activated Protein Kinase Render Tobacco Plants Ozone Sensitive", The Plant Cell, 14:2059-69, 2002 (Am. Soc. of Plant Biologists, USA).
J.C. Sanford et al., "The Concept of Parasite-Derived Resistance—Deriving Resistance Genes from the Parasite's own Genome", J. Theor. Biol., 1985, vol. 13, p. 395-405, Academic Press Inc., London, England.
K.W. Savin et al., "Antisense ACC Oxidase RNA Delays Carnation Petal Senescence", HortScience, vol. 30(5), Aug. 1995, p. 970-972, HortScience is a publication of the American Society for Horticulture Science.
Scherr et al., "Gene Silencing Mediated by Small Interfereing RNA's Mammalian Cells", Current Medicinal Chemistry, 2003, vol. 10, pp. 245-256.
Schiebel et al., "RNA-directed RNA Polymerase from Tomato Leaves", The Journal of Biological Chemistry, vol. 268, 1993a, pp. 11851-11857.
W. Schiebel et al., "RNA-directed RNA Polymerase from Tomato Leaves", The Journal of Biological Chemistry, vol. 268, No. 16, Jun. 5, 1993, p. 11858-11867, American Society for Biochemistry and Molecular Biology, Inc., Baltimore, MD.
R.E. Sheehy et al., "Reduction of Polygalacturonase Activity in Tomato Fruit by Antisense RNA", Proc Natl Acad. Sci, USA, vol. 85, Dec. 1988, p. 8805-8809, the National Academy of Sciences, Washington, D.C.
T. Sijen et al., "RNA-Mediated Virus Resistance: Role of Repeated Transgenes and Delineation of Targeted Regions," The Plant Cell, 8:2277-2294 (1996).
Smith, "Total Silencing by intron-spliced hairpin RNAs", Nature, 407:319-20, 2000, (Macmillan Magazines).
Smith, "Transgenic Plant Virus Resistance Mediated by Untranslatable Sense RNAs: Expression, Regulation, and Fate of Nonessential RNAs", Plant Cell, 1994, vol. 6, pp. 1441-1453.
Stam et al., "The Silence of Genes in Transgenic Plants", Ann. Botany., 1997, vol. 79, pp. 3-12.
B.A. Sullenger et al, "Analysis of trans-Acting Response Decoy RNA-Mediated Inhibition of Human Immunodeficiency Virus Type 1 Transactivation", Journal of Virology, Dec. 1991, vol. 65, No. 12, p. 6811-6816, American Society for Microbiology, Washington D.C.
S. Swaney et al., "RNA-Mediated Resistance with Nonstructural Genes from the Tobacco Etch Virus Genome", MPMI vol. 8, No. 6, 1995, p. 1005-1011, The American Phytopathological Society, St. Paul, Minnesota.
L.Q. Sun et al., "Resistance to Human Immunodeficiency Virus Type 1 Infection Conferred by Transduction of Human Peripheral Blood Lymphocytes With Ribozyme, Antisense, or Polymeric Trans-Activation Response Element Constructs", Proc. Natl. Acad. Sci., USA vol. 92, pp. 7272-7276, Aug. 1995, Medical Sciences, Washington, D.C.

(56) References Cited

OTHER PUBLICATIONS

H. Tabara et al., "RNAi in *C. elegans*: Soaking in the Genome Sequence", Science, vol. 282, Oct. 16, 1998, pp. 430-431, Amer. Assn. for the Advancement of Science, Washington, D.C.
L. Timmons et al, "Specific Interference by Ingested dsRNA", Nature, vol. 395, Oct. 29, 1998, Nature Publishing Group, London, England.
R. Van Blokland et al., "Post-Transcriptional Suppression of Chalcone Synthase Genes in *Petunia Hybrida* and the Accumulation of Unspliced pre-mRNAS, Mechanisms and Applications of Gene Silencing," Grierson et al, (Eds), Nottingham University Press (1996).
R. Van Blokland et al, "Transgene-mediated Suppression of Chalcone Synthase Expression in *Petunia hybrida* Results from an increase in RNA Turnover", The Plant Journal, 1994, vol. 6, No. 6, p. 861-877, Blackwell Sciences, Oxford, England.
A.R. van der Krol et al., "Flavonoid Genes in Petunia: Addition of a Limited Number of Gene Copies May Lead to a Suppression of Gene Expression", The Plant Cell, vol. 2, Apr. 1990, p. 291-299, American Society of Plant Physiologists, Rockville, MD.
Verma et al., "Gene therapy-promises problems and prosects", Nature, 1997, vol. 389, pp. 239-424.
Wagner and Sun., "Double-Stranded RNA Poses Puzzle", Nature, 1998, vol. 391, pp. 744-745.
M. Wassenegger et al, "A Model for RNA-Mediated Gene Silencing in Higher Plants", Plant Molecular Biology, vol. 37, pp. 349-362, 1998, Kluwer Academic Publishers, Belgium.
Waterhouse et al., "Virus Resistance and Gene Silencing in Plants can be Induced by Simultaneous Expression of Sense and Antisense RNA", Proc. Natl. Acad. Sci. USA, 1998, vol. 95, pp. 13959-13964.
Wesley et al., "Construct design for efficient, effective and high-throughput gene silencing in plants", The Plant Journal, 27:581-90, 2001, (Blackwell Publishing).
M. Xu et al., "Immunoglobulin kappa gene expression after stable integration. II. Role of the intronic MAR and enhancer in transgenic mice", J. Biol. Chem., 1989, vol. 264, No. 35, pp. 21190-21195.
U.S. Appl. No. 09/287,632 by Waterhouse et al., filed Apr. 7, 1999.
Non-Final Rejection dated May 11, 2009 in U.S. Appl. No. 09/287,632 by Waterhouse et al., filed Apr. 7, 1999.
Search information including classification, databases and other search related notes dated May 11, 2009 in U.S. Appl. No. 09/287,632 by Waterhouse et al., filed Apr. 7, 1999.
Amendment/Req. Reconsideration—After Non-Final Reject dated Mar. 19, 2009 in U.S. Appl. No. 09/287,632 by Waterhouse et al., filed Apr. 7, 1999.
Rule 130, 131 or 132 Affidavits dated Mar. 19, 2009 in U.S. Appl. No. 09/287,632 by Waterhouse et al., filed Apr. 7, 1999.
Non-Final Rejection dated Sep. 19, 2008 in U.S. Appl. No. 09/287,632 by Waterhouse et al., filed Apr. 7, 1999.
List of references dated Sep. 19, 2008 in U.S. Appl. No. 09/287,632 by Waterhouse et al., filed Apr. 7, 1999.
Search information including classification, databases and other search related notes dated Sep. 19, 2008 in U.S. Appl. No. 09/287,632 by Waterhouse et al., filed Apr. 7, 1999.
Miscellaneous Incoming Letter dated May 7, 2008 in U.S. Appl. No. 09/287,632 by Waterhouse et al., filed Apr. 7, 1999.
Rule 130, 131 or 132 Affidavits dated May 7, 2008 in U.S. Appl. No. 09/287,632 by Waterhouse et al., filed Apr. 7, 1999.
Amendment/Req. Reconsideration—After Non-Final Reject dated May 1, 2008 in U.S. Appl. No. 09/287,632 by Waterhouse et al., filed Apr. 7, 1999.
Rule 130, 131 or 132 Affidavits dated May 1, 2008 in U.S. Appl. No. 09/287,632 by Waterhouse et al., filed Apr. 7, 1999.
Examiner Interview Summary Record dated Nov. 30, 2007 in U.S. Appl. No. 09/287,632 by Waterhouse et al., filed Apr. 7, 1999.
Rule 130, 131 or 132 Affidavits dated Nov. 1, 2007 in U.S. Appl. No. 09/287,632 by Waterhouse et al., filed Apr. 7, 1999.
Non-Final Rejection dated Nov. 1, 2007 in U.S. Appl. No. 09/287,632 by Waterhouse et al., filed Apr. 7, 1999.
List of references dated Nov. 1, 2007 in U.S. Appl. No. 09/287,632 by Waterhouse et al., filed Apr. 7, 1999.
Search information including classification, databases and other search related notes dated Nov. 1, 2007 in U.S. Appl. No. 09/287,632 by Waterhouse et al., filed Apr. 7, 1999.
Examiner's search strategy and results dated Oct. 27, 2007 in U.S. Appl. No. 09/287,632 by Waterhouse et al., filed Apr. 7, 1999.
Examiner's search strategy and results dated Oct. 23, 2007 in U.S. Appl. No. 09/287,632 by Waterhouse et al., filed Apr. 7, 1999.
Amendment/Req. Reconsideration—After Non-Final Reject dated Aug. 8, 2007 in U.S. Appl. No. 09/287,632 by Waterhouse et al., filed Apr. 7, 1999.
Rule 130, 131 or 132 Affidavits dated Aug. 8, 2007 in U.S. Appl. No. 09/287,632 by Waterhouse et al., filed Apr. 7, 1999.
Non-Final Rejection dated Feb. 8, 2007 in U.S. Appl. No. 09/287,632 by Waterhouse et al., filed Apr. 7, 1999.
List of References dated Feb. 8, 2007 in U.S. Appl. No. 09/287,632 by Waterhouse et al., filed Apr. 7, 1999.
Search information including classification, databases and other search related notes dated Feb. 8, 2007 in U.S. Appl. No. 09/287,632 by Waterhouse et al., filed Apr. 7, 1999.
Amendment Submitted/Entered with Filing of CPA/RCE dated Nov. 22, 2006 in U.S. Appl. No. 09/287,632 by Waterhouse et al., filed Apr. 7, 1999.
Information Disclosure Statement (IDS) Filed (SB/08) dated Nov. 22, 2006 in U.S. Appl. No. 09/287,632 by Waterhouse et al., filed Apr. 7, 1999.
Final Rejection dated Jun. 22, 2006 in U.S. Appl. No. 09/287,632 by Waterhouse et al., filed Apr. 7, 1999.
Search information including classification, databases and other search related notes dated Jun. 22, 2006 in U.S. Appl. No. 09/287,632 by Waterhouse et al., filed Apr. 7, 1999.
Examiner's search strategy and results dated Jun. 20, 2006 in U.S. Appl. No. 09/287,632 by Waterhouse et al., filed Apr. 7, 1999.
Examiner's Interview Summary Record dated Jun. 2, 2006 in U.S. Appl. No. 09/287,632 by Waterhouse et al., filed Apr. 7, 1999.
Amendment/Req. Reconsideration—After Non-Final Reject dated May 10, 2006 in U.S. Appl. No. 09/287,632 by Waterhouse et al., filed Apr. 7, 1999.
Non-Final Rejection dated Nov. 10, 2005 in U.S. Appl. No. 09/287,632 by Waterhouse et al., filed Apr. 7, 1999.
List of References dated Nov. 10, 2005 in U.S. Appl. No. 09/287,632 by Waterhouse et al., filed Apr. 7, 1999.
Search information including classification, databases and other search related notes dated Nov. 10, 2005 in U.S. Appl. No. 09/287,632 by Waterhouse et al., filed Apr. 7, 1999.
Examiner's search strategy and results dated Nov. 10, 2005 in U.S. Appl. No. 09/287,632 by Waterhouse et al., filed Apr. 7, 1999.
Amendment/Req. Reconsideration—After Non-Final Reject dated Sep. 12, 2005 in U.S. Appl. No. 09/287,632 by Waterhouse et al., filed Apr. 7, 1999.
Information Disclosure Statement (IDS) dated Jun. 2, 2005 in U.S. Appl. No. 09/287,632 by Waterhouse et al., filed Apr. 7, 1999.
Non-Final Rejection dated Mar. 11, 2005 in U.S. Appl. No. 09/287,632 by Waterhouse et al., filed Apr. 7, 1999.
List of References dated Mar. 11, 2005 in U.S. Appl. No. 09/287,632 by Waterhouse et al., filed Apr. 7, 1999.
Search information including classification, databases and other search related notes dated Mar. 11, 2005 in U.S. Appl. No. 09/287,632 by Waterhouse et al., filed Apr. 7, 1999.
Examiner's search strategy and results dated Mar. 6, 2005 in U.S. Appl. No. 09/287,632 by Waterhouse et al., filed Apr. 7, 1999.
Examiner's search strategy and results dated Feb. 24, 2005 in U.S. Appl. No. 09/287,632 by Waterhouse et al., filed Apr. 7, 1999.
Response to Election / Restriction Filed dated Dec. 3, 2004 in U.S. Appl. No. 09/287,632 by Waterhouse et al., filed Apr. 7, 1999.
Requirement for Restriction/Election dated Nov. 3, 2004 in U.S. Appl. No. 09/287,632 by Waterhouse et al., filed Apr. 7, 1999.
Examiner Interview Summary Record dated Jul. 29, 2004 in U.S. Appl. No. 09/287,632 by Waterhouse et al., filed Apr. 7, 1999.
Information Disclosure Statement (IDS) dated Jun. 3, 2004 in U.S. Appl. No. 09/287,632 by Waterhouse et al., filed Apr. 7, 1999.

(56) References Cited

OTHER PUBLICATIONS

Information Disclosure Statement (IDS) dated May 28, 2004 in U.S. Appl. No. 09/287,632 by Waterhouse et al., filed Apr. 7, 1999.
Miscellaneous Action with SSP dated Mar. 25, 2004 in U.S. Appl. No. 09/287,632 by Waterhouse et al., filed Apr. 7, 1999.
Information Disclosure Statement (IDS) dated Mar. 4, 2004 in U.S. Appl. No. 09/287,632 by Waterhouse et al., filed Apr. 7, 1999.
Information Disclosure Statement (IDS) dated Jan. 29, 2004 in U.S. Appl. No. 09/287,632 by Waterhouse et al., filed Apr. 7, 1999.
Information Disclosure Statement (IDS) dated Jul. 7, 2003 in U.S. Appl. No. 09/287,632 by Waterhouse et al., filed Apr. 7, 1999.
Amendment/Req. Reconsideration—After Non-Final Reject dated Jul. 7, 2003 in U.S. Appl. No. 09/287,632 by Waterhouse et al., filed Apr. 7, 1999.
Information Disclosure Statement (IDS) dated Apr. 16, 2003 in U.S. Appl. No. 09/287,632 by Waterhouse et al., filed Apr. 7, 1999.
Non-Final Rejection dated Apr. 9, 2003 in U.S. Appl. No. 09/287,632 by Waterhouse et al., filed Apr. 7, 1999.
List of references dated Apr. 9, 2003 in U.S. Appl. No. 09/287,632 by Waterhouse et al., filed Apr. 7, 1999.
Information Disclosure Statement (IDS) dated Mar. 11, 2003 in U.S. Appl. No. 09/287,632 by Waterhouse et al., filed Apr. 7, 1999.
Amendment/Req. Reconsideration—After Non-Final Reject dated Jan. 16, 2003 in U.S. Appl. No. 09/287,632 by Waterhouse et al., filed Apr. 7, 1999.
Examiner Interview Summary Record dated Sep. 5, 2002 in U.S. Appl. No. 09/287,632 by Waterhouse et al., filed Apr. 7, 1999.
Non-Final Rejection dated Jul. 16, 2002 in U.S. Appl. No. 09/287,632 by Waterhouse et al., filed Apr. 7, 1999.
List of References dated Jul. 16, 2002 in U.S. Appl. No. 09/287,632 by Waterhouse et al., filed Apr. 7, 1999.
Information Disclosure Statement (IDS) dated Apr. 23, 2002 in U.S. Appl. No. 09/287,632 by Waterhouse et al., filed Apr. 7, 1999.
List of References dated Apr. 23, 2002 in U.S. Appl. No. 09/287,632 by Waterhouse et al., filed Apr. 7, 1999.
Amendment/Req. Reconsideration—After Non-Final Reject dated Apr. 22, 2002 in U.S. Appl. No. 09/287,632 by Waterhouse et al., filed Apr. 7, 1999.
Amendment/Req. Reconsideration—After Non-Final Reject dated Apr. 2, 2002 in U.S. Appl. No. 09/287,632 by Waterhouse et al., filed Apr. 7, 1999.
Advisory Action dated Apr. 2, 2002 in U.S. Appl. No. 09/287,632 by Waterhouse et al., filed Apr. 7, 1999.
Final Rejection dated Nov. 2, 2001 in U.S. Appl. No. 09/287,632 by Waterhouse et al., filed Apr. 7, 1999.
Amendment/Req. Reconsideration—After Non-Final Reject dated Aug. 24, 2001 in U.S. Appl. No. 09/287,632 by Waterhouse et al., filed Apr. 7, 1999.
Amendment/Req. Reconsideration—After Non-Final Reject dated Jun. 11, 2001 in U.S. Appl. No. 09/287,632 by Waterhouse et al., filed Apr. 7, 1999.
Information Disclosure Statement (IDS) dated Mar. 5, 2001 in U.S. Appl. No. 09/287,632 by Waterhouse et al., filed Apr. 7, 1999.
List of References dated Mar. 5, 2001 in U.S. Appl. No. 09/287,632 by Waterhouse et al., filed Apr. 7, 1999.
Amendment/Req. Reconsideration—After Non-Final Reject dated Mar. 5, 2001 in U.S. Appl. No. 09/287,632 by Waterhouse et al., filed Apr. 7, 1999.
Non-Final Rejection dated Oct. 3, 2000 in U.S. Appl. No. 09/287,632 by Waterhouse et al., filed Apr. 7, 1999.
List of references dated Oct. 3, 2000 in U.S. Appl. No. 09/287,632 by Waterhouse et al., filed Apr. 7, 1999.
Examiner's search strategy and results dated Sep. 24, 2000 in U.S. Appl. No. 09/287,632 by Waterhouse et al., filed Apr. 7, 1999.
Response to Election / Restriction Filed dated Aug. 21, 2000 in U.S. Appl. No. 09/287,632 by Waterhouse et al., filed Apr. 7, 1999.
Requirement for Restriction/Election dated Jul. 21, 2000 in U.S. Appl. No. 09/287,632 by Waterhouse et al., filed Apr. 7, 1999.
Information Disclosure Statement (IDS) dated Jul. 13, 2000 in U.S. Appl. No. 09/287,632 by Waterhouse et al., filed Apr. 7, 1999.
Miscellaneous Incoming Letter dated Jul. 13, 2000 in U.S. Appl. No. 09/287,632 by Waterhouse et al., filed Apr. 7, 1999.
Information Disclosure Statement (IDS) dated Jul. 6, 2000 in U.S. Appl. No. 09/287,632 by Waterhouse et al., filed Apr. 7, 1999.
Information Disclosure Statement (IDS) dated Dec. 23, 1999 in U.S. Appl. No. 09/287,632 by Waterhouse et al., filed Apr. 7, 1999.
Preliminary Amendment dated Jun. 28, 1999 in U.S. Appl. No. 09/287,632 by Waterhouse et al., filed Apr. 7, 1999.
Information Disclosure Statement (IDS) dated Apr. 7, 1999 in U.S. Appl. No. 09/287,632 by Waterhouse et al., filed Apr. 7, 1999.
U.S. Appl. No. 10/755,328, filed Jan. 13, 2004 by Waterhouse et al.
Abandonment dated Apr. 19, 2006 in U.S. Appl. No. 10/755,328 by Waterhouse et al., filed Jan. 13, 2004.
Non-Final Rejection dated Sep. 1, 2005 in U.S. Appl. No. 10/755,328 by Waterhouse et al., filed Jan. 13, 2004.
List of References dated Sep. 1, 2005 in U.S. Appl. No. 10/755,328 by Waterhouse et al., filed Jan. 13, 2004.
Search information including classification, databases and other search related notes dated Sep. 1, 2005 in U.S. Appl. No. 10/755,328 by Waterhouse et al., filed Jan. 13, 2004.
Examiner's search strategy and results dated Jun. 30, 2005 in U.S. Appl. No. 10/755,328 by Waterhouse et al., filed Jan. 13, 2004.
Information Disclosure Statement (IDS) dated Jun. 7, 2004 in U.S. Appl. No. 10/755,328 by Waterhouse et al., filed Jan. 13, 2004.
Information Disclosure Statement (IDS) dated Jun. 1, 2004 in U.S. Appl. No. 10/755,328 by Waterhouse et al., filed Jan. 13, 2004.
Preliminary Amendment dated Jan. 13, 2004 in U.S. Appl. No. 10/755,328 by Waterhouse et al., filed Jan. 13, 2004.
U.S. Appl. No. 11/607,062, filed Dec. 1, 2006 by Waterhouse et al.
Non-Final Rejection dated May 12, 2009 in U.S. Appl. No. 11/607,062 by Waterhouse et al., filed Dec. 1, 2006.
List of references dated May 12, 2009 in U.S. Appl. No. 11/607,062 by Waterhouse et al., filed Dec. 1, 2006.
Search information including classification, databases and other search related notes dated May 12, 2009 in U.S. Appl. No. 11/607,062 by Waterhouse et al., filed Dec. 1, 2006.
Examiner's search strategy and results dated May 12, 2009 in U.S. Appl. No. 11/607,062 by Waterhouse et al., filed Dec. 1, 2006.
Response to Election / Restrictiondated Jan. 30, 2009 in U.S. Appl. No. 11/607,062 by Waterhouse et al., filed Dec. 1, 2006.
Information Disclosure Statement (IDS) dated Mar. 14, 2007 in U.S. Appl. No. 11/607,062 by Waterhouse et al., filed Dec. 1, 2006.
Preliminary Amendment dated Dec. 1, 2006 in U.S. Appl. No. 11/607,062 by Waterhouse et al., filed Dec. 1, 2006.
U.S. Appl. No. 11/841,737, filed Aug. 20, 2007 by Waterhouse et al.
Requirement for Restriction/Election dated May 4, 2009 in U.S. Appl. No. 11/841,737 by Waterhouse et al. filed Aug. 20, 2007.
Preliminary Amendment dated Jan. 16, 2008 in U.S. Appl. No. 11/841,737 by Waterhouse et al. filed Aug. 20, 2007.
U.S. Appl. No. 09/373,720, filed Aug. 13, 1999 by Waterhouse et al.
Office Action dated Jan. 19, 2001 in U.S. Appl. No. 09/373,720 by Waterhouse et al. filed Aug. 13, 1999.
Response dated May 18, 2001 in U.S. Appl. No. 09/373,720 by Waterhouse et al. filed Aug. 13, 1999.
Office Action dated Aug. 17, 2001 in U.S. Appl. No. 09/373,720 by Waterhouse et al. filed Aug. 13, 1999.
Response dated Feb. 19, 2002 in U.S. Appl. No. 09/373,720 by Waterhouse et al. filed Aug. 13, 1999.
Examiner Interview Summary dated Feb. 6, 2002 in U.S. Appl. No. 09/373,720 by Waterhouse et al., filed Aug. 13, 1999.
U.S. Appl. No. 0/152,808, filed May 23, 2002 by Waterhouse et al.
Notice of Allowance dated Jul. 11, 2006 in U.S. Appl. No. 10/152,808 by Waterhouse et al., filed May 23, 2002.
Search information including classification, databases and other search related notes dated Jul. 11, 2006 in U.S. Appl. No. 10/152,808 by Waterhouse et al., filed May 23, 2002.
Examiner's search strategy and results dated Jun. 13, 2006 in U.S. Appl. No. 10/152,808 by Waterhouse et al., filed May 23, 2002.
Amendment After Final dated Apr. 7, 2006 in U.S. Appl. No. 10/152,808 by Waterhouse et al., filed May 23, 2002.
Final Rejection dated Oct. 7, 2005 in U.S. Appl. No. 10/152,808 by Waterhouse et al., filed May 23, 2002.

(56) References Cited

OTHER PUBLICATIONS

Search information including classification, databases and other search related notes dated Oct. 7, 2005 in U.S. Appl. No. 10/152,808 by Waterhouse et al., filed May 23, 2002.
Examiner's search strategy and results dated Sep. 22, 2005 in U.S. Appl. No. 10/152,808 by Waterhouse et al., filed May 23, 2002.
Amendment/Req. Reconsideration—After Non-Final Reject dated Jul. 13, 2005 in U.S. Appl. No. 10/152,808 by Waterhouse et al., filed May 23, 2002.
Terminal Disclaimer dated Jul. 13, 2005 in U.S. Appl. No. 10/152,808 by Waterhouse et al., filed May 23, 2002.
Non-Final Rejection dated Jan. 13, 2005 in U.S. Appl. No. 10/152,808 by Waterhouse et al., filed May 23, 2002.
List of References dated Jan. 13, 2005 in U.S. Appl. No. 10/152,808 by Waterhouse et al., filed May 23, 2002.
Search information including classification, databases and other search related notes dated Jan. 13, 2005 in U.S. Appl. No. 10/152,808 by Waterhouse et al., filed May 23, 2002.
Examiner's search strategy and results dated Jan. 4, 2005 in U.S. Appl. No. 10/152,808 by Waterhouse et al., filed May 23, 2002.
Response to Election / Restriction dated Oct. 22, 2004 in U.S. Appl. No. 10/152,808 by Waterhouse et al., filed May 23, 2002.
Requirement for Restriction/Election dated Sep. 22, 2004 in U.S. Appl. No. 10/152,808 by Waterhouse et al., filed May 23, 2002.
Information Disclosure Statement dated Jun. 7, 2004 in U.S. Appl. No. 10/152,808 by Waterhouse et al., filed May 23, 2002.
Information Disclosure Statement dated May 28, 2004 in U.S. Appl. No. 10/152,808 by Waterhouse et al., filed May 23, 2002.
Preliminary Amendment dated May 23, 2002 in U.S. Appl. No. 10/152,808 by Waterhouse et al., filed May 23, 2002.
U.S. Appl. No. 11/593,056, filed Nov. 6, 2006 by Waterhouse et al.
Amendment/Req. Reconsideration—After Non-Final Reject dated Mar. 12, 2009 in U.S. Appl. No. 11/593,056, filed Nov. 6, 2006 by Waterhouse et al.
Terminal Disclaimer Filed dated Mar. 12, 2009 in U.S. Appl. No. 11/593,056, filed Nov. 6, 2006 by Waterhouse et al.
Non-Final Rejection dated Sep. 12, 2008 in U.S. Appl. No. 11/593,056, filed Nov. 6, 2006 by Waterhouse et al.
List of references dated Sep. 12, 2008 in U.S. Appl. No. 11/593,056, filed Nov. 6, 2006 by Waterhouse et al.
Search information including classification, databases and other search related notes dated Sep. 12, 2008 in U.S. Appl. No. 11/593,056, filed Nov. 6, 2006 by Waterhouse et al.
Amendment/Req. Reconsideration—After Non-Final Reject dated Jun. 12, 2008 in U.S. Appl. No. 11/593,056, filed Nov. 6, 2006 by Waterhouse et al.
Non-Final Rejection dated Dec. 12, 2007 in U.S. Appl. No. 11/593,056, filed Nov. 6, 2006 by Waterhouse et al.
List of References dated Dec. 12, 2007 in U.S. Appl. No. 11/593,056, filed Nov. 6, 2006 by Waterhouse et al.
Search information including classification, databases and other search related notes dated Dec. 12, 2007 in U.S. Appl. No. 11/593,056, filed Nov. 6, 2006 by Waterhouse et al.
Response to Election / Restriction dated Sep. 21, 2007 in U.S. Appl. No. 11/593,056, filed Nov. 6, 2006 by Waterhouse et al.
Requirement for Restriction/Election dated Jul. 24, 2007 in U.S. Appl. No. 11/593,056, filed Nov. 6, 2006 by Waterhouse et al.
Information Disclosure Statement dated Mar. 8, 2007 in U.S. Appl. No. 11/593,056, filed Nov. 6, 2006 by Waterhouse et al.
Preliminary Amendment dated Nov. 6, 2006 in U.S. Appl. No. 11/593,056, filed Nov. 6, 2006 by Waterhouse et al.
U.S. Appl. No. 11/179,504, filed Jul. 13, 2005 by Waterhouse et al.
Non-Final Rejection dated Nov. 10, 2008 in U.S. Appl. No. 11/179,504, filed Jul. 13, 2005 by Waterhouse et al.
List of references dated Nov. 10, 2008 in U.S. Appl. No. 11/179,504, filed Jul. 13, 2005 by Waterhouse et al.
Search information including classification, databases and other search related notes dated Nov. 10, 2008 in U.S. Appl. No. 11/179,504, filed Jul. 13, 2005 by Waterhouse et al.
Information Disclosure Statement dated Sep. 8, 2008 in U.S. Appl. No. 11/179,504, filed Jul. 13, 2005 by Waterhouse et al.
Response to Election / Restriction dated Sep. 4, 2008 in U.S. Appl. No. 11/179,504, filed Jul. 13, 2005 by Waterhouse et al.
Requirement for Restriction/Election dated Jul. 30, 2008 in U.S. Appl. No. 11/179,504, filed Jul. 13, 2005 by Waterhouse et al.
Amendment Submitted/Entered with Filing of CPA/RCE dated Jun. 23, 2008 in U.S. Appl. No. 11/179,504, filed Jul. 13, 2005 by Waterhouse et al.
Advisory Action dated Jun. 6, 2008 in U.S. Appl. No. 11/179,504, filed Jul. 13, 2005 by Waterhouse et al.
List of References dated Jun. 6, 2008 in U.S. Appl. No. 11/179,504, filed Jul. 13, 2005 by Waterhouse et al.
Amendment Submitted/Entered with Filing of CPA/RCE dated May 21, 2008 in U.S. Appl. No. 11/179,504, filed Jul. 13, 2005 by Waterhouse et al.
Information Disclosure Statement dated Mar. 26, 2008 in U.S. Appl. No. 11/179,504, filed Jul. 13, 2005 by Waterhouse et al.
Final Rejection dated Mar. 21, 2008 in U.S. Appl. No. 11/179,504, filed Jul. 13, 2005 by Waterhouse et al.
List of References dated Mar. 21, 2008 in U.S. Appl. No. 11/179,504, filed Jul. 13, 2005 by Waterhouse at al.
List of References dated Mar. 21, 2008 in U.S. Appl. No. 11/179,504, filed Jul. 13, 2005 by Waterhouse et al.
Search information including classification, databases and other search related notes dated Mar. 21, 2008 in U.S. Appl. No. 11/179,504, filed Jul. 13, 2005 by Waterhouse et al.
Amendment After Final dated Feb. 15, 2008 in U.S. Appl. No. 11/179,504, filed Jul. 13, 2005 by Waterhouse et al.
Rule 130, 131 or 132 Affidavits dated Feb. 15, 2008 in U.S. Appl. No. 11/179,504, filed Jul. 13, 2005 by Waterhouse et al.
Examiner Interview Summary Record dated Feb. 1, 2008 in U.S. Appl. No. 11/179,504, filed Jul. 13, 2005 by Waterhouse et al.
Information Disclosure Statement Letter dated Jan. 28, 2008 in U.S. Appl. No. 11/179,504, filed Jul. 13, 2005 by Waterhouse et al.
Information Disclosure Statement dated Jan. 28, 2008 in U.S. Appl. No. 11/179,504, filed Jul. 13, 2005 by Waterhouse et al.
Final Rejection dated Dec. 20, 2007 in U.S. Appl. No. 11/179,504, filed Jul. 13, 2005 by Waterhouse et al.
List of References dated Dec. 20, 2007 in U.S. Appl. No. 11/179,504, filed Jul. 13, 2005 by Waterhouse et al.
Search information including classification, databases and other search related notes dated Dec. 20, 2007 in U.S. Appl. No. 11/179,504, filed Jul. 13, 2005 by Waterhouse et al.
Information Disclosure Statement dated Oct. 22, 2007 in U.S. Appl. No. 11/179,504, filed Jul. 13, 2005 by Waterhouse et al.
Amendment/Req. Reconsideration—After Non-Final Reject dated Oct. 22, 2007 in U.S. Appl. No. 11/179,504, filed Jul. 13, 2005 by Waterhouse et al.
Rule 130, 131 or 132 Affidavits dated Oct. 22, 2007 in U.S. Appl. No. 11/179,504, filed Jul. 13, 2005 by Waterhouse et al.
Non-Final Rejection dated Apr. 18, 2007 in U.S. Appl. No. 11/179,504, filed Jul. 13, 2005 by Waterhouse et al.
List of References dated Apr. 18, 2007 in U.S. Appl. No. 11/179,504, filed Jul. 13, 2005 by Waterhouse et al.
Search information including classification, databases and other search related notes dated Apr. 18, 2007 in U.S. Appl. No. 11/179,504, filed Jul. 13, 2005 by Waterhouse et al.
Amendment/Req. Reconsideration—After Non-Final Reject dated Mar. 5, 2007 in U.S. Appl. No. 11/179,504, filed Jul. 13, 2005 by Waterhouse et al.
Requirement for Restriction/Election dated Jan. 30, 2007 in U.S. Appl. No. 11/179,504, filed Jul. 13, 2005 by Waterhouse et al.
Preliminary Amendment dated Jul. 13, 2005 in U.S. Appl. No. 11/179,504, filed Jul. 13, 2005 by Waterhouse et al.
U.S. Appl. No. 09/100,812, filed Jun. 19, 1998 by Graham et al.
Notice of Allowance dated Nov. 20, 2002 in U.S. Appl. No. 09/100,812, filed Jun. 19, 1998 by Graham et. al.
List of References dated Nov. 20, 2002 in U.S. Appl. No. 09/100,812, filed Jun. 19, 1998 by Graham et. al.
Examiner's search strategy and results dated Nov. 12, 2002 in U.S. Appl. No. 09/100,812, filed Jun. 19, 1998 by Graham et al.

(56) References Cited

OTHER PUBLICATIONS

Amendment/Req. Reconsideration—After Non-Final Reject dated Oct. 17, 2002 in U.S. Appl. No. 09/100,812, filed Jun. 19, 1998 by Graham et. al.
Amendment/Req. Reconsideration—After Non-Final Reject dated Sep. 26, 2002 in U.S. Appl. No. 09/100,812, filed Jun. 19, 1998 by Graham et. al.
Rule 130, 131 or 132 Affidavits dated Sep. 26, 2002 in U.S. Appl. No. 09/100,812, filed Jun. 19, 1998 by Graham et. al.
Examiner Interview Summary Record dated Sep. 18, 2002 in U.S. Appl. No. 09/100,812, filed Jun. 19, 1998 by Graham et al.
Information Disclosure Statement dated Sep. 6, 2002 in U.S. Appl. No. 09/100,812, filed Jun. 19, 1998 by Graham et al.
Information Disclosure Statement dated Jun. 25, 2002 in U.S. Appl. No. 09/100,812, filed Jun. 19, 1998 by Graham et al.
Amendment/Req. Reconsideration—After Non-Final Reject dated May 6, 2002 in U.S. Appl. No. 09/100,812, filed Jun. 19, 1998 by Graham et. al.
Rule 130, 131 or 132 Affidavits dated May 6, 2002 in U.S. Appl. No. 09/100,812, filed Jun. 19, 1998 by Graham et. al.
Amendment/Req. Reconsideration—After Non-Final Reject dated Mar. 12, 2002 in U.S. Appl. No. 09/100,812, filed Jun. 19, 1998 by Graham et. al.
Advisory Action dated Feb. 15, 2002 in U.S. Appl. No. 09/100,812, filed Jun. 19, 1998 by Graham et. al.
Examiner's search strategy and results dated Feb. 4, 2002 in U.S. Appl. No. 09/100,812, filed Jun. 19, 1998 by Graham et. al.
Amendment/Req. Reconsideration—After Non-Final Reject dated Dec. 31, 2001 in U.S. Appl. No. 09/100,812, filed Jun. 19, 1998 by Graham et. al.
Final Rejection dated Feb. 12, 2001 in U.S. Appl. No. 09/100,812, filed Jun. 19, 1998 by Graham et. al.
List of References dated Feb. 12, 2001 in U.S. Appl. No. 09/100,812, filed Jun. 19, 1998 by Graham et. al.
Examiner Interview Summary Record dated Jan. 11, 2001 in U.S. Appl. No. 09/100,812, filed Jun. 19, 1998 by Graham et. al.
Information Disclosure Statement dated Dec. 26, 2000 in U.S. Appl. No. 09/100,812, filed Jun. 19, 1998 by Graham et. al.
Amendment/Req. Reconsideration—After Non-Final Reject dated Nov. 14, 2000 in U.S. Appl. No. 09/100,812, filed Jun. 19, 1998 by Graham et. al.
Non-Final Rejection dated May 10, 2000 in U.S. Appl. No. 09/100,812, filed Jun. 19, 1998 by Graham et. al.
List of references dated May 10, 2000 in U.S. Appl. No. 09/100,812, filed Jun. 19, 1998 by Graham et. al.
Examiner's search strategy and results dated May 6, 2000 in U.S. Appl. No. 09/100,812, filed Jun. 19, 1998 by Graham et. al.
Amendment/Req. Reconsideration—After Non-Final Reject dated Apr. 12, 2000 in U.S. Appl. No. 09/100,812, filed Jun. 19, 1998 by Graham et. al.
Requirement for Restriction/Election dated Dec. 2, 1999 in U.S. Appl. No. 09/100,812, filed Jun. 19, 1998 by Graham et. al.
U.S. Appl. No. 09/646,807, filed Dec. 5, 2000 by Graham et al.
Non-Final Rejection dated Jul. 8, 2008 in U.S. Appl. No. 09/646,807, filed Dec. 5, 2000 by Graham et. al.
List of references dated Jul. 8, 2008 in U.S. Appl. No. 09/646,807, filed Dec. 5, 2000 by Graham et. al.
Search information including classification, databases and other search related notes dated Jul. 8, 2008 in U.S. Appl. No. 09/646,807, filed Dec. 5, 2000 by Graham et. al.
Information Disclosure Statement dated Mar. 27, 2008 in U.S. Appl. No. 09/646,807, filed Dec. 5, 2000 by Graham et. al.
Protest Documents filed by 3rd Party dated Feb. 22, 2008 in U.S. Appl. No. 09/646,807, filed Dec. 5, 2000 by Graham et. al.
Information Disclosure Statement dated Jan. 28, 2008 in U.S. Appl. No. 09/646,807, filed Dec. 5, 2000 by Graham et. al.
Rule 130, 131 or 132 Affidavits dated Dec. 17, 2007 in U.S. Appl. No. 09/646,807, filed Dec. 5, 2000 by Graham et. al.
Amendment/Req. Reconsideration—After Non-Final Reject dated Dec. 28, 2006 in U.S. Appl. No. 09/646,807, filed Dec. 5, 2000 by Graham et. al.
Information Disclosure Statement dated Dec. 28, 2006 in U.S. Appl. No. 09/646,807, filed Dec. 5, 2000 by Graham et. al.
Petition Decision dated Oct. 2, 2006 in U.S. Appl. No. 09/646,807, filed Dec. 5, 2000 by Graham et. al.
Non-Final Rejection dated Jun. 28, 2006 in U.S. Appl. No. 09/646,807, filed Dec. 5, 2000 by Graham et. al.
List of References dated Jun. 28, 2006 in U.S. Appl. No. 09/646,807, filed Dec. 5, 2000 by Graham et. al.
Search information including classification, databases and other search related notes dated Jun. 28, 2006 in U.S. Appl. No. 09/646,807, filed Dec. 5, 2000 by Graham et. al.
Examiner's search strategy and results dated Jun. 20, 2006 in U.S. Appl. No. 09/646,807, filed Dec. 5, 2000 by Graham et. al.
Petition dated Jun. 12, 2006 in U.S. Appl. No. 09/646,807, filed Dec. 5, 2000 by Graham et. al.
Information Disclosure Statement dated Jan. 25, 2006 in U.S. Appl. No. 09/646,807, filed Dec. 5, 2000 by Graham et. al.
Amendment/Req. Reconsideration—After Non-Final Reject dated Dec. 27, 2005 in U.S. Appl. No. 09/646,807, filed Dec. 5, 2000 by Graham et. al.
Information Disclosure Statement dated Jun. 30, 2005 in U.S. Appl. No. 09/646,807, filed Dec. 5, 2000 by Graham et. al.
Information Disclosure Statement dated Feb. 11, 2005 in U.S. Appl. No. 09/646,807, filed Dec. 5, 2000 by Graham et. al.
Amendment Submitted/Entered with Filing of CPA/RCE dated Dec. 7, 2004 in U.S. Appl. No. 09/646,807, filed Dec. 5, 2000 by Graham et. al.
Information Disclosure Statement dated Nov. 18, 2004 in U.S. Appl. No. 09/646,807, filed Dec. 5, 2000 by Graham et. al.
Final Rejection dated Dec. 17, 2003 in U.S. Appl. No. 09/646,807, filed Dec. 5, 2000 by Graham et. al.
List of References dated Dec. 17, 2003 in U.S. Appl. No. 09/646,807, filed Dec. 5, 2000 by Graham et. al.
Search information including classification, databases and other search related notes dated Dec. 17, 2003 in U.S. Appl. No. 09/646,807, filed Dec. 5, 2000 by Graham et. al.
Examiner's search strategy and results dated Dec. 10, 2003 in U.S. Appl. No. 09/646,807, filed Dec. 5, 2000 by Graham et. al.
Amendment/Req. Reconsideration—After Non-Final Reject dated Sep. 11, 2003 in U.S. Appl. No. 09/646,807, filed Dec. 5, 2000 by Graham et. al.
Information Disclosure Statement dated Sep. 11, 2003 in U.S. Appl. No. 09/646,807, filed Dec. 5, 2000 by Graham et. al.
Non-Final Rejection dated Mar. 7, 2003 in U.S. Appl. No. 09/646,807, filed Dec. 5, 2000 by Graham et. al.
List of References dated Mar. 7, 2003 in U.S. Appl. No. 09/646,807, filed Dec. 5, 2000 by Graham et. al.
Examiner's search strategy and results dated Feb. 26, 2003 in U.S. Appl. No. 09/646,807, filed Dec. 5, 2000 by Graham et. al.
Response to Election / Restriction Filed dated Dec. 24, 2002 in U.S. Appl. No. 09/646,807, filed Dec. 5, 2000 by Graham et. al.
Applicant Arguments/Remarks Made in an Amendment dated Dec. 24, 2002 in U.S. Appl. No. 09/646,807, filed Dec. 5, 2000 by Graham et. al.
Requirement for Restriction/Election dated Nov. 18, 2002 in U.S. Appl. No. 09/646,807, filed Dec. 5, 2000 by Graham et. al.
Information Disclosure Statement (IDS) Filed (SB/08) dated Sep. 16, 2002 in U.S. Appl. No. 09/646,807, filed Dec. 5, 2000 by Graham et. al.
Preliminary Amendment dated Aug. 2, 2001 in U.S. Appl. No. 09/646,807, filed Dec. 5, 2000 by Graham et. al.
Preliminary Amendment dated May 14, 2001 in U.S. Appl. No. 09/646,807, filed Dec. 5, 2000 by Graham et. al.
Information Disclosure Statement dated May 14, 2001 in U.S. Appl. No. 09/646,807, filed Dec. 5, 2000 by Graham et. al.
Third Party Submission after Publication under 37 CFR 1.99 after publication of a patent dated Dec. 5, 2000 in U.S. Appl. No. 09/646,807, filed Dec. 5, 2000 by Graham et. al.
Preliminary Amendment dated Sep. 20, 2000 in U.S. Appl. No. 09/646,807, filed Dec. 5, 2000 by Graham et. al.

(56) References Cited

OTHER PUBLICATIONS

Search information including classification, databases and other search related notes dated Sep. 20, 2000 in U.S. Appl. No. 09/646,807, filed Dec. 5, 2000 by Graham et. al.
Documents submitted with 371 Applications dated Sep. 20, 2000 in U.S. Appl. No. 09/646,807, filed Dec. 5, 2000 by Graham et. al.
Certified Copy of Foreign Priority Application dated Sep. 20, 2000 in U.S. Appl. No. 09/646,807, filed Dec. 5, 2000 by Graham et. al.
U.S. Appl. No. 09/997,905, filed Nov. 30, 2001 by Graham et al.
Information Disclosure Statement dated Sep. 22, 2003 in U.S. Appl. No. 09/997,905, filed Nov. 30, 2001 by Graham et. al.
Information Disclosure Statement dated Sep. 16, 2002 in U.S. Appl. No. 09/997,905, filed Nov. 30, 2001 by Graham et. al.
U.S. Appl. No. 10/346,853, filed Jan. 17, 2003 by Graham et al.
Petition decision dated May 8, 2009 in U.S. Appl. No. 10/346,853, filed Jan. 17, 2003 by Graham et. al.
Information Disclosure Statement dated Apr. 13, 2009 in U.S. Appl. No. 10/346,853, filed Jan. 17, 2003 by Graham et. al.
Amendment After Final dated Jan. 12, 2009 in U.S. Appl. No. 10/346,853, filed Jan. 17, 2003 by Graham et. al.
Information Disclosure Statement dated Oct. 10, 2008 in U.S. Appl. No. 10/346,853, filed Jan. 17, 2003 by Graham et. al.
Final Rejection dated Jul. 7, 2008 in U.S. Appl. No. 10/346,853, filed Jan. 17, 2003 by Graham et. al.
List of references dated Jul. 7, 2008 in U.S. Appl. No. 10/346,853, filed Jan. 17, 2003 by Graham et. al.
Search information including classification, databases and other search related notes dated Jul. 7, 2008 in U.S. Appl. No. 10/346,853, filed Jan. 17, 2003 by Graham et. al.
Information Disclosure Statement dated Jun. 4, 2008 in U.S. Appl. No. 10/346,853, filed Jan. 17, 2003 by Graham et. al.
Response to Election / Restriction Filed dated Apr. 21, 2008 in U.S. Appl. No. 10/346,853, filed Jan. 17, 2003 by Graham et. al.
Information Disclosure Statement dated Mar. 26, 2008 in U.S. Appl. No. 10/346,853, filed Jan. 17, 2003 by Graham et. al.
Protest Documents filed by 3rd Party dated Feb. 22, 2008 in U.S. Appl. No. 10/346,853, filed Jan. 17, 2003 by Graham et. al.
Information Disclosure Statement dated Jan. 28, 2008 in U.S. Appl. No. 10/346,853, filed Jan. 17, 2003 by Graham et. al.
Requirement for Restriction/Election dated Jan. 16, 2008 in U.S. Appl. No. 10/346,853, filed Jan. 17, 2003 by Graham et. al.
Examiner Interview Summary Record dated Dec. 11, 2007 in U.S. Appl. No. 10/346,853, filed Jan. 17, 2003 by Graham et. al.
Information Disclosure Statement dated Oct. 17, 2007 in U.S. Appl. No. 10/346,853, filed Jan. 17, 2003 by Graham et. al.
Amendment/Req. Reconsideration—After Non-Final Reject dated Oct. 17, 2007 in U.S. Appl. No. 10/346,853, filed Jan. 17, 2003 by Graham et. al.
Rule 130, 131 or 132 Affidavits dated Oct. 17, 2007 in U.S. Appl. No. 10/346,853, filed Jan. 17, 2003 by Graham et. al.
Non-Final Rejection dated Apr. 17, 2007 in U.S. Appl. No. 10/346,853, filed Jan. 17, 2003 by Graham et. al.
List of References dated Apr. 17, 2007 in U.S. Appl. No. 10/346,853, filed Jan. 17, 2003 by Graham et. al.
Search information including classification, databases and other search related notes dated Apr. 17, 2007 in U.S. Appl. No. 10/346,853, filed Jan. 17, 2003 by Graham et. al.
Amendment/Req. Reconsideration—After Non-Final Reject dated Feb. 22, 2007 in U.S. Appl. No. 10/346,853, filed Jan. 17, 2003 by Graham et. al.
Petition dated Dec. 28, 2006 in U.S. Appl. No. 10/346,853, filed Jan. 17, 2003 by Graham et. al.
Information Disclosure Statement dated Dec. 28, 2006 in U.S. Appl. No. 10/346,853, filed Jan. 17, 2003 by Graham et. al.
Amendment/Req. Reconsideration—After Non-Final Reject dated Dec. 28, 2006 in U.S. Appl. No. 10/346,853, filed Jan. 17, 2003 by Graham et. al.
Petition Decision dated Oct. 10, 2006 in U.S. Appl. No. 10/346,853, filed Jan. 17, 2003 by Graham et. al.
Non-Final Rejection dated Jun. 27, 2006 in U.S. Appl. No. 10/346,853, filed Jan. 17, 2003 by Graham et. al.
List of References dated Jun. 27, 2006 in U.S. Appl. No. 10/346,853, filed Jan. 17, 2003 by Graham et. al.
Search information including classification, databases and other search related notes dated Jun. 27, 2006 in U.S. Appl. No. 10/346,853, filed Jan. 17, 2003 by Graham et. al.
Examiner's search strategy and results dated Jun. 20, 2006 in U.S. Appl. No. 10/346,853, filed Jan. 17, 2003 by Graham et. al.
Petition dated Jun. 12, 2006 in U.S. Appl. No. 10/346,853, filed Jan. 17, 2003 by Graham et. al.
Response to Election / Restriction dated Aug. 2, 2005 in U.S. Appl. No. 10/346,853, filed Jan. 17, 2003 by Graham et. al.
Requirement for Restriction/Election dated Jul. 22, 2005 in U.S. Appl. No. 10/346,853, filed Jan. 17, 2003 by Graham et. al.
Information Disclosure Statement dated Jul. 1, 2005 in U.S. Appl. No. 10/346,853, filed Jan. 17, 2003 by Graham et. al.
Information Disclosure Statement dated Feb. 25, 2005 in U.S. Appl. No. 10/346,853, filed Jan. 17, 2003 by Graham et. al.
Information Disclosure Statement dated Feb. 11, 2005 in U.S. Appl. No. 10/346,853, filed Jan. 17, 2003 by Graham et. al.
Information Disclosure Statement dated Dec. 9, 2004 in U.S. Appl. No. 10/346,853, filed Jan. 17, 2003 by Graham et. al.
Information Disclosure Statement dated Jul. 30, 2004 in U.S. Appl. No. 10/346,853, filed Jan. 17, 2003 by Graham et. al.
Information Disclosure Statement dated Jan. 20, 2004 in U.S. Appl. No. 10/346,853, filed Jan. 17, 2003 by Graham et. al.
Information Disclosure Statement dated Sep. 22, 2003 in U.S. Appl. No. 10/346,853, filed Jan. 17, 2003 by Graham et. al.
Information Disclosure Statement dated Jul. 7, 2003 in U.S. Appl. No. 10/346,853, filed Jan. 17, 2003 by Graham et. al.
Information Disclosure Statement dated Jun. 20, 2003 in U.S. Appl. No. 10/346,853, filed Jan. 17, 2003 by Graham et. al.
Preliminary Amendment dated Mar. 31, 2003 in U.S. Appl. No. 10/346,853, filed Jan. 17, 2003 by Graham et. al.
Preliminary Amendment dated Jan. 17, 2003 in U.S. Appl. No. 10/346,853, filed Jan. 17, 2003 by Graham et. al.
U.S. Appl. No. 10/646,070, filed Aug. 22, 2003 by Graham et al.
Final Rejection dated Nov. 4, 2008 in U.S. Appl. No. 10/646,070, filed Aug. 22, 2003 by Graham et. al.
List of references dated Nov. 4, 2008 in U.S. Appl. No. 10/646,070, filed Aug. 22, 2003 by Graham et. al.
Search information including classification, databases and other search related notes dated Nov. 4, 2008 in U.S. Appl. No. 10/646,070, filed Aug. 22, 2003 by Graham et. al.
Information Disclosure Statement dated Oct. 10, 2008 in U.S. Appl. No. 10/646,070, filed Aug. 22, 2003 by Graham et. al.
Supplemental Response dated Oct. 10, 2008 in U.S. Appl. No. 10/646,070, filed Aug. 22, 2003 by Graham et. al.
Amendment/Req. Reconsideration—After Non-Final Reject dated Jul. 29, 2008 in U.S. Appl. No. 10/646,070, filed Aug. 22, 2003 by Graham et. al.
Rule 130, 131 or 132 Affidavits dated Jul. 29, 2008 in U.S. Appl. No. 10/646,070, filed Aug. 22, 2003 by Graham et. al.
Information Disclosure Statement dated Jul. 29, 2008 in U.S. Appl. No. 10/646,070, filed Aug. 22, 2003 by Graham et. al.
Information Disclosure Statement dated Mar. 26, 2008 in U.S. Appl. No. 10/646,070, filed Aug. 22, 2003 by Graham et. al.
Protest Documents filed by 3rd Party dated Feb. 22, 2008 in U.S. Appl. No. 10/646,070, filed Aug. 22, 2003 by Graham et. al.
Information Disclosure Statement dated Jan. 31, 2008 in U.S. Appl. No. 10/646,070, filed Aug. 22, 2003 by Graham et. al.
Non-Final Rejection dated Jan. 24, 2008 in U.S. Appl. No. 10/646,070, filed Aug. 22, 2003 by Graham et. al.
List of References dated Jan. 24, 2008 in U.S. Appl. No. 10/646,070, filed Aug. 22, 2003 by Graham et. al.
Search information including classification, databases and other search related notes dated Jan. 24, 2008 in U.S. Appl. No. 10/646,070, filed Aug. 22, 2003 by Graham et. al.
Examiner Interview Summary Record dated Dec. 11, 2007 in U.S. Appl. No. 10/646,070, filed Aug. 22, 2003 by Graham et. al.
Amendment After Final dated Oct. 29, 2007 in U.S. Appl. No. 10/646,070, filed Aug. 22, 2003 by Graham et. al.

(56) References Cited

OTHER PUBLICATIONS

Information Disclosure Statement dated Oct. 29, 2007 in U.S. Appl. No. 10/646,070, filed Aug. 22, 2003 by Graham et. al.
Rule 130, 131 or 132 Affidavits dated Oct. 29, 2007 in U.S. Appl. No. 10/646,070, filed Aug. 22, 2003 by Graham et. al.
Final Rejection dated Apr. 27, 2007 in U.S. Appl. No. 10/646,070, filed Aug. 22, 2003 by Graham et. al.
List of References dated Apr. 27, 2007 in U.S. Appl. No. 10/646,070, filed Aug. 22, 2003 by Graham et. al.
Search information including classification, databases and other search related notes dated Apr. 27, 2007 in U.S. Appl. No. 10/646,070, filed Aug. 22, 2003 by Graham et. al.
Information Disclosure Statement dated Mar. 5, 2007 in U.S. Appl. No. 10/646,070, filed Aug. 22, 2003 by Graham et. al.
Amendment/Req. Reconsideration—After Non-Final Reject dated Feb. 28, 2007 in U.S. Appl. No. 10/646,070, filed Aug. 22, 2003 by Graham et. al.
Non-Final Rejection dated Aug. 28, 2006 in U.S. Appl. No. 10/646,070, filed Aug. 22, 2003 by Graham et. al.
List of references dated Aug. 28, 2006 in U.S. Appl. No. 10/646,070, filed Aug. 22, 2003 by Graham et. al.
Supplemental Response dated Aug. 11, 2006 in U.S. Appl. No. 10/646,070, filed Aug. 22, 2003 by Graham et. al.
Amendment/Req. Reconsideration—After Non-Final Reject dated Jul. 24, 2006 in U.S. Appl. No. 10/646,070, filed Aug. 22, 2003 by Graham et. al.
Examiner's search strategy and results dated Jun. 15, 2006 in U.S. Appl. No. 10/646,070, filed Aug. 22, 2003 by Graham et. al.
Examiner's search strategy and results dated Jun. 14, 2006 in U.S. Appl. No. 10/646,070, filed Aug. 22, 2003 by Graham et. al.
Amendment/Req. Reconsideration—After Non-Final Reject dated Dec. 27, 2005 in U.S. Appl. No. 10/646,070, filed Aug. 22, 2003 by Graham et. al.
Information Disclosure Statement dated Jun. 30, 2005 in U.S. Appl. No. 10/646,070, filed Aug. 22, 2003 by Graham et. al.
Foreign Reference dated Jun. 30, 2005 in U.S. Appl. No. 10/646,070, filed Aug. 22, 2003 by Graham et. al.
Amendment/Req. Reconsideration—After Non-Final Reject dated Apr. 7, 2005 in U.S. Appl. No. 10/646,070, filed Aug. 22, 2003 by Graham et. al.
Information Disclosure Statement dated Feb. 28, 2005 in U.S. Appl. No. 10/646,070, filed Aug. 22, 2003 by Graham et. al.
Information Disclosure Statement dated Feb. 11, 2005 in U.S. Appl. No. 10/646,070, filed Aug. 22, 2003 by Graham et. al.
Response to Election / Restriction dated Dec. 15, 2004 in U.S. Appl. No. 10/646,070, filed Aug. 22, 2003 by Graham et. al.
Requirement for Restriction/Election dated Oct. 15, 2004 in U.S. Appl. No. 10/646,070, filed Aug. 22, 2003 by Graham et. al.
Petition Decision dated Sep. 10, 2004 in U.S. Appl. No. 10/646,070, filed Aug. 22, 2003 by Graham et. al.
Information Disclosure Statement dated Jul. 30, 2004 in U.S. Appl. No. 10/646,070, filed Aug. 22, 2003 by Graham et. al.
Petition Entered dated Jul. 27, 2004 in U.S. Appl. No. 10/646,070, filed Aug. 22, 2003 by Graham et. al.
Request for Corrected Filing Receipt dated Dec. 11, 2003 in U.S. Appl. No. 10/646,070, filed Aug. 22, 2003 by Graham et. al.
Preliminary Amendment dated Dec. 11, 2003 in U.S. Appl. No. 10/646,070, filed Aug. 22, 2003 by Graham et. al.
Preliminary Amendment dated Aug. 22, 2003 in U.S. Appl. No. 10/646,070, filed Aug. 22, 2003 by Graham et. al.
U.S. Appl. No. 10/759,841, filed Jan. 15, 2004 by Graham et al.
Examiner Interview Summary Record dated Feb. 20, 2009 in U.S. Appl. No. 10/759,841, filed Jan. 15, 2004 by Graham et. al.
Final Rejection dated Jan. 22, 2009 in U.S. Appl. No. 10/759,841, filed Jan. 15, 2004 by Graham et. al.
Search information including classification, databases and other search related notes dated Jan. 22, 2009 in U.S. Appl. No. 10/759,841, filed Jan. 15, 2004 by Graham et. al.
Final Rejection dated Jan. 6, 2009 in U.S. Appl. No. 10/759,841, filed Jan. 15, 2004 by Graham et. al.
List of references dated Jan. 6, 2009 in U.S. Appl. No. 10/759,841, filed Jan. 15, 2004 by Graham et. al.
Search information including classification, databases and other search related notes dated Jan. 6, 2009 in U.S. Appl. No. 10/759,841, filed Jan. 15, 2004 by Graham et. al.
Examiner Interview Summary Record dated Dec. 31, 2008 in U.S. Appl. No. 10/759,841, filed Jan. 15, 2004 by Graham et. al.
Amendment/Req. Reconsideration—After Non-Final Reject dated Oct. 14, 2008 in U.S. Appl. No. 10/759,841, filed Jan. 15, 2004 by Graham et. al.
Information Disclosure Statement (IDS) Filed (SB/08) dated Oct. 14, 2008 in U.S. Appl. No. 10/759,841, filed Jan. 15, 2004 by Graham et. al.
Non-Final Rejection dated Jul. 9, 2008 in U.S. Appl. No. 10/759,841, filed Jan. 15, 2004 by Graham et. al.
Search information including classification, databases and other search related notes dated Jul. 9, 2008 in U.S. Appl. No. 10/759,841, filed Jan. 15, 2004 by Graham et. al.
List of References dated Jul. 9, 2008 in U.S. Appl. No. 10/759,841, filed Jan. 15, 2004 by Graham et. al.
Information Disclosure Statement (IDS) Filed (SB/08) dated Jun. 27, 2008 in U.S. Appl. No. 10/759,841, filed Jan. 15, 2004 by Graham et. al.
Information Disclosure Statement (IDS) Filed (SB/08) dated Apr. 18, 2008 in U.S. Appl. No. 10/759,841, filed Jan. 15, 2004 by Graham et. al.
Amendment After Final dated Apr. 18, 2008 in U.S. Appl. No. 10/759,841, filed Jan. 15, 2004 by Graham et. al.
Certified Foreign Priority Application dated Apr. 18, 2008 in U.S. Appl. No. 10/759,841, filed Jan. 15, 2004 by Graham et. al.
Rule 130, 131 or 132 Affidavits dated Apr. 18, 2008 in U.S. Appl. No. 10/759,841, filed Jan. 15, 2004 by Graham et. al.
Information Disclosure Statement (IDS) Filed (SB/08) dated Mar. 26, 2008 in U.S. Appl. No. 10/759,841, filed Jan. 15, 2004 by Graham et. al.
Protest Documents filed by 3rd Party dated Feb. 22, 2008 in U.S. Appl. No. 10/759,841, filed Jan. 15, 2004 by Graham et. al.
Information Disclosure Statement (IDS) Filed (SB/08) dated Jan. 28, 2008 in U.S. Appl. No. 10/759,841, filed Jan. 15, 2004 by Graham et. al.
Final Rejection dated Jan. 8, 2008 in U.S. Appl. No. 10/759,841, filed Jan. 15, 2004 by Graham et. al.
List of References dated Jan. 8, 2008 in U.S. Appl. No. 10/759,841, filed Jan. 15, 2004 by Graham et. al.
Search information including classification, databases and other search related notes dated Jan. 8, 2008 in U.S. Appl. No. 10/759,841, filed Jan. 15, 2004 by Graham et. al.
Examiner Interview Summary Record dated Dec. 11, 2007 in U.S. Appl. No. 10/759,841, filed Jan. 15, 2004 by Graham et. al.
Amendment/Req. Reconsideration—After Non-Final Reject dated Oct. 25, 2007 in U.S. Appl. No. 10/759,841, filed Jan. 15, 2004 by Graham et. al.
Rule 130, 131 or 132 Affidavits dated Oct. 25, 2007 in U.S. Appl. No. 10/759,841, filed Jan. 15, 2004 by Graham et. al.
Information Disclosure Statement (IDS) Filed (SB/08) dated Oct. 25, 2007 in U.S. Appl. No. 10/759,841, filed Jan. 15, 2004 by Graham et. al.
Non-Final Rejection dated Apr. 25, 2007 in U.S. Appl. No. 10/759,841, filed Jan. 15, 2004 by Graham et. al.
List of References dated Apr. 25, 2007 in U.S. Appl. No. 10/759,841, filed Jan. 15, 2004 by Graham et. al.
Search information including classification, databases and other search related notes dated Apr. 25, 2007 in U.S. Appl. No. 10/759,841, filed Jan. 15, 2004 by Graham et. al.
Examiner's search strategy and results dated Apr. 13, 2007 in U.S. Appl. No. 10/759,841, filed Jan. 15, 2004 by Graham et. al.
Amendment/Req. Reconsideration—After Non-Final Reject dated Feb. 21, 2007 in U.S. Appl. No. 10/759,841, filed Jan. 15, 2004 by Graham et. al.
Response to Election / Restriction Filed dated Dec. 29, 2006 in U.S. Appl. No. 10/759,841, filed Jan. 15, 2004 by Graham et. al.
Requirement for Restriction/Election dated Nov. 29, 2006 in U.S. Appl. No. 10/759,841, filed Jan. 15, 2004 by Graham et. al.

(56) References Cited

OTHER PUBLICATIONS

Response to Election / Restriction Filed dated Oct. 31, 2006 in U.S. Appl. No. 10/759,841, filed Jan. 15, 2004 by Graham et. al.
Petition Decision dated Sep. 12, 2006 in U.S. Appl. No. 10/759,841, filed Jan. 15, 2004 by Graham et. al.
Requirement for Restriction/Election dated Jul. 31, 2006 in U.S. Appl. No. 10/759,841, filed Jan. 15, 2004 by Graham et. al.
Petition for review by the Office of Petitions. dated Jun. 12, 2006 in U.S. Appl. No. 10/759,841, filed Jan. 15, 2004 by Graham et. al.
Information Disclosure Statement (IDS) Filed (SB/08) dated Jun. 30, 2005 in U.S. Appl. No. 10/759,841, filed Jan. 15, 2004 by Graham et. al.
Information Disclosure Statement (IDS) Filed (SB/08) dated Feb. 25, 2005 in U.S. Appl. No. 10/759,841, filed Jan. 15, 2004 by Graham et. al.
Information Disclosure Statement (IDS) Filed (SB/08) dated Feb. 11, 2005 in U.S. Appl. No. 10/759,841, filed Jan. 15, 2004 by Graham et. al.
Information Disclosure Statement (IDS) Filed (SB/08) dated Dec. 21, 2004 in U.S. Appl. No. 10/759,841, filed Jan. 15, 2004 by Graham et. al.
Information Disclosure Statement (IDS) Filed (SB/08) dated Aug. 4, 2004 in U.S. Appl. No. 10/759,841, filed Jan. 15, 2004 by Graham et. al.
Preliminary Amendment dated Jan. 15, 2004 in U.S. Appl. No. 10/759,841, filed Jan. 15, 2004 by Graham et. al.
U.S. Appl. No. 10/821,710, filed Apr. 8, 2004 by Graham et al.
Abandonment dated Dec. 15, 2008 in U.S. Appl. No. 10/821,710, filed Apr. 8, 2004 by Graham et. al.
Final Rejection dated Apr. 17, 2008 in U.S. Appl. No. 10/821,710, filed Apr. 8, 2004 by Graham et. al.
Search information including classification, databases and other search related notes dated Apr. 7, 2008 in U.S. Appl. No. 10/821,710, filed Apr. 8, 2004 by Graham et. al.
List of References dated Apr. 17, 2008 in U.S. Appl. No. 10/821,710, filed Apr. 8, 2004 by Graham et. al.
Information Disclosure Statement dated Mar. 26, 2008 in U.S. Appl. No. 10/821,710, filed Apr. 8, 2004 by Graham et. al.
Information Disclosure Statement dated Feb. 29, 2008 in U.S. Appl. No. 10/821,710, filed Apr. 8, 2004 by Graham et. al.
Amendment/Req. Reconsideration—After Non-Final Reject dated Feb. 11, 2008 in U.S. Appl. No. 10/821,710, filed Apr. 8, 2004 by Graham et. al.
Information Disclosure Statement dated Jan. 28, 2008 in U.S. Appl. No. 10/821,710, filed Apr. 8, 2004 by Graham et. al.
Amendment/Req. Reconsideration—After Non-Final Reject dated Nov. 2, 2007 in U.S. Appl. No. 10/821,710, filed Apr. 8, 2004 by Graham et. al.
Non-Final Rejection dated Aug. 7, 2007 in U.S. Appl. No. 10/821,710, filed Apr. 8, 2004 by Graham et. al.
List of references dated Aug. 7, 2007 in U.S. Appl. No. 10/821,710, filed Apr. 8, 2004 by Graham et. al.
Search information including classification, databases and other search related notes dated Aug. 7, 2007 in U.S. Appl. No. 10/821,710, filed Apr. 8, 2004 by Graham et. al.
Examiner's search strategy and results dated Jul. 31, 2007 in U.S. Appl. No. 10/821,710, filed Apr. 8, 2004 by Graham et. al.
Amendment/Argument after Notice of Appeal dated Jul. 25, 2007 in U.S. Appl. No. 10/821,710, filed Apr. 8, 2004 by Graham et. al.
Advisory Action dated Jul. 20, 2007 in U.S. Appl. No. 10/821,710, filed Apr. 8, 2004 by Graham et. al.
List of References dated Jul. 20, 2007 in U.S. Appl. No. 10/821,710, filed Apr. 8, 2004 by Graham et. al.
Amendment After Final dated Jul. 12, 2007 in U.S. Appl. No. 10/821,710, filed Apr. 8, 2004 by Graham et. al.
Information Disclosure Statement dated Jul. 12, 2007 in U.S. Appl. No. 10/821,710, filed Apr. 8, 2004 by Graham et. al.
Amendment Copying Claims—Not in Response to Examiner Suggesting Claims dated Jul. 12, 2007 in U.S. Appl. No. 10/821,710, filed Apr. 8, 2004 by Graham et. al.

Third Party Submission after Publication under 37 CFR 1.99 after publication of a patent dated Mar. 6, 2007 in U.S. Appl. No. 10/821,710, filed Apr. 8, 2004 by Graham et. al.
Third Party Submission after Publication under 37 CFR 1.99 after publication of a patent dated Feb. 23, 2007 in U.S. Appl. No. 10/821,710, filed Apr. 8, 2004 by Graham et. al.
Final Rejection dated Jan. 12, 2007 in U.S. Appl. No. 10/821,710, filed Apr. 8, 2004 by Graham et. al.
List of references dated Jan. 12, 2007 in U.S. Appl. No. 10/821,710, filed Apr. 8, 2004 by Graham et. al.
Search information including classification, databases and other search related notes dated Jan. 12, 2007 in U.S. Appl. No. 10/821,710, filed Apr. 8, 2004 by Graham et. al.
Examiner's search strategy and results dated Jan. 5, 2007 in U.S. Appl. No. 10/821,710, filed Apr. 8, 2004 by Graham et. al.
Amendment/Req. Reconsideration—After Non-Final Reject dated Nov. 20, 2006 in U.S. Appl. No. 10/821,710, filed Apr. 8, 2004 by Graham et. al.
Examiner Interview Summary Record dated Nov. 6, 2006 in U.S. Appl. No. 10/821,710, filed Apr. 8, 2004 by Graham et. al.
Non-Final Rejection dated Jun. 19, 2006 in U.S. Appl. No. 10/821,710, filed Apr. 8, 2004 by Graham et. al.
List of References dated Jun. 19, 2006 in U.S. Appl. No. 10/821,710, filed Apr. 8, 2004 by Graham et. al.
Search information including classification, databases and other search related notes dated Jun. 19, 2006 in U.S. Appl. No. 10/821,710, filed Apr. 8, 2004 by Graham et. al.
Examiner's search strategy and results dated Jun. 13, 2006 in U.S. Appl. No. 10/821,710, filed Apr. 8, 2004 by Graham et. al.
Petition for review by the Office of Petitions. dated Jun. 12, 2006 in U.S. Appl. No. 10/821,710, filed Apr. 8, 2004 by Graham et. al.
Examiner's search strategy and results dated Jun. 12, 2006 in U.S. Appl. No. 10/821,710, filed Apr. 8, 2004 by Graham et. al.
Amendment Submitted/Entered with Filing of CPA/RCE dated Dec. 21, 2005 in U.S. Appl. No. 10/821,710, filed Apr. 8, 2004 by Graham et. al.
Information Disclosure Statement dated Dec. 21, 2005 in U.S. Appl. No. 10/821,710, filed Apr. 8, 2004 by Graham et. al.
Advisory Action dated Sep. 14, 2005 in U.S. Appl. No. 10/821,710, filed Apr. 8, 2004 by Graham et. al.
Amendment After Final dated Aug. 25, 2005 in U.S. Appl. No. 10/821,710, filed Apr. 8, 2004 by Graham et. al.
Information Disclosure Statement dated Jun. 30, 2005 in U.S. Appl. No. 10/821,710, filed Apr. 8, 2004 by Graham et. al.
Final Rejection dated Jun. 29, 2005 in U.S. Appl. No. 10/821,710, filed Apr. 8, 2004 by Graham et. al.
List of references dated Jun. 29, 2005 in U.S. Appl. No. 10/821,710, filed Apr. 8, 2004 by Graham et. al.
Search information including classification, databases and other search related notes dated Jun. 29, 2005 in U.S. Appl. No. 10/821,710, filed Apr. 8, 2004 by Graham et. al.
Examiner's search strategy and results dated Jun. 21, 2005 in U.S. Appl. No. 10/821,710, filed Apr. 8, 2004 by Graham et. al.
Amendment/Req. Reconsideration—After Non-Final Reject dated Apr. 29, 2005 in U.S. Appl. No. 10/821,710, filed Apr. 8, 2004 by Graham et. al.
Information Disclosure Statement dated Apr. 29, 2005 in U.S. Appl. No. 10/821,710, filed Apr. 8, 2004 by Graham et. al.
Information Disclosure Statement dated Feb. 25, 2005 in U.S. Appl. No. 10/821,710, filed Apr. 8, 2004 by Graham et. al.
Non-Final Rejection dated Feb. 11, 2005 in U.S. Appl. No. 10/821,710, filed Apr. 8, 2004 by Graham et. al.
Information Disclosure Statement dated Feb. 11, 2005 in U.S. Appl. No. 10/821,710, filed Apr. 8, 2004 by Graham et. al.
Non-Final Rejection dated Feb. 8, 2005 in U.S. Appl. No. 10/821,710, filed Apr. 8, 2004 by Graham et. al.
List of References dated Feb. 8, 2005 in U.S. Appl. No. 10/821,710, filed Apr. 8, 2004 by Graham et. al.
Search information including classification, databases and other search related notes dated Feb. 8, 2005 in U.S. Appl. No. 10/821,710, filed Apr. 8, 2004 by Graham et. al.
Examiner's search strategy and results dated Jan. 21, 2005 in U.S. Appl. No. 10/821,710, filed Apr. 8, 2004 by Graham et. al.

(56) References Cited

OTHER PUBLICATIONS

Response to Election / Restriction Filed dated Dec. 15, 2004 in U.S. Appl. No. 10/821,710, filed Apr. 8, 2004 by Graham et. al.
Claims dated Dec. 15, 2004 in U.S. Appl. No. 10/821,710, filed Apr. 8, 2004 by Graham et. al.
Requirement for Restriction/Election dated Oct. 15, 2004 in U.S. Appl. No. 10/821,710, filed Apr. 8, 2004 by Graham et. al.
Petition Decision dated Sep. 10, 2004 in U.S. Appl. No. 10/821,710, filed Apr. 8, 2004 by Graham et. al.
Information Disclosure Statement dated Aug. 2, 2004 in U.S. Appl. No. 10/821,710, filed Apr. 8, 2004 by Graham et. al.
Preliminary Amendment dated Jul. 23, 2004 in U.S. Appl. No. 10/821,710, filed Apr. 8, 2004 by Graham et. al.
Preliminary Amendment dated Apr. 8, 2004 in U.S. Appl. No. 10/821,710, filed Apr. 8, 2004 by Graham et. al.
U.S. Appl. No. 10/821,726, filed Apr. 8, 2004 by Graham et al.
Information Disclosure Statement dated May 8, 2009 in U.S. Appl. No. 10/821,726, filed Apr. 8, 2004 by Graham et. al.
Non-Final Rejection dated Nov. 3, 2008 in U.S. Appl. No. 10/821,726, filed Apr. 8, 2004 by Graham et. al.
List of references dated Nov. 3, 2008 in U.S. Appl. No. 10/821,726, filed Apr. 8, 2004 by Graham et. al.
Search information including classification, databases and other search related notes dated Nov. 3, 2008 in U.S. Appl. No. 10/821,726, filed Apr. 8, 2004 by Graham et. al.
Information Disclosure Statement dated Oct. 10, 2008 in U.S. Appl. No. 10/821,726, filed Apr. 8, 2004 by Graham et. al.
Amendment Submitted/Entered with Filing of CPA/RCE dated Sep. 8, 2008 in U.S. Appl. No. 10/821,726, filed Apr. 8, 2004 by Graham et. al.
Information Disclosure Statement dated Mar. 26, 2008 in U.S. Appl. No. 10/821,726, filed Apr. 8, 2004 by Graham et. al.
Protest Documents filed by 3rd Party dated Feb. 22, 2008 in U.S. Appl. No. 10/821,726, filed Apr. 8, 2004 by Graham et. al.
Information Disclosure Statement dated Jan. 28, 2008 in U.S. Appl. No. 10/821,726, filed Apr. 8, 2004 by Graham et. al.
Final Rejection dated Nov. 6, 2007 in U.S. Appl. No. 10/821,726, filed Apr. 8, 2004 by Graham et. al.
List of references dated Nov. 6, 2007 in U.S. Appl. No. 10/821,726, filed Apr. 8, 2004 by Graham et. al.
Search information including classification, databases and other search related notes dated Nov. 6, 2007 in U.S. Appl. No. 10/821,726, filed Apr. 8, 2004 by Graham et. al.
Amendment/Req. Reconsideration—After Non-Final Reject dated Nov. 2, 2007 in U.S. Appl. No. 10/821,726, filed Apr. 8, 2004 by Graham et. al.
Amendment/Req. Reconsideration—After Non-Final Reject dated Aug. 6, 2007 in U.S. Appl. No. 10/821,726, filed Apr. 8, 2004 by Graham et. al.
Third Party Submission after Publication under 37 CFR 1.99 after publication of a patent dated Feb. 23, 2007 in U.S. Appl. No. 10/821,726, filed Apr. 8, 2004 by Graham et. al.
Supplemental Response or Supplemental Amendment dated Dec. 14, 2006 in U.S. Appl. No. 10/821,726, filed Apr. 8, 2004 by Graham et. al.
Amendment/Req. Reconsideration—After Non-Final Reject dated Nov. 30, 2006 in U.S. Appl. No. 10/821,726, filed Apr. 8, 2004 by Graham et. al.
Petition Decision dated Oct. 10, 2006 in U.S. Appl. No. 10/821,726, filed Apr. 8, 2004 by Graham et. al.
Petition for review by the Office of Petitions. dated Jun. 12, 2006 in U.S. Appl. No. 10/821,726, filed Apr. 8, 2004 by Graham et. al.
Non-Final Rejection dated May 30, 2006 in U.S. Appl. No. 10/821,726, filed Apr. 8, 2004 by Graham et. al.
List of References dated May 30, 2006 in U.S. Appl. No. 10/821,726, filed Apr. 8, 2004 by Graham et. al.
Search information including classification, databases and other search related notes dated May 30, 2006 in U.S. Appl. No. 10/821,726, filed Apr. 8, 2004 by Graham et. al.
Examiner's search strategy and results dated May 19, 2006 in U.S. Appl. No. 10/821,726, filed Apr. 8, 2004 by Graham et. al.
Response to Election / Restriction Filed dated Nov. 18, 2005 in U.S. Appl. No. 10/821,726, filed Apr. 8, 2004 by Graham et. al.
Requirement for Restriction/Election dated Oct. 14, 2005 in U.S. Appl. No. 10/821,726, filed Apr. 8, 2004 by Graham et. al.
Information Disclosure Statement dated Jun. 30, 2005 in U.S. Appl. No. 10/821,726, filed Apr. 8, 2004 by Graham et. al.
Information Disclosure Statement dated Feb. 28, 2005 in U.S. Appl. No. 10/821,726, filed Apr. 8, 2004 by Graham et. al.
Information Disclosure Statement dated Feb. 11, 2005 in U.S. Appl. No. 10/821,726, filed Apr. 8, 2004 by Graham et. al.
Information Disclosure Statement dated Nov. 22, 2004 in U.S. Appl. No. 10/821,726, filed Apr. 8, 2004 by Graham et. al.
Petition Decision dated Sep. 30, 2004 in U.S. Appl. No. 10/821,726, filed Apr. 8, 2004 by Graham et. al.
Information Disclosure Statement dated Jul. 28, 2004 in U.S. Appl. No. 10/821,726, filed Apr. 8, 2004 by Graham et. al.
Petition Entered dated Jul. 28, 2004 in U.S. Appl. No. 10/821,726, filed Apr. 8, 2004 by Graham et. al.
Preliminary Amendment dated Apr. 8, 2004 in U.S. Appl. No. 10/821,726, filed Apr. 8, 2004 by Graham et. al.
U.S. Appl. No. 11/180,928, filed Jul. 13, 2005 by Graham et al.
Abandonment dated Apr. 29, 2009 in U.S. Appl. No. 11/180,928, filed Jul. 13, 2005 by Graham et. al.
Non-Final Rejection dated Sep. 2, 2008 in U.S. Appl. No. 11/180,928, filed Jul. 13, 2005 by Graham et. al.
List of References dated Sep. 2, 2008 in U.S. Appl. No. 11/180,928, filed Jul. 13, 2005 by Graham et. al.
Examiner's search strategy and results dated Sep. 2, 2008 in U.S. Appl. No. 11/180,928, filed Jul. 13, 2005 by Graham et. al.
Search information including classification, databases and other search related notes dated Sep. 2, 2008 in U.S. Appl. No. 11/180,928, filed Jul. 13, 2005 by Graham et. al.
Amendment/Req. Reconsideration—After Non-Final Reject dated Jun. 10, 2008 in U.S. Appl. No. 11/180,928, filed Jul. 13, 2005 by Graham et. al.
Information Disclosure Statement dated Jun. 10, 2008 in U.S. Appl. No. 11/180,928, filed Jul. 13, 2005 by Graham et. al.
Information Disclosure Statement dated Mar. 26, 2008 in U.S. Appl. No. 11/180,928, filed Jul. 13, 2005 by Graham et. al.
Information Disclosure Statement dated Jan. 30, 2008 in U.S. Appl. No. 11/180,928, filed Jul. 13, 2005 by Graham et. al.
Non-Final Rejection dated Jan. 8, 2008 in U.S. Appl. No. 11/180,928, filed Jul. 13, 2005 by Graham et. al.
Examiner Interview Summary Record dated Jan. 8, 2008 in U.S. Appl. No. 11/180,928, filed Jul. 13, 2005 by Graham et. al.
List of References dated Jan. 8, 2008 in U.S. Appl. No. 11/180,928, filed Jul. 13, 2005 by Graham et. al.
Search information including classification, databases and other search related notes dated Jan. 8, 2008 in U.S. Appl. No. 11/180,928, filed Jul. 13, 2005 by Graham et. al.
Examiner Interview Summary Record dated Dec. 11, 2007 in U.S. Appl. No. 11/180,928, filed Jul. 13, 2005 by Graham et. al.
Amendment/Req. Reconsideration—After Non-Final Reject dated Oct. 22, 2007 in U.S. Appl. No. 11/180,928, filed Jul. 13, 2005 by Graham et. al.
Rule 130, 131 or 132 Affidavits dated Oct. 22, 2007 in U.S. Appl. No. 11/180,928, filed Jul. 13, 2005 by Graham et. al.
Information Disclosure Statement dated Oct. 22, 2007 in U.S. Appl. No. 11/180,928, filed Jul. 13, 2005 by Graham et. al.
Non-Final Rejection dated Apr. 17, 2007 in U.S. Appl. No. 11/180,928, filed Jul. 13, 2005 by Graham et. al.
List of References dated Apr. 17, 2007 in U.S. Appl. No. 11/180,928, filed Jul. 13, 2005 by Graham et. al.
Search information including classification, databases and other search related notes dated Apr. 17, 2007 in U.S. Appl. No. 11/180,928, filed Jul. 13, 2005 by Graham et. al.
Examiner's search strategy and results dated Apr. 13, 2007 in U.S. Appl. No. 11/180,928, filed Jul. 13, 2005 by Graham et. al.
Response to Election / Restriction Filed dated Mar. 9, 2007 in U.S. Appl. No. 11/180,928, filed Jul. 13, 2005 by Graham et. al.

(56) References Cited

OTHER PUBLICATIONS

Requirement for Restriction/Election dated Feb. 6, 2007 in U.S. Appl. No. 11/180,928, filed Jul. 13, 2005 by Graham et. al.
Amendment/Req. Reconsideration—After Non-Final Reject dated Dec. 26, 2006 in U.S. Appl. No. 11/180,928, filed Jul. 13, 2005 by Graham et. al.
Information Disclosure Statement dated Dec. 26, 2006 in U.S. Appl. No. 11/180,928, filed Jul. 13, 2005 by Graham et. al.
Requirement for Restriction/Election dated Oct. 31, 2006 in U.S. Appl. No. 11/180,928, filed Jul. 13, 2005 by Graham et. al.
Preliminary Amendment dated Jul. 13, 2005 in U.S. Appl. No. 11/180,928, filed Jul. 13, 2005 by Graham et. al.
Information Disclosure Statement dated Jul. 13, 2005 in U.S. Appl. No. 11/180,928, filed Jul. 13, 2005 by Graham et. al.
U.S. Appl. No. 11/218,999, filed Sep. 2, 2005 by Graham et al.
Information Disclosure Statement dated Apr. 13, 2009 in U.S. Appl. No. 11/218,999, filed Sep. 2, 2005 by Graham et. al.
Information Disclosure Statement dated Apr. 3, 2009 in U.S. Appl. No. 11/218,999, filed Sep. 2, 2005 by Graham et. al.
Amendment/Req. Reconsideration—After Non-Final Reject dated Apr. 3, 2009 in U.S. Appl. No. 11/218,999, filed Sep. 2, 2005 by Graham et. al.
Non-Final Rejection dated Sep. 30, 2008 in U.S. Appl. No. 11/218,999, filed Sep. 2, 2005 by Graham et. al.
List of references dated Sep. 30, 2008 in U.S. Appl. No. 11/218,999, filed Sep. 2, 2005 by Graham et. al.
Search information including classification, databases and other search related notes dated Sep. 30, 2008 in U.S. Appl. No. 11/218,999, filed Sep. 2, 2005 by Graham et. al.
Examiner's search strategy and results dated Sep. 30, 2008 in U.S. Appl. No. 11/218,999, filed Sep. 2, 2005 by Graham et. al.
Amendment/Req. Reconsideration—After Non-Final Reject dated Jun. 19, 2008 in U.S. Appl. No. 11/218,999, filed Sep. 2, 2005 by Graham et. al.
Requirement for Restriction/Election dated May 21, 2008 in U.S. Appl. No. 11/218,999, filed Sep. 2, 2005 by Graham et. al.
Information Disclosure Statement dated Mar. 26, 2008 in U.S. Appl. No. 11/218,999, filed Sep. 2, 2005 by Graham et. al.
Response to Election / Restriction Filed dated Feb. 22, 2008 in U.S. Appl. No. 11/218,999, filed Sep. 2, 2005 by Graham et. al.
Protest Documents filed by 3rd Party dated Feb. 22, 2008 in U.S. Appl. No. 11/218,999, filed Sep. 2, 2005 by Graham et. al.
Information Disclosure Statement dated Jan. 30, 2008 in U.S. Appl. No. 11/218,999, filed Sep. 2, 2005 by Graham et. al.
Petition dated Nov. 2, 2007 in U.S. Appl. No. 11/218,999, filed Sep. 2, 2005 by Graham et. al.
Preliminary Amendment dated Nov. 2, 2007 in U.S. Appl. No. 11/218,999, filed Sep. 2, 2005 by Graham et. al.
Requirement for Restriction/Election dated Sep. 17, 2007 in U.S. Appl. No. 11/218,999, filed Sep. 2, 2005 by Graham et. al.
Preliminary Amendment dated Sep. 2, 2005 in U.S. Appl. No. 11/218,999, filed Sep. 2, 2005 by Graham et. al.
Information Disclosure Statement dated Sep. 2, 2005 in U.S. Appl. No. 11/218,999, filed Sep. 2, 2005 by Graham et. al.
U.S. Appl. No. 90/008,096, filed May 18, 2006 by Graham et al.
Reexam Petition Decision—Granted dated Apr. 25, 2009 in U.S. Appl. No. 90/008,096, filed May 18, 2006 by Graham et. al.
Reexam proceeding—Advisory Action dated Apr. 24, 2009 in U.S. Appl. No. 90/008,096, filed May 18, 2006 by Graham et. al.
Information Disclosure Statement dated Apr. 13, 2009 in U.S. Appl. No. 90/008,096, filed May 18, 2006 by Graham et. al.
Reexam proceeding—Advisory Action dated Mar. 25, 2009 in U.S. Appl. No. 90/008,096, filed May 18, 2006 by Graham et. al.
Amendment After Final dated Feb. 26, 2009 in U.S. Appl. No. 90/008,096, filed May 18, 2006 by Graham et. al.
Claim-Amendment Not Entered dated Feb. 26, 2009 in U.S. Appl. No. 90/008,096, filed May 18, 2006 by Graham et. al.
Applicant Arguments/Remarks Made in an Amendment dated Feb. 26, 2009 in U.S. Appl. No. 90/008,096, filed May 18, 2006 by Graham et. al.
Information Disclosure Statement dated Feb. 26, 2009 in U.S. Appl. No. 90/008,096, filed May 18, 2006 by Graham et. al.
Rule 130, 131 or 132 Affidavits dated Feb. 26, 2009 in U.S. Appl. No. 90/008,096, filed May 18, 2006 by Graham et. al.
Examiner Interview Summary Record dated Feb. 12, 2009 in U.S. Appl. No. 90/008,096, filed May 18, 2006 by Graham et. al.
Reexam—Final Rejection dated Nov. 26, 2008 in U.S. Appl. No. 90/008,096, filed May 18, 2006 by Graham et. al.
Reexam—Final Rejection dated Nov. 19, 2008 in U.S. Appl. No. 90/008,096, filed May 18, 2006 by Graham et. al.
List of References dated Nov. 19, 2008 in U.S. Appl. No. 90/008,096, filed May 18, 2006 by Graham et. al.
Search information including classification, databases and other search related notes dated Nov. 19, 2008 in U.S. Appl. No. 90/008,096, filed May 18, 2006 by Graham et. al.
Information Disclosure Statement dated Oct. 9, 2008 in U.S. Appl. No. 90/008,096, filed May 18, 2006 by Graham et. al.
Amendment/Req. Reconsideration—After Non-Final Reject dated Jul. 11, 2008 in U.S. Appl. No. 90/008,096, filed May 18, 2006 by Graham et. al.
Information Disclosure Statement dated Jul. 11, 2008 in U.S. Appl. No. 90/008,096, filed May 18, 2006 by Graham et. al.
Applicant Arguments/Remarks Made in an Amendment dated Jul. 11, 2008 in U.S. Appl. No. 90/008,096, filed May 18, 2006 by Graham et. al.
Examiner Interview Summary Record dated Jun. 12, 2008 in U.S. Appl. No. 90/008,096, filed May 18, 2006 by Graham et. al.
Reexam—Non-Final Action dated Apr. 11, 2008 in U.S. Appl. No. 90/008,096, filed May 18, 2006 by Graham et. al.
List of references dated Apr. 11, 2008 in U.S. Appl. No. 90/008,096, filed May 18, 2006 by Graham et. al.
Rule 130, 131 or 132 Affidavits dated Apr. 11, 2008 in U.S. Appl. No. 90/008,096, filed May 18, 2006 by Graham et. al.
Rule 130, 131 or 132 Affidavits dated Nov. 28, 2007 in U.S. Appl. No. 90/008,096, filed May 18, 2006 by Graham et. al.
Information Disclosure Statement dated Oct. 10, 2007 in U.S. Appl. No. 90/008,096, filed May 18, 2006 by Graham et. al.
Information Disclosure Statement dated Aug. 22, 2007 in U.S. Appl. No. 90/008,096, filed May 18, 2006 by Graham et. al.
Supplemental Response or Supplemental Amendment dated Aug. 3, 2007 in U.S. Appl. No. 90/008,096, filed May 18, 2006 by Graham et. al.
Examiner Interview Summary Record dated Jul. 6, 2007 in U.S. Appl. No. 90/008,096, filed May 18, 2006 by Graham et. al.
Amendment/Req. Reconsideration—After Non-Final Reject dated Apr. 24, 2007 in U.S. Appl. No. 90/008,096, filed May 18, 2006 by Graham et. al.
Information Disclosure Statement dated Apr. 24, 2007 in U.S. Appl. No. 90/008,096, filed May 18, 2006 by Graham et. al.
Examiner Interview Summary Record dated Mar. 2, 2007 in U.S. Appl. No. 90/008,096, filed May 18, 2006 by Graham et. al.
Reexam—Non-Final Action dated Jan. 24, 2007 in U.S. Appl. No. 90/008,096, filed May 18, 2006 by Graham et. al.
List of references dated Jan. 24, 2007 in U.S. Appl. No. 90/008,096, filed May 18, 2006 by Graham et. al.
Search information including classification, databases and other search related notes dated Jan. 24, 2007 in U.S. Appl. No. 90/008,096, filed May 18, 2006 by Graham et. al.
Amendment/Req. Reconsideration—After Non-Final Reject dated Nov. 27, 2006 in U.S. Appl. No. 90/008,096, filed May 18, 2006 by Graham et. al.
List of References dated Jul. 20, 2006 in U.S. Appl. No. 90/008,096, filed May 18, 2006 by Graham et. al.
List of References dated May 25, 2006 in U.S. Appl. No. 90/008,096, filed May 18, 2006 by Graham et. al.
Information Disclosure Statement dated May 18, 2006 in U.S. Appl. No. 90/008,096, filed May 18, 2006 by Graham et. al.
List of references dated Aug. 31, 2005 in U.S. Appl. No. 90/008,096, filed May 18, 2006 by Graham et. al.
U.S. Appl. No. 90/007,247, filed Oct. 4, 2004 by Graham et al.
Reexam proceeding—Advisory Action dated Apr. 24, 2009 in U.S. Appl. No. 90/007,247, filed Oct. 4, 2004 by Graham et. al.

(56) References Cited

OTHER PUBLICATIONS

Information Disclosure Statement dated Apr. 13, 2009 in U.S. Appl. No. 90/007,247, filed Oct. 4, 2004 by Graham et. al.
Reexam proceeding—Advisory Action dated Mar. 25, 2009 in U.S. Appl. No. 90/007,247, filed Oct. 4, 2004 by Graham et. al.
Amendment After Final dated Feb. 26, 2009 in U.S. Appl. No. 90/007,247, filed Oct. 4, 2004 by Graham et. al.
Information Disclosure Statement dated Feb. 26, 2009 in U.S. Appl. No. 90/007,247, filed Oct. 4, 2004 by Graham et. al.
Amendment/Req. Reconsideration—After Non-Final Reject dated Feb. 26, 2009 in U.S. Appl. No. 90/007,247, filed Oct. 4, 2004 by Graham et. al.
Reexam Certificate of Service dated Feb. 26, 2009 in U.S. Appl. No. 90/007,247, filed Oct. 4, 2004 by Graham et. al.
Examiner Interview Summary Record dated Feb. 12, 2009 in U.S. Appl. No. 90/007,247, filed Oct. 4, 2004 by Graham et. al.
Reexam—Final Rejection dated Nov. 19, 2008 in U.S. Appl. No. 90/007,247, filed Oct. 4, 2004 by Graham et. al.
List of References dated Nov. 19, 2008 in U.S. Appl. No. 90/007,247, filed Oct. 4, 2004 by Graham et. al.
Reexam Petition Decision—Granted dated Oct. 21, 2008 in U.S. Appl. No. 90/007,247, filed Oct. 4, 2004 by Graham et. al.
Information Disclosure Statement dated Oct. 9, 2008 in U.S. Appl. No. 90/007,247, filed Oct. 4, 2004 by Graham et. al.
Information Disclosure Statement dated Jul. 11, 2008 in U.S. Appl. No. 90/007,247, filed Oct. 4, 2004 by Graham et. al.
Amendment/Req. Reconsideration—After Non-Final Reject dated Jul. 11, 2008 in U.S. Appl. No. 90/007,247, filed Oct. 4, 2004 by Graham et. al.
Examiner Interview Summary Record dated Jun. 12, 2008 in U.S. Appl. No. 90/007,247, filed Oct. 4, 2004 by Graham et. al.
List of references dated Apr. 11, 2008 in U.S. Appl. No. 90/007,247, filed Oct. 4, 2004 by Graham et. al.
Search information including classification, databases and other search related notes dated Apr. 11, 2008 in U.S. Appl. No. 90/007,247, filed Oct. 4, 2004 by Graham et. al.
Preliminary Amendment dated Nov. 28, 2007 in U.S. Appl. No. 90/007,247, filed Oct. 4, 2004 by Graham et. al.
Rule 130, 131 or 132 Affidavits dated Nov. 28, 2007 in U.S. Appl. No. 90/007,247, filed Oct. 4, 2004 by Graham et. al.
Information Disclosure Statement dated Oct. 10, 2007 in U.S. Appl. No. 90/007,247, filed Oct. 4, 2004 by Graham et. al.
Information Disclosure Statement dated Aug. 22, 2007 in U.S. Appl. No. 90/007,247, filed Oct. 4, 2004 by Graham et. al.
Supplemental Response or Supplemental Amendment dated Aug. 3, 2007 in U.S. Appl. No. 90/007,247, filed Oct. 4, 2004 by Graham et. al.
Applicant Arguments/Remarks Made in an Amendment dated Aug. 3, 2007 in U.S. Appl. No. 90/007,247, filed Oct. 4, 2004 by Graham et. al.
Examiner Interview Summary Record dated Jul. 6, 2007 in U.S. Appl. No. 90/007,247, filed Oct. 4, 2004 by Graham et. al.
Amendment/Req. Reconsideration—After Non-Final Reject dated Apr. 24, 2007 in U.S. Appl. No. 90/007,247, filed Oct. 4, 2004 by Graham et. al.
Information Disclosure Statement dated Apr. 24, 2007 in U.S. Appl. No. 90/007,247, filed Oct. 4, 2004 by Graham et. al.
List of References dated Apr. 24, 2007 in U.S. Appl. No. 90/007,247, filed Oct. 4, 2004 by Graham et. al.
Rule 130, 131 or 132 Affidavits dated Apr. 24, 2007 in U.S. Appl. No. 90/007,247, filed Oct. 4, 2004 by Graham et. al.
Examiner Interview Summary Record dated Mar. 2, 2007 in U.S. Appl. No. 90/007,247, filed Oct. 4, 2004 by Graham et. al.
List of references dated Jan. 24, 2007 in U.S. Appl. No. 90/007,247, filed Oct. 4, 2004 by Graham et. al.
Search information including classification, databases and other search related notes dated Jan. 24, 2007 in U.S. Appl. No. 90/007,247, filed Oct. 4, 2004 by Graham et. al.
List of References dated Jul. 20, 2006 in U.S. Appl. No. 90/007,247, filed Oct. 4, 2004 by Graham et. al.
Transmittal of New Application dated Jun. 13, 2006 in U.S. Appl. No. 90/007,247, filed Oct. 4, 2004 by Graham et. al.
Reexam Certificate of Service dated Jun. 13, 2006 in U.S. Appl. No. 90/007,247, filed Oct. 4, 2004 by Graham et. al.
Transmittal of New Application dated Jun. 12, 2006 in U.S. Appl. No. 90/007,247, filed Oct. 4, 2004 by Graham et. al.
Amendment/Req. Reconsideration—After Non-Final Reject dated Jun. 12, 2006 in U.S. Appl. No. 90/007,247, filed Oct. 4, 2004 by Graham et. al.
Rule 130, 131 or 132 Affidavits dated Jun. 12, 2006 in U.S. Appl. No. 90/007,247, filed Oct. 4, 2004 by Graham et. al.
List of References dated May 25, 2006 in U.S. Appl. No. 90/007,247, filed Oct. 4, 2004 by Graham et. al.
List of References dated Apr. 13, 2006 in U.S. Appl. No. 90/007,247, filed Oct. 4, 2004 by Graham et. al.
Search information including classification, databases and other search related notes dated Apr. 13, 2006 in U.S. Appl. No. 90/007,247, filed Oct. 4, 2004 by Graham et. al.
Amendment/Req. Reconsideration—After Non-Final Reject dated Nov. 28, 2005 in U.S. Appl. No. 90/007,247, filed Oct. 4, 2004 by Graham et. al.
Rule 130, 131 or 132 Affidavits dated Nov. 28, 2005 in U.S. Appl. No. 90/007,247, filed Oct. 4, 2004 by Graham et. al.
Applicant summary of interview with examiner dated Nov. 28, 2005 in U.S. Appl. No. 90/007,247, filed Oct. 4, 2004 by Graham et. al.
Information Disclosure Statement dated Nov. 28, 2005 in U.S. Appl. No. 90/007,247, filed Oct. 4, 2004 by Graham et. al.
Examiner Interview Summary Record dated Oct. 25, 2005 in U.S. Appl. No. 90/007,247, filed Oct. 4, 2004 by Graham et. al.
Reexam—Non-Final Action dated Aug. 31, 2005 in U.S. Appl. No. 90/007,247, filed Oct. 4, 2004 by Graham et. al.
List of references dated Aug. 31, 2005 in U.S. Appl. No. 90/007,247, filed Oct. 4, 2004 by Graham et. al.
Search information including classification, databases and other search related notes dated Aug. 31, 2005 in U.S. Appl. No. 90/007,247, filed Oct. 4, 2004 by Graham et. al.
Information Disclosure Statement dated Jun. 30, 2005 in U.S. Appl. No. 90/007,247, filed Oct. 4, 2004 by Graham et. al.
Information Disclosure Statement dated Feb. 25, 2005 in U.S. Appl. No. 90/007,247, filed Oct. 4, 2004 by Graham et. al.
Information Disclosure Statement dated Feb. 7, 2005 in U.S. Appl. No. 90/007,247, filed Oct. 4, 2004 by Graham et. al.
Determination—Reexam Ordered dated Dec. 7, 2004 in U.S. Appl. No. 90/007,247, filed Oct. 4, 2004 by Graham et. al.
List of References dated Nov. 23, 2004 in U.S. Appl. No. 90/007,247, filed Oct. 4, 2004 by Graham et. al.
Notice of Assignment of Reexamination Request dated Oct. 19, 2004 in U.S. Appl. No. 90/007,247, filed Oct. 4, 2004 by Graham et. al.
Information Disclosure Statement dated Oct. 4, 2004 in U.S. Appl. No. 90/007,247, filed Oct. 4, 2004 by Graham et. al.
U.S. Appl. No. 09/215,257, filed Dec. 18, 1998 by Fire et al.
Examiner's search strategy and results dated Nov. 1, 2002 in U.S. Appl. No. 09/215,257, filed Dec. 18, 1998 by Fire et al.
Notice of Allowance dated Jul. 24, 2002 in U.S. Appl. No. 09/215,257, filed Dec. 18, 1998 by Fire et al.
Examiner Interview Summary Record dated Jun. 25, 2002 in U.S. Appl. No. 09/215,257, filed Dec. 18, 1998 by Fire et al.
Amendment/Req. Reconsideration—After Non-Final Reject dated Jun. 21, 2002 in U.S. Appl. No. 09/215,257, filed Dec. 18, 1998 by Fire et al.
Requirement for Restriction/Election dated May 21, 2002 in U.S. Appl. No. 09/215,257, filed Dec. 18, 1998 by Fire et al.
Examiner Interview Summary Record dated May 8, 2002 in U.S. Appl. No. 09/215,257, filed Dec. 18, 1998 by Fire et al.
Advisory Action dated Jan. 25, 2002 in U.S. Appl. No. 09/215,257, filed Dec. 18, 1998 by Fire et al.
List of References dated Jan. 25, 2002 in U.S. Appl. No. 09/215,257, filed Dec. 18, 1998 by Fire et al.
Examiner Interview Summary Record dated Jan. 25, 2002 in U.S. Appl. No. 09/215,257, filed Dec. 18, 1998 by Fire et al.

(56) References Cited

OTHER PUBLICATIONS

Amendment/Req. Reconsideration—After Non-Final Reject dated Jan. 8, 2002 in U.S. Appl. No. 09/215,257, filed Dec. 18, 1998 by Fire et al.
Examiner's search strategy and results dated Dec. 3, 2001 in U.S. Appl. No. 09/215,257, filed Dec. 18, 1998 by Fire et al.
Final Rejection dated Oct. 19, 2001 in U.S. Appl. No. 09/215,257, filed Dec. 18, 1998 by Fire et al.
List of references dated Oct. 19, 2001 in U.S. Appl. No. 09/215,257, filed Dec. 18, 1998 by Fire et al.
Amendment/Req. Reconsideration—After Non-Final Reject dated Aug. 14, 2001 in U.S. Appl. No. 09/215,257, filed Dec. 18, 1998 by Fire et al.
Non-Final Rejection dated Feb. 14, 2001 in U.S. Appl. No. 09/215,257, filed Dec. 18, 1998 by Fire et al.
List of references dated Feb. 14, 2001 in U.S. Appl. No. 09/215,257, filed Dec. 18, 1998 by Fire et al.
Examiner's search strategy and results dated Feb. 9, 2001 in U.S. Appl. No. 09/215,257, filed Dec. 18, 1998 by Fire et al.
Examiner's search strategy and results dated Jan. 30, 2001 in U.S. Appl. No. 09/215,257, filed Dec. 18, 1998 by Fire et al.
Information Disclosure Statement dated Jan. 22, 2001 in U.S. Appl. No. 09/215,257, filed Dec. 18, 1998 by Fire et al.
Examiner's search strategy and results dated Jan. 8, 2001 in U.S. Appl. No. 09/215,257, filed Dec. 18, 1998 by Fire et al.
Amendment/Req. Reconsideration—After Non-Final Reject dated Dec. 4, 2000 in U.S. Appl. No. 09/215,257, filed Dec. 18, 1998 by Fire et al.
Information Disclosure Statement dated Dec. 1, 2000 in U.S. Appl. No. 09/215,257, filed Dec. 18, 1998 by Fire et al.
Non-Final Rejection dated Jun. 2, 2000 in U.S. Appl. No. 09/215,257, filed Dec. 18, 1998 by Fire et al.
List of references dated Jun. 2, 2000 in U.S. Appl. No. 09/215,257, filed Dec. 18, 1998 by Fire et al.
Amendment/Req. Reconsideration—After Non-Final Reject dated Apr. 18, 2000 in U.S. Appl. No. 09/215,257, filed Dec. 18, 1998 by Fire et al.
Information Disclosure Statement dated Aug. 18, 2000 in U.S. Appl. No. 09/215,257, filed Dec. 18, 1998 by Fire et al.
Requirement for Restriction/Election dated Mar. 29, 2000 in U.S. Appl. No. 09/215,257, filed Dec. 18, 1998 by Fire et al.
Information Disclosure Statement dated Mar. 28, 2000 in U.S. Appl. No. 09/215,257, filed Dec. 18, 1998 by Fire et al.
Information Disclosure Statement dated Jan. 14, 2000 in U.S. Appl. No. 09/215,257, filed Dec. 18, 1998 by Fire et al.
Information Disclosure Statement dated Jul. 8, 1999 in U.S. Appl. No. 09/215,257, filed Dec. 18, 1998 by Fire et al.
Information Disclosure Statement dated Apr. 13, 1999 in U.S. Appl. No. 09/215,257, filed Dec. 18, 1998 by Fire et al.
Information Disclosure Statement dated Mar. 18, 1999 in U.S. Appl. No. 09/215,257, filed Dec. 18, 1998 by Fire et al.
U.S. Appl. No. 10/283,190, filed Oct. 30, 2002 by Fire et al.
Notice of Allowance dated Feb. 24, 2009 in U.S. Appl. No. 10/283,190, filed Oct. 30, 2002 by Fire et al.
Examiner's search strategy and results dated Feb. 24, 2009 in U.S. Appl. No. 10/283,190, filed Oct. 30, 2002 by Fire et al.
Search information including classification, databases and other search related notes dated Feb. 24, 2009 in U.S. Appl. No. 10/283,190, filed Oct. 30, 2002 by Fire et al.
List of References dated Jan. 28, 2008 in U.S. Appl. No. 10/283,190, filed Oct. 30, 2002 by Fire et al.
Notice of Allowance dated Oct. 22, 2007 in U.S. Appl. No. 10/283,190, filed Oct. 30, 2002 by Fire et al.
Issue Information including classification, examiner, name, claim, renumbering, etc. dated Oct. 22, 2007 in U.S. Appl. No. 10/283,190, filed Oct. 30, 2002 by Fire et al.
Search information including classification, databases and other search related notes dated Oct. 22, 2007 in U.S. Appl. No. 10/283,190, filed Oct. 30, 2002 by Fire et al.
Amendment After Final or under 37CFR 1.312, dated Oct. 22, 2007 in U.S. Appl. No. 10/283,190, filed Oct. 30, 2002 by Fire et al.
Notice of Appeal dated Oct. 18, 2007 in U.S. Appl. No. 10/283,190, filed Oct. 30, 2002 by Fire et al.
Amendment After Final dated Sep. 18, 2007 in U.S. Appl. No. 10/283,190, filed Oct. 30, 2002 by Fire et al.
Final Rejection dated Apr. 18, 2007 in U.S. Appl. No. 10/283,190, filed Oct. 30, 2002 by Fire et al.
List of References dated Apr. 18, 2007 in U.S. Appl. No. 10/283,190, filed Oct. 30, 2002 by Fire et al.
Search information including classification, databases and other search related notes dated Apr. 18, 2007 in U.S. Appl. No. 10/283,190, filed Oct. 30, 2002 by Fire et al.
Amendment/Req. Reconsideration—After Non-Final Reject dated Jan. 29, 2007 in U.S. Appl. No. 10/283,190, filed Oct. 30, 2002 by Fire et al.
Information Disclosure Statement dated Jan. 29, 2007 in U.S. Appl. No. 10/283,190, filed Oct. 30, 2002 by Fire et al.
Extension of Time dated Jan. 29, 2007 in U.S. Appl. No. 10/283,190, filed Oct. 30, 2002 by Fire et al.
Fee Worksheet dated Jan. 29, 2007 in U.S. Appl. No. 10/283,190, filed Oct. 30, 2002 by Fire et al.
Examiner Interview Summary Record dated Dec. 21, 2006 in U.S. Appl. No. 10/283,190, filed Oct. 30, 2002 by Fire et al.
Non-Final Rejection dated Jul. 28, 2006 in U.S. Appl. No. 10/283,190, filed Oct. 30, 2002 by Fire et al.
List of references dated Jul. 28, 2006 in U.S. Appl. No. 10/283,190, filed Oct. 30, 2002 by Fire et al.
Search information including classification, databases and other search related notes dated Jul. 28, 2006 in U.S. Appl. No. 10/283,190, filed Oct. 30, 2002 by Fire et al.
Amendment/Req. Reconsideration—After Non-Final Reject dated Apr. 27, 2006 in U.S. Appl. No. 10/283,190, filed Oct. 30, 2002 by Fire et al.
Non-Final Rejection dated Dec. 27, 2005 in U.S. Appl. No. 10/283,190, filed Oct. 30, 2002 by Fire et al.
List of references dated Dec. 27, 2005 in U.S. Appl. No. 10/283,190, filed Oct. 30, 2002 by Fire et al.
Amendment/Req. Reconsideration—After Non-Final Rejection dated Oct. 6, 2005 in U.S. Appl. No. 10/283,190, filed Oct. 30, 2002 by Fire et al.
Non-Final Rejection dated Apr. 11, 2005 in U.S. Appl. No. 10/283,190, filed Oct. 30, 2002 by Fire et al.
Examiner Interview Summary Record dated Apr. 11, 2005 in U.S. Appl. No. 10/283,190, filed Oct. 30, 2002 by Fire et al.
List of References dated Apr. 11, 2005 in U.S. Appl. No. 10/283,190, filed Oct. 30, 2002 by Fire et al.
Search information including classification, databases and other search related notes dated Apr. 11, 2005 in U.S. Appl. No. 10/283,190, filed Oct. 30, 2002 by Fire et al.
Examiner's search strategy and results dated Mar. 23, 2005 in U.S. Appl. No. 10/283,190, filed Oct. 30, 2002 by Fire et al.
Information Disclosure Statement dated Feb. 11, 2005 in U.S. Appl. No. 10/283,190, filed Oct. 30, 2002 by Fire et al.
Information Disclosure Statement dated Sep. 3, 2004 in U.S. Appl. No. 10/283,190, filed Oct. 30, 2002 by Fire et al.
Preliminary Amendment dated Jun. 25, 2004 in U.S. Appl. No. 10/283,190, filed Oct. 30, 2002 by Fire et al.
Information Disclosure Statement dated Jun. 25, 2004 in U.S. Appl. No. 10/283,190, filed Oct. 30, 2002 by Fire et al.
Examiner Interview Summary Record dated Apr. 14, 2004 in U.S. Appl. No. 10/283,190, filed Oct. 30, 2002 by Fire et al.
Information Disclosure Statement dated Dec. 31, 2003 in U.S. Appl. No. 10/283,190, filed Oct. 30, 2002 by Fire et al.
Information Disclosure Statement dated Mar. 7, 2003 in U.S. Appl. No. 10/283,190, filed Oct. 30, 2002 by Fire et al.
Preliminary Amendment dated Oct. 30, 2002 in U.S. Appl. No. 10/283,190, filed Oct. 30, 2002 by Fire et al.
U.S. Appl. No. 10/283,267, filed Oct. 30, 2002 by Fire et al.
Amendment After Final dated Jan. 10, 2008 in U.S. Appl. No. 10/283,267, filed Oct. 30, 2002 by Fire et al.
Final Rejection dated Dec. 3, 2007 in U.S. Appl. No. 10/283,267, filed Oct. 30, 2002 by Fire et al.

(56) References Cited

OTHER PUBLICATIONS

Search information including classification, databases and other search related notes dated Dec. 3, 2007 in U.S. Appl. No. 10/283,267, filed Oct. 30, 2002 by Fire et al.
Examiner's search strategy and results dated Nov. 29, 2007 in U.S. Appl. No. 10/283,267, filed Oct. 30, 2002 by Fire et al.
Amendment/Req. Reconsideration—After Non-Final Reject dated Sep. 17, 2007 in U.S. Appl. No. 10/283,267, filed Oct. 30, 2002 by Fire et al.
Non-Final Rejection dated May 15, 2007 in U.S. Appl. No. 10/283,267, filed Oct. 30, 2002 by Fire et al.
List of References dated May 15, 2007 in U.S. Appl. No. 10/283,267, filed Oct. 30, 2002 by Fire et al.
Search information including classification, databases and other search related notes dated May 15, 2007 in U.S. Appl. No. 10/283,267, filed Oct. 30, 2002 by Fire et al.
Examiner's search strategy and results dated May 7, 2007 in U.S. Appl. No. 10/283,267, filed Oct. 30, 2002 by Fire et al.
Amendment/Req. Reconsideration—After Non-Final Reject dated Feb. 12, 2007 in U.S. Appl. No. 10/283,267, filed Oct. 30, 2002 by Fire et al.
Information Disclosure Statement dated Feb. 12, 2007 in U.S. Appl. No. 10/283,267, filed Oct. 30, 2002 by Fire et al.
Non-Final Rejection dated Aug. 10, 2006 in U.S. Appl. No. 10/283,267, filed Oct. 30, 2002 by Fire et al.
List of references dated Aug. 10, 2006 in U.S. Appl. No. 10/283,267, filed Oct. 30, 2002 by Fire et al.
Search information including classification, databases and other search related notes dated Aug. 10, 2006 in U.S. Appl. No. 10/283,267, filed Oct. 30, 2002 by Fire et al.
Examiner's search strategy and results dated Aug. 1, 2006 in U.S. Appl. No. 10/283,267, filed Oct. 30, 2002 by Fire et al.
Amendment/Req. Reconsideration—After Non-Final Reject dated May 12, 2006 in U.S. Appl. No. 10/283,267, filed Oct. 30, 2002 by Fire et al.
Non-Final Rejection dated Jan. 12, 2006 in U.S. Appl. No. 10/283,267, filed Oct. 30, 2002 by Fire et al.
List of References dated Jan. 12, 2006 in U.S. Appl. No. 10/283,267, filed Oct. 30, 2002 by Fire et al.
Search information including classification, databases and other search related notes dated Jan. 12, 2006 in U.S. Appl. No. 10/283,267, filed Oct. 30, 2002 by Fire et al.
Examiner's search strategy and results dated Jan. 5, 2006 in U.S. Appl. No. 10/283,267, filed Oct. 30, 2002 by Fire et al.
Response to Election / Restriction Filed dated Oct. 24, 2005 in U.S. Appl. No. 10/283,267, filed Oct. 30, 2002 by Fire et al.
Requirement for Restriction/Election dated Sep. 23, 2005 in U.S. Appl. No. 10/283,267, filed Oct. 30, 2002 by Fire et al.
Information Disclosure Statement dated Feb. 11, 2005 in U.S. Appl. No. 10/283,267, filed Oct. 30, 2002 by Fire et al.
Information Disclosure Statement dated Sep. 3, 2004 in U.S. Appl. No. 10/283,267, filed Oct. 30, 2002 by Fire et al.
Examiner Interview Summary Record dated Apr. 15, 2004 in U.S. Appl. No. 10/283,267, filed Oct. 30, 2002 by Fire et al.
Information Disclosure Statement dated Dec. 31, 2003 in U.S. Appl. No. 10/283,267, filed Oct. 30, 2002 by Fire et al.
Information Disclosure Statement dated Mar. 7, 2003 in U.S. Appl. No. 10/283,267, filed Oct. 30, 2002 by Fire et al.
Preliminary Amendment dated Oct. 30, 2002 in U.S. Appl. No. 10/283,267, filed Oct. 30, 2002 by Fire et al.
U.S. Appl. No. 10/282,996, filed Oct. 30, 2002 by Fire et al.
Notice of Allowance dated Jan. 28, 2009 in U.S. Appl. No. 10/282,996, filed Oct. 30, 2002 by Fire et al.
Examiner's search strategy and results dated Jan. 28, 2009 in U.S. Appl. No. 10/282,996, filed Oct. 30, 2002 by Fire et al.
Search information including classification, databases and other search related notes dated Jan. 28, 2009 in U.S. Appl. No. 10/282,996, filed Oct. 30, 2002 by Fire et al.
List of References dated Oct. 29, 2007 in U.S. Appl. No. 10/282,996, filed Oct. 30, 2002 by Fire et al.
Search information including classification, databases and other search related notes dated Aug. 31, 2007 in U.S. Appl. No. 10/282,996, filed Oct. 30, 2002 by Fire et al.
Notice of Allowance dated Aug. 31, 2007 in U.S. Appl. No. 10/282,996, filed Oct. 30, 2002 by Fire et al.
Amendment After Final or under 37CFR 1.312, dated Aug. 31, 2007 in U.S. Appl. No. 10/282,996, filed Oct. 30, 2002 by Fire et al.
Examiner's search strategy and results dated Aug. 27, 2007 in U.S. Appl. No. 10/282,996, filed Oct. 30, 2002 by Fire et al.
Amendment After Final dated Aug. 8, 2007 in U.S. Appl. No. 10/282,996, filed Oct. 30, 2002 by Fire et al.
Final Rejection dated Jun. 21, 2007 in U.S. Appl. No. 10/282,996, filed Oct. 30, 2002 by Fire et al.
List of References dated Jun. 21, 2007 in U.S. Appl. No. 10/282,996, filed Oct. 30, 2002 by Fire et al.
Search information including classification, databases and other search related notes dated Jun. 21, 2007 in U.S. Appl. No. 10/282,996, filed Oct. 30, 2002 by Fire et al.
Amendment/Req. Reconsideration—After Non-Final Reject dated Mar. 27, 2007 in U.S. Appl. No. 10/282,996, filed Oct. 30, 2002 by Fire et al.
Information Disclosure Statement dated Mar. 27, 2007 in U.S. Appl. No. 10/282,996, filed Oct. 30, 2002 by Fire et al.
Non-Final Rejection dated Dec. 8, 2006 in U.S. Appl. No. 10/282,996, filed Oct. 30, 2002 by Fire et al.
Amendment/Argument after Notice of Appeal dated Oct. 25, 2006 in U.S. Appl. No. 10/282,996, filed Oct. 30, 2002 by Fire et al.
Claims dated Oct. 25, 2006 in U.S. Appl. No. 10/282,996, filed Oct. 30, 2002 by Fire et al.
Applicant Arguments/Remarks Made in an Amendment dated Oct. 25, 2006 in U.S. Appl. No. 10/282,996, filed Oct. 30, 2002 by Fire et al.
Advisory Action dated Aug. 14, 2006 in U.S. Appl. No. 10/282,996, filed Oct. 30, 2002 by Fire et al.
Amendment/Argument after Notice of Appeal dated Aug. 1, 2006 in U.S. Appl. No. 10/282,996, filed Oct. 30, 2002 by Fire et al.
Final Rejection dated Jan. 25, 2006 in U.S. Appl. No. 10/282,996, filed Oct. 30, 2002 by Fire et al.
Search information including classification, databases and other search related notes dated Jan. 25, 2006 in U.S. Appl. No. 10/282,996, filed Oct. 30, 2002 by Fire et al.
Amendment/Req. Reconsideration—After Non-Final Reject dated Nov. 4, 2005 in U.S. Appl. No. 10/282,996, filed Oct. 30, 2002 by Fire et al.
Non-Final Rejection dated May 4, 2005 in U.S. Appl. No. 10/282,996, filed Oct. 30, 2002 by Fire et al.
List of References dated May 4, 2005 in U.S. Appl. No. 10/282,996, filed Oct. 30, 2002 by Fire et al.
Search information including classification, databases and other search related notes dated May 4, 2005 in U.S. Appl. No. 10/282,996, filed Oct. 30, 2002 by Fire et al.
Examiner's search strategy and results dated Apr. 27, 2005 in U.S. Appl. No. 10/282,996, filed Oct. 30, 2002 by Fire et al.
Examiner's search strategy and results dated Apr. 21, 2005 in U.S. Appl. No. 10/282,996, filed Oct. 30, 2002 by Fire et al.
Response to Election / Restriction Filed dated Mar. 1, 2005 in U.S. Appl. No. 10/282,996, filed Oct. 30, 2002 by Fire et al.
Information Disclosure Statement dated Feb. 11, 2005 in U.S. Appl. No. 10/282,996, filed Oct. 30, 2002 by Fire et al.
Requirement for Restriction/Election dated Feb. 1, 2005 in U.S. Appl. No. 10/282,996, filed Oct. 30, 2002 by Fire et al.
Examiner Interview Summary Record dated Feb. 1, 2005 in U.S. Appl. No. 10/282,996, filed Oct. 30, 2002 by Fire et al.
Information Disclosure Statement dated Sep. 3, 2004 in U.S. Appl. No. 10/282,996, filed Oct. 30, 2002 by Fire et al.
Information Disclosure Statement dated Jun. 25, 2004 in U.S. Appl. No. 10/282,996, filed Oct. 30, 2002 by Fire et al.
Preliminary Amendment dated Jun. 2, 2004 in U.S. Appl. No. 10/282,996, filed Oct. 30, 2002 by Fire et al.
Information Disclosure Statement dated Jun. 2, 2004 in U.S. Appl. No. 10/282,996, filed Oct. 30, 2002 by Fire et al.
Examiner Interview Summary Record dated Apr. 15, 2004 in U.S. Appl. No. 10/282,996, filed Oct. 30, 2002 by Fire et al.

(56) References Cited

OTHER PUBLICATIONS

Information Disclosure Statement dated Dec. 31, 2003 in U.S. Appl. No. 10/282,996, filed Oct. 30, 2002 by Fire et al.
Information Disclosure Statement dated Mar. 7, 2003 in U.S. Appl. No. 10/282,996, filed Oct. 30, 2002 by Fire et al.
Preliminary Amendment dated Oct. 30, 2002 in U.S. Appl. No. 10/282,996, filed Oct. 30, 2002 by Fire et al.
U.S. Appl. No. 11/826,385, filed Jul. 13, 2007 by Fire et al.
Information Disclosure Statement dated Dec. 18, 2007 in U.S. Appl. No. 11/826,385, filed Jul. 13, 2007 by Fire et al.
Preliminary Amendment dated Sep. 26, 2007 in U.S. Appl. No. 11/826,385, filed Jul. 13, 2007 by Fire et al.
Preliminary Amendment dated Jul. 13, 2007 in U.S. Appl. No. 11/826,385, filed Jul. 13, 2007 by Fire et al.
U.S. Appl. No. 11/905,449, filed Oct. 1, 2007 by Fire et al.
Information Disclosure Statement dated Dec. 18, 2007 in U.S. Appl. No. 11/905,449, filed Oct. 1, 2007 by Fire et al.
Preliminary Amendment dated Oct. 1, 2007 in U.S. Appl. No. 11/905,449, filed Oct. 1, 2007 by Fire et al.
U.S. Appl. No. 11/905,368, filed Sep. 28, 2007 by Fire et al.
Information Disclosure Statement dated Dec. 18, 2007 in U.S. Appl. No. 11/905,368, filed Sep. 28, 2007 by Fire et al.
Preliminary Amendment dated Sep. 28, 2007 in U.S. Appl. No. 11/905,368, filed Sep. 28, 2007 by Fire et al.
Applicant Arguments/Remarks Made in an Amendment dated Sep. 28, 2007 in U.S. Appl. No. 11/905,368, filed Sep. 28, 2007 by Fire et al.
Third Party Observations filed Against European Patent Application EP 98964202.0 dated Mar. 24, 2009.
De Feyter et al., "A Ribozyme Gene and an Antisense Gene are Equally Effective in Conferring Resistance to Tobacco Mosaic Virus on Transgenic Tobacco", Mol. Gen. Genet., vol. 250, pp. 329-338, 1996.
Flavell, Proc. Natl. Acad. Sci., vol. 91, pp. 3490-3496 (1994).
Information Disclosure Statement (IDS) filed Apr. 27, 2010 in U.S. Appl. No. 09/287,632, filed Apr. 7, 1999 by Waterhouse et al.
Appeal Brief filed Apr. 8, 2010 in U.S. Appl. No. 09/287,632, filed Apr. 7, 1999 by Waterhouse et al.
Final Rejection filed Dec. 8, 2009 in U.S. Appl. No. 09/287,632, filed Apr. 7, 1999 by Waterhouse et al.
List of references filed Dec. 8, 2009 in U.S. Appl. No. 09/287,632, filed Apr. 7, 1999 by Waterhouse et al.
Search information including classification, databases and other search related notes filed Dec. 8, 2009 in U.S. Appl. No. 09/287,632, filed Apr. 7, 1999 by Waterhouse et al.
Amendment/Argument after Notice of Appeal filed Nov. 5, 2009 in U.S. Appl. No. 09/287,632, filed Apr. 7, 1999 by Waterhouse et al.
Information Disclosure Statement (IDS) filed Jun. 23, 2009 in U.S. Appl. No. 09/287,632, filed Apr. 7, 1999 by Waterhouse et al.
Information Disclosure Statement (IDS) filed Jun. 10, 2009 in U.S. Appl. No. 09/287,632, filed Apr. 7, 1999 by Waterhouse et al.
Information Disclosure Statement (IDS) filed May 22, 2009 in U.S. Appl. No. 09/287,632, filed Apr. 7, 1999 by Waterhouse et al.
Information Disclosure Statement (IDS) filed Jun. 23, 2009 in U.S. Appl. No. 11/607,062, filed Dec. 1, 2006 by Waterhouse et al.
Information Disclosure Statement (IDS) filed Jun. 10, 2009 in U.S. Appl. No. 11/607,062, filed Dec. 1, 2006 by Waterhouse et al.
Information Disclosure Statement (IDS) filed May 22, 2009 in U.S. Appl. No. 11/607,062, filed Dec. 1, 2006 by Waterhouse et al.
Final Rejection filed Apr. 23, 2010 in U.S. Appl. No. 11/841,737, filed Aug. 20, 2007 by Waterhouse et al.
List of references filed Apr. 23, 2010 in U.S. Appl. No. 11/841,737, filed Aug. 20, 2007 by Waterhouse et al.
Search information including classification, databases and other search related notes filed Apr. 23, 2010 in U.S. Appl. No. 11/841,737, filed Aug. 20, 2007 by Waterhouse et al.
Amendment/Req. Reconsideration—After Non-Final Reject filed Feb. 12, 2010 in U.S. Appl. No. 11/841,737, filed Aug. 20, 2007 by Waterhouse et al.
Information Disclosure Statement (IDS) filed Feb. 12, 2010 in U.S. Appl. No. 11/841,737, filed Aug. 20, 2007 by Waterhouse et al.
Non-Final Rejection filed Aug. 12, 2009 in U.S. Appl. No. 11/841,737, filed Aug. 20, 2007 by Waterhouse et al.
List of references filed Aug. 12, 2009 in U.S. Appl. No. 11/841,737, filed Aug. 20, 2007 by Waterhouse et al.
Search information including classification, databases and other search related notes filed Aug. 12, 2009 in U.S. Appl. No. 11/841,737, filed Aug. 20, 2007 by Waterhouse et al.
Examiner's search strategy and results filed Aug. 12, 2009 in U.S. Appl. No. 11/841,737, filed Aug. 20, 2007 by Waterhouse et al.
Response to Election / Restriction filed Jul. 6, 2009 in U.S. Appl. No. 11/841,737, filed Aug. 20, 2007 by Waterhouse et al.
Information Disclosure Statement (IDS) filed Jun. 23, 2009 in U.S. Appl. No. 11/841,737, filed Aug. 20, 2007 by Waterhouse et al.
Information Disclosure Statement (IDS) filed Jun. 10, 2009 in U.S. Appl. No. 11/841,737, filed Aug. 20, 2007 by Waterhouse et al.
Information Disclosure Statement (IDS) filed May 22, 2009 in U.S. Appl. No. 11/841,737, filed Aug. 20, 2007 by Waterhouse et al.
Final Rejection filed Mar. 24, 2010 in U.S. Appl. No. 11/593,056, filed Nov. 6, 2006 by Waterhouse et al.
Amendment/Req. Reconsideration—After Non-Final Reject filed Dec. 23, 2009 in U.S. Appl. No. 11/593,056, filed Nov. 6, 2006 by Waterhouse et al.
Non-Final Rejection filed Jun. 24, 2009 in U.S. Appl. No. 11/593,056, filed Nov. 6, 2006 by Waterhouse et al.
Search information including classification, databases and other search related notes filed Jun. 24, 2009 in U.S. Appl. No. 11/593,056, filed Nov. 6, 2006 by Waterhouse et al.
Amendment/Req. Reconsideration—After Non-Final Reject filed Mar. 12, 2009 in U.S. Appl. No. 11/593,056, filed Nov. 6, 2006 by Waterhouse et al.
Terminal Disclaimer filed Mar. 12, 2009 in U.S. Appl. No. 11/593,056, filed Nov. 6, 2006 by Waterhouse et al.
Non-Final Rejection filed Sep. 12, 2008 in U.S. Appl. No. 11/593,056, filed Nov. 6, 2006 by Waterhouse et al.
List of references filed Sep. 12, 2008 in U.S. Appl. No. 11/593,056, filed Nov. 6, 2006 by Waterhouse et al.
Search information including classification, databases and other search related notes filed Sep. 12, 2008 in U.S. Appl. No. 11/593,056, filed Nov. 6, 2006 by Waterhouse et al.
Amendment/Req. Reconsideration—After Non-Final Reject filed Jun. 12, 2008 in U.S. Appl. No. 11/593,056, filed Nov. 6, 2006 by Waterhouse et al.
Non-Final Rejection filed Dec. 12, 2007 in U.S. Appl. No. 11/593,056, filed Nov. 6, 2006 by Waterhouse et al.
List of References filed Dec. 12, 2007 in U.S. Appl. No. 11/593,056, filed Nov. 6, 2006 by Waterhouse et al.
Search information including classification, databases and other search related notes filed Dec. 12, 2007 in U.S. Appl. No. 11/593,056, filed Nov. 6, 2006 by Waterhouse et al.
Examiner's search strategy and results filed Dec. 4, 2007 in U.S. Appl. No. 11/593,056, filed Nov. 6, 2006 by Waterhouse et al.
Response to Election / Restriction filed Sep. 21, 2007 in U.S. Appl. No. 11/593,056, filed Nov. 6, 2006 by Waterhouse et al.
Requirement for Restriction/Election filed Jul. 24, 2007 in U.S. Appl. No. 11/593,056, filed Nov. 6, 2006 by Waterhouse et al.
Information Disclosure Statement (IDS) filed Mar. 8, 2007 in U.S. Appl. No. 11/593,056, filed Nov. 6, 2006 by Waterhouse et al.
Amendment Submitted/Entered with Filing of CPA/RCE filed Apr. 19, 2010 in U.S. Appl. No. 11/179,504, filed Jul. 13, 2005 by Waterhouse et al.
Advisory Action (PTOL-303) filed Feb. 16, 2010 in U.S. Appl. No. 11/179,504, filed Jul. 13, 2005 by Waterhouse et al.
Amendment After Final filed Feb. 3, 2010 in U.S. Appl. No. 11/179,504, filed Jul. 13, 2005 by Waterhouse et al.
Examiner Interview Summary Record (PTOL-413) filed Jan. 27, 2010 in U.S. Appl. No. 11/179,504, filed Jul. 13, 2005 by Waterhouse et al.
Final Rejection filed Aug. 13, 2009 in U.S. Appl. No. 11/179,504, filed Jul. 13, 2005 by Waterhouse et al.

(56) References Cited

OTHER PUBLICATIONS

Search information including classification, databases and other search related notes filed Aug. 13, 2009 in U.S. Appl. No. 11/179,504, filed Jul. 13, 2005 by Waterhouse et al.
List of References filed Aug. 13, 2009 in U.S. Appl. No. 11/179,504, filed Jul. 13, 2005 by Waterhouse et al.
Amendment/Req. Reconsideration—After Non-Final Reject filed May 15, 2009 in U.S. Appl. No. 11/179,504, filed Jul. 13, 2005 by Waterhouse et al.
Information Disclosure Statement (IDS) filed May 15, 2009 in U.S. Appl. No. 11/179,504, filed Jul. 13, 2005 by Waterhouse et al.
Non-Final Rejection filed Apr. 15, 2010 in U.S. Appl. No. 10/346,853, filed Jan. 17, 2003 by Graham et al.
List of References filed Apr. 15, 2010 in U.S. Appl. No. 10/346,853, filed Jan. 17, 2003 by Graham et al.
Search information including classification, databases and other search related notes filed Apr. 15, 2010 in U.S. Appl. No. 10/346,853, filed Jan. 17, 2003 by Graham et al.
Terminal Disclaimer Approval form used within the USPTO filed Jan. 17, 2010 in U.S. Appl. No. 10/346,853, filed Jan. 17, 2003 by Graham et al.
Supplemental Response or Supplemental Amendment filed Dec. 21, 2009 in U.S. Appl. No. 10/346,853, filed Jan. 17, 2003 by Graham et al.
Terminal Disclaimer filed Dec. 21, 2009 in U.S. Appl. No. 10/346,853, filed Jan. 17, 2003 by Graham et al.
Information Disclosure Statement (IDS) filed Dec. 21, 2009 in U.S. Appl. No. 10/346,853, filed Jan. 17, 2003 by Graham et al.
Rule 130, 131 or 132 Affidavits filed Dec. 21, 2009 in U.S. Appl. No. 10/346,853, filed Jan. 17, 2003 by Graham et al.
Examiner Interview Summary Record (PTOL-413) filed Dec. 9, 2009 in U.S. Appl. No. 10/346,853, filed Jan. 17, 2003 by Graham et al.
Amendment Submitted/Entered with Filing of CPA/RCE filed Oct. 19, 2009 in U.S. Appl. No. 10/346,853, filed Jan. 17, 2003 by Graham et al.
Application Data Sheet filed Oct. 19, 2009 in U.S. Appl. No. 10/346,853, filed Jan. 17, 2003 by Graham et al.
Rule 130, 131 or 132 Affidavits filed Oct. 19, 2009 in U.S. Appl. No. 10/346,853, filed Jan. 17, 2003 by Graham et al.
Information Disclosure Statement (IDS) filed Oct. 19, 2009 in U.S. Appl. No. 10/346,853, filed Jan. 17, 2003 by Graham et al.
Information Disclosure Statement (IDS) filed May 19, 2009 in U.S. Appl. No. 10/346,853, filed Jan. 17, 2003 by Graham et al.
Final Rejection filed May 15, 2009 in U.S. Appl. No. 10/346,853, filed Jan. 17, 2003 by Graham et al.
List of references filed May 15, 2009 in U.S. Appl. No. 10/346,853, filed Jan. 17, 2003 by Graham et al.
Search information including classification, databases and other search related notes filed May 15, 2009 in U.S. Appl. No. 10/346,853, filed Jan. 17, 2003 by Graham et al.
Petition decision filed May 8, 2009 in U.S. Appl. No. 10/346,853, filed Jan. 17, 2003 by Graham et al.
Information Disclosure Statement (IDS) filed Apr. 13, 2009 in U.S. Appl. No. 10/346,853, filed Jan. 17, 2003 by Graham et al.
Amendment After Final filed Jan. 12, 2009 in U.S. Appl. No. 10/346,853, filed Jan. 17, 2003 by Graham et al.
Information Disclosure Statement (IDS) filed Oct. 10, 2008 in U.S. Appl. No. 10/346,853, filed Jan. 17, 2003 by Graham et al.
Final Rejection filed Jul. 7, 2008 in U.S. Appl. No. 10/346,853, filed Jan. 17, 2003 by Graham et al.
List of references filed Jul. 7, 2008 in U.S. Appl. No. 10/346,853, filed Jan. 17, 2003 by Graham et al.
Search information including classification, databases and other search related notes filed Jul. 7, 2008 in U.S. Appl. No. 10/346,853, filed Jan. 17, 2003 by Graham et al.
Information Disclosure Statement (IDS) filed Jun. 4, 2008 in U.S. Appl. No. 10/346,853, filed Jan. 17, 2003 by Graham et al.
Response to Election / Restriction filed Apr. 21, 2008 in U.S. Appl. No. 10/346,853, filed Jan. 17, 2003 by Graham et al.
Information Disclosure Statement (IDS) filed Mar. 26, 2008 in U.S. Appl. No. 10/346,853, filed Jan. 17, 2003 by Graham et al.
Protest Documents filed by 3rd Party filed Feb. 22, 2008 in U.S. Appl. No. 10/346,853, filed Jan. 17, 2003 by Graham et al.
Information Disclosure Statement (IDS) filed Jan. 28, 2008 in U.S. Appl. No. 10/346,853, filed Jan. 17, 2003 by Graham et al.
Requirement for Restriction/Election filed Jan. 16, 2008 in U.S. Appl. No. 10/346,853, filed Jan. 17, 2003 by Graham et al.
Examiner Interview Summary Record (PTOL-413) filed Dec. 11, 2007 in U.S. Appl. No. 10/346,853, filed Jan. 17, 2003 by Graham et al.
Information Disclosure Statement (IDS) filed Oct. 17, 2007 in U.S. Appl. No. 10/346,853, filed Jan. 17, 2003 by Graham et al.
Amendment/Req. Reconsideration—After Non-Final Reject filed Oct. 17, 2007 in U.S. Appl. No. 10/346,853, filed Jan. 17, 2003 by Graham et al.
Rule 130, 131 or 132 Affidavits filed Oct. 17, 2007 in U.S. Appl. No. 10/346,853, filed Jan. 17, 2003 by Graham et al.
Non-Final Rejection filed Apr. 17, 2007 in U.S. Appl. No. 10/346,853, filed Jan. 17, 2003 by Graham et al.
List of References filed Apr. 17, 2007 in U.S. Appl. No. 10/346,853, filed Jan. 17, 2003 by Graham et al.
Search information including classification, databases and other search related notes filed Apr. 17, 2007 in U.S. Appl. No. 10/346,853, filed Jan. 17, 2003 by Graham et al.
Amendment/Req. Reconsideration—After Non-Final Reject filed Feb. 22, 2007 in U.S. Appl. No. 10/346,853, filed Jan. 17, 2003 by Graham et al.
Petition filed Dec. 28, 2006 in U.S. Appl. No. 10/346,853, filed Jan. 17, 2003 by Graham et al.
Information Disclosure Statement (IDS) filed Dec. 28, 2006 in U.S. Appl. No. 10/346,853, filed Jan. 17, 2003 by Graham et al.
Amendment/Req. Reconsideration—After Non-Final Reject filed Dec. 28, 2006 in U.S. Appl. No. 10/346,853, filed Jan. 17, 2003 by Graham et al.
Jan. 17, 2003 by Graham et al.
Petition Decision filed Oct. 10, 2006 in U.S. Appl. No. 10/346,853, filed Jan. 17, 2003 by Graham et al.
Non-Final Rejection filed Jun. 27, 2006 in U.S. Appl. No. 10/346,853, filed Jan. 17, 2003 by Graham et al.
List of References filed Jun. 27, 2006 in U.S. Appl. No. 10/346,853, filed Jan. 17, 2003 by Graham et al.
Search information including classification, databases and other search related notes filed Jun. 27, 2006 in U.S. Appl. No. 10/346,853, filed Jan. 17, 2003 by Graham et al.
Examiner's search strategy and results filed Jun. 20, 2006 in U.S. Appl. No. 10/346,853, filed Jan. 17, 2003 by Graham et al.
Petition filed Jun. 12, 2006 in U.S. Appl. No. 10/346,853, filed Jan. 17, 2003 by Graham et al.
Response to Election / Restriction filed Aug. 2, 2005 in U.S. Appl. No. 10/346,853, filed Jan. 17, 2003 by Graham et al.
Requirement for Restriction/Election filed Jul. 22, 2005 in U.S. Appl. No. 10/346,853, filed Jan. 17, 2003 by Graham et al.
Information Disclosure Statement (IDS) filed Jul. 1, 2005 in U.S. Appl. No. 10/346,853, filed Jan. 17, 2003 by Graham et al.
Information Disclosure Statement (IDS) filed Feb. 25, 2005 in U.S. Appl. No. 10/346,853, filed Jan. 17, 2003 by Graham et al.
Information Disclosure Statement (IDS) filed Feb. 11, 2005 in U.S. Appl. No. 10/346,853, filed Jan. 17, 2003 by Graham et al.
Information Disclosure Statement (IDS) filed Dec. 9, 2004 in U.S. Appl. No. 10/346,853, filed Jan. 17, 2003 by Graham et al.
Petition Decision filed Sep. 22, 2004 in U.S. Appl. No. 10/346,853, filed Jan. 17, 2003 by Graham et al.
Information Disclosure Statement (IDS) filed Jul. 30, 2004 in U.S. Appl. No. 10/346,853, filed Jan. 17, 2003 by Graham et al.
Petition filed Jul. 27, 2004 in U.S. Appl. No. 10/346,853, filed Jan. 17, 2003 by Graham et al.
Information Disclosure Statement (IDS) filed Jan. 20, 2004 in U.S. Appl. No. 10/346,853, filed Jan. 17, 2003 by Graham et al.
Information Disclosure Statement (IDS) filed Sep. 22, 2003 in U.S. Appl. No. 10/346,853, filed Jan. 17, 2003 by Graham et al.
Information Disclosure Statement (IDS) filed Jul. 7, 2003 in U.S. Appl. No. 10/346,853, filed Jan. 17, 2003 by Graham et al.

(56) References Cited

OTHER PUBLICATIONS

Information Disclosure Statement (IDS) filed Jun. 20, 2003 in U.S. Appl. No. 10/346,853, filed Jan. 17, 2003 by Graham et al.
Preliminary Amendment filed Mar. 31, 2003 in U.S. Appl. No. 10/346,853, filed Jan. 17, 2003 by Graham et al.
Information Disclosure Staement (IDS) filed Apr. 29, 2010 in U.S. Appl. No. 10/646,070, filed Aug. 22, 2003 by Graham et al.
Notice of Allowance and Fees Due (PTOL-85) filed Jan. 27, 2010 in U.S. Appl. No. 10/646,070, filed Aug. 22, 2003 by Graham et al.
Search information including classification, databases and other search related notes filed Jan. 27, 2010 in U.S. Appl. No. 10/646,070, filed Aug. 22, 2003 by Graham et al.
Examiner's search strategy and results filed Jan. 27, 2010 in U.S. Appl. No. 10/646,070, filed Aug. 22, 2003 by Graham et al.
List of References filed Jan. 27, 2010 in U.S. Appl. No. 10/646,070, filed Aug. 22, 2003 by Graham et al.
Terminal Disclaimer filed Dec. 14, 2009 in U.S. Appl. No. 10/646,070, filed Aug. 22, 2003 by Graham et al.
Terminal Disclaimer filed Nov. 12, 2009 in U.S. Appl. No. 10/646,070, filed Aug. 22, 2003 by Graham et al.
Information Disclosure Staement (IDS) filed Jul. 17, 2009 in U.S. Appl. No. 10/646,070, filed Aug. 22, 2003 by Graham et al.
Amendment/Req. Reconsideration—After Non-Final Reject filed Jul. 17, 2009 in U.S. Appl. No. 10/646,070, filed Aug. 22, 2003 by Graham et al.
Non-Final Rejection filed Jun. 9, 2009 in U.S. Appl. No. 10/646,070, filed Aug. 22, 2003 by Graham et al.
List of references filed Jun. 9, 2009 in U.S. Appl. No. 10/646,070, filed Aug. 22, 2003 by Graham et al.
Search information including classification, databases and other search related notes filed Jun. 9, 2009 in U.S. Appl. No. 10/646,070, filed Aug. 22, 2003 by Graham et al.
Petition Decision filed May 19, 2009 in U.S. Appl. No. 10/646,070, filed Aug. 22, 2003 by Graham et al.
Amendment Submitted/Entered with Filing of CPA/RCE filed May 15, 2009 in U.S. Appl. No. 10/646,070, filed Aug. 22, 2003 by Graham et al.
Information Disclosure Statement (IDS) filed May 15, 2009 in U.S. Appl. No. 10/646,070, filed Aug. 22, 2003 by Graham et al.
Examiner Interview Summary Record (PTOL-413) filed Apr. 15, 2010 in U.S. Appl. No. 10/759,841, filed Jan. 15, 2004 by Graham et al.
Non-Final Rejection filed Mar. 9, 2010 in U.S. Appl. No. 10/759,841, filed Jan. 15, 2004 by Graham et al.
List of references filed Mar. 9, 2010 in U.S. Appl. No. 10/759,841, filed Jan. 15, 2004 by Graham et al.
Search information including classification, databases and other search related notes filed Mar. 9, 2010 in U.S. Appl. No. 10/759,841, filed Jan. 15, 2004 by Graham et al.
Transmittal Letter filed Dec. 21, 2009 in U.S. Appl. No. 10/759,841, filed Jan. 15, 2004 by Graham et al.
Supplemental Response or Supplemental Amendment filed Dec. 21, 2009 in U.S. Appl. No. 10/759,841, filed Jan. 15, 2004 by Graham et al.
Terminal Disclaimer filed Dec. 21, 2009 in U.S. Appl. No. 10/759,841, filed Jan. 15, 2004 by Graham et al.
Information Disclosure Statement (IDS) filed Dec. 21, 2009 in U.S. Appl. No. 10/759,841, filed Jan. 15, 2004 by Graham et al.
Information Disclosure Statement (IDS) filed Oct. 2, 2009 in U.S. Appl. No. 10/759,841, filed Jan. 15, 2004 by Graham et al.
Amendment Submitted/Entered with Filing of CPA/RCE filed Sep. 28, 2009 in U.S. Appl. No. 10/759,841, filed Jan. 15, 2004 by Graham et al.
Rule 130, 131 or 132 Affidavits filed Sep. 28, 2009 in U.S. Appl. No. 10/759,841, filed Jan. 15, 2004 by Graham et al.
Information Disclosure Statement (IDS) filed Sep. 28, 2009 in U.S. Appl. No. 10/759,841, filed Jan. 15, 2004 by Graham et al.
Final Rejection filed Mar. 9, 2010 in U.S. Appl. No. 10/821,726, filed Apr. 8, 2004 by Graham et al.
List of references filed Mar. 9, 2010 in U.S. Appl. No. 10/821,726, filed Apr. 8, 2004 by Graham et al.
Search information including classification, databases and other search related notes filed Mar. 9, 2010 in U.S. Appl. No. 10/821,726, filed Apr. 8, 2004 by Graham et al.
Supplemental Response or Supplemental Amendment filed Oct. 13, 2009 in U.S. Appl. No. 10/821,726, filed Apr. 8, 2004 by Graham et al.
Rule 130, 131 or 132 Affidavits filed Oct. 13, 2009 in U.S. Appl. No. 10/821,726, filed Apr. 8, 2004 by Graham et al.
Information Disclosure Statement (IDS) filed Oct. 13, 2009 in U.S. Appl. No. 10/821,726, filed Apr. 8, 2004 by Graham et al.
Amendment/Req. Reconsideration—After Non-Final Reject filed Oct. 7, 2009 in U.S. Appl. No. 10/821,726, filed Apr. 8, 2004 by Graham et al.
Non-Final Rejection filed Apr. 21, 2010 in U.S. Appl. No. 11/218,999, filed Sep. 2, 2005 by Graham et al.
List of references filed Apr. 21, 2010 in U.S. Appl. No. 11/218,999, filed Sep. 2, 2005 by Graham et al.
Search information including classification, databases and other search related notes filed Apr. 21, 2010 in U.S. Appl. No. 11/218,999, filed Sep. 2, 2005 by Graham et al.
Amendment Submitted/Entered with Filing of CPA/RCE filed Mar. 12, 2010 in U.S. Appl. No. 11/218,999, filed Sep. 2, 2005 by Graham et al.
Information Disclosure Statement (IDS) filed Mar. 12, 2010 in U.S. Appl. No. 11/218,999, filed Sep. 2, 2005 by Graham et al.
Final Rejection filed Oct. 9, 2009 in U.S. Appl. No. 11/218,999, filed Sep. 2, 2005 by Graham et al.
List of references filed Oct. 9, 2009 in U.S. Appl. No. 11/218,999, filed Sep. 2, 2005 by Graham et al.
Search information including classification, databases and other search related notes filed Oct. 9, 2009 in U.S. Appl. No. 11/218,999, filed Sep. 2, 2005 by Graham et al.
Amendment/Req. Reconsideration—After Non-Final Reject filed Aug. 7, 2009 in U.S. Appl. No. 11/218,999, filed Sep. 2, 2005 by Graham et al.
Rule 130, 131 or 132 Affidavits filed Aug. 7, 2009 in U.S. Appl. No. 11/218,999, filed Sep. 2, 2005 by Graham et al.
Response to Election / Restriction filed Jun. 26, 2009 in U.S. Appl. No. 11/218,999, filed Sep. 2, 2005 by Graham et al.
Information Disclosure Statement (IDS) filed May 19, 2009 in U.S. Appl. No. 11/218,999, filed Sep. 2, 2005 by Graham et al.
Information Disclosure Statement (IDS) filed Apr. 13, 2009 in U.S. Appl. No. 11/218,999, filed Sep. 2, 2005 by Graham et al.
Information Disclosure Statement (IDS) filed Apr. 3, 2009 in U.S. Appl. No. 11/218,999, filed Sep. 2, 2005 by Graham et al.
Amendment/Req. Reconsideration—After Non-Final Reject filed Apr. 3, 2009 in U.S. Appl. No. 11/218,999, filed Sep. 2, 2005 by Graham et al.
Non-Final Rejection filed Sep. 30, 2008 in U.S. Appl. No. 11/218,999, filed Sep. 2, 2005 by Graham et al.
List of references filed Sep. 30, 2008 in U.S. Appl. No. 11/218,999, filed Sep. 2, 2005 by Graham et al.
Search information including classification, databases and other search related notes filed Sep. 30, 2008 in U.S. Appl. No. 11/218,999, filed Sep. 2, 2005 by Graham et al.
Examiner's search strategy and results filed Sep. 30, 2008 in U.S. Appl. No. 11/218,999, filed Sep. 2, 2005 by Graham et al.
Amendment/Req. Reconsideration—After Non-Final Reject filed Jun. 19, 2008 in U.S. Appl. No. 11/218,999, filed Sep. 2, 2005 by Graham et al.
List of References filed Mar. 26, 2010 in U.S. Appl. No. 90/008,096, filed May 18, 2006 by Graham et al.
Information Disclosure Statement (IDS) filed Mar. 10, 2010 in U.S. Appl. No. 90/008,096, filed May 18, 2006 by Graham et al.
Reply Brief filed Mar. 8, 2010 in U.S. Appl. No. 90/008,096, filed May 18, 2006 by Graham et al.
List of References filed Jan. 15, 2010 in U.S. Appl. No. 90/008,096, filed May 18, 2006 by Graham et al.
List of References filed Jan. 13, 2010 in U.S. Appl. No. 90/008,096, filed May 18, 2006 by Graham et al.

(56) References Cited

OTHER PUBLICATIONS

Examiner's Answer to Appeal Brief filed Jan. 7, 2010 in U.S. Appl. No. 90/008,096, filed May 18, 2006 by Graham et al.
Appeal Brief filed Nov. 2, 2009 in U.S. Appl. No. 90/008,096, filed May 18, 2006 by Graham et al.
Information Disclosure Statement (IDS) filed Jul. 30, 2009 in U.S. Appl. No. 90/008,096, filed May 18, 2006 by Graham et al.
Appeal Brief filed Jul. 27, 2009 in U.S. Appl. No. 90/008,096, filed May 18, 2006 by Graham et al.
Information Disclosure Statement (IDS) filed May 19, 2009 in U.S. Appl. No. 90/008,096, filed May 18, 2006 by Graham et al.
List of References filed Mar. 26, 2010 in U.S. Appl. No. 90/007,247, filed Oct. 4, 2004 by Graham et al.
Information Disclosure Statement (IDS) filed Mar. 10, 2010 in U.S. Appl. No. 90/007,247, filed Oct. 4, 2004 by Graham et al.
Reply Brief filed Mar. 8, 2010 in U.S. Appl. No. 90/007,247, filed Oct. 4, 2004 by Graham et al.
List of References filed Jan. 15, 2010 in U.S. Appl. No. 90/007,247, filed Oct. 4, 2004 by Graham et al.
List of References filed Jan. 13, 2010 in U.S. Appl. No. 90/007,247, filed Oct. 4, 2004 by Graham et al.
Examiner's Answer to Appeal Brief filed Jan. 7, 2010 in U.S. Appl. No. 90/007,247, filed Oct. 4, 2004 by Graham et al.
Amendment After Final or under 37CFR 1.312 filed Jan. 7, 2010 in U.S. Appl. No. 90/007,247, filed Oct. 4, 2004 by Graham et al.
Appeal Brief filed Nov. 2, 2009 in U.S. Appl. No. 90/007,247, filed Oct. 4, 2004 by Graham et al.
Information Disclosure Statement (IDS) filed Jul. 30, 2009 in U.S. Appl. No. 90/007,247, filed Oct. 4, 2004 by Graham et al.
Appeal Brief filed Jul. 27, 2009 in U.S. Appl. No. 90/007,247, filed Oct. 4, 2004 by Graham et al.
Information Disclosure Statement (IDS) filed May 19, 2009 in U.S. Appl. No. 90/007,247, filed Oct. 4, 2004 by Graham et al.
List of References filed Sep. 30, 2009 in U.S. Appl. No. 10/283,267, filed Oct. 30, 2002 by Fire et al.
Information Disclosure Statement (IDS) filed Sep. 28, 2009 in U.S. Appl. No. 10/283,267, filed Oct. 30, 2002 by Fire et al.
Information Disclosure Statement (IDS) filed Sep. 24, 2009 in U.S. Appl. No. 10/283,267, filed Oct. 30, 2002 by Fire et al.
Notice of Allowance filed Jun. 26, 2009 in U.S. Appl. No. 10/283,267, filed Oct. 30, 2002 by Fire et al.
Non-Final Rejection filed Apr. 9, 2010 in U.S. Appl. No. 11/826,385, filed Jul. 13, 2007 by Fire et al.
Search information including classification, databases and other search related notes filed Apr. 9, 2010 in U.S. Appl. No. 11/826,385, filed Jul. 13, 2007 by Fire et al.
Examiner's search strategy and results filed Apr. 9, 2010 in U.S. Appl. No. 11/826,385, filed Jul. 13, 2007 by Fire et al.
List of References filed Apr. 9, 2010 in U.S. Appl. No. 11/826,385, filed Jul. 13, 2007 by Fire et al.
Response to Election / Restriction filed Nov. 5, 2009 in U.S. Appl. No. 11/826,385, filed Jul. 13, 2007 by Fire et al.
Requirement for Restriction/Election filed Oct. 5, 2009 in U.S. Appl. No. 11/826,385, filed Jul. 13, 2007 by Fire et al.
Information Disclosure Statement (IDS) filed Jun. 10, 2009 in U.S. Appl. No. 11/826,385, filed Jul. 13, 2007 by Fire et al.
Non-Final Rejection filed Apr. 2, 2010 in U.S. Appl. No. 11/905,449, filed Oct. 1, 2007 by Fire et al.
Search information including classification, databases and other search related notes filed Apr. 2, 2010 in U.S. Appl. No. 11/905,449, filed Oct. 1, 2007 by Fire et al.
List of References filed Apr. 2, 2010 in U.S. Appl. No. 11/905,449, filed Oct. 1, 2007 by Fire et al.
Examiner's search strategy and results filed Apr. 2, 2010 in U.S. Appl. No. 11/905,449, filed Oct. 1, 2007 by Fire et al.
Information Disclosure Statement (IDS) filed Jun. 10, 2009 in U.S. Appl. No. 11/905,449, filed Oct. 1, 2007 by Fire et al.
Response to Election / Restriction filed May 7, 2010 in U.S. Appl. No. 11/905,368, filed Sep. 28, 2007 by Fire et al.
Requirement for Restriction/Election filed Mar. 24, 2010 in U.S. Appl. No. 11/905,368, filed Sep. 28, 2007 by Fire et al.
Information Disclosure Statement (IDS) filed Jun. 10, 2009 in U.S. Appl. No. 11/905,368, filed Sep. 28, 2007 by Fire et al.

* cited by examiner

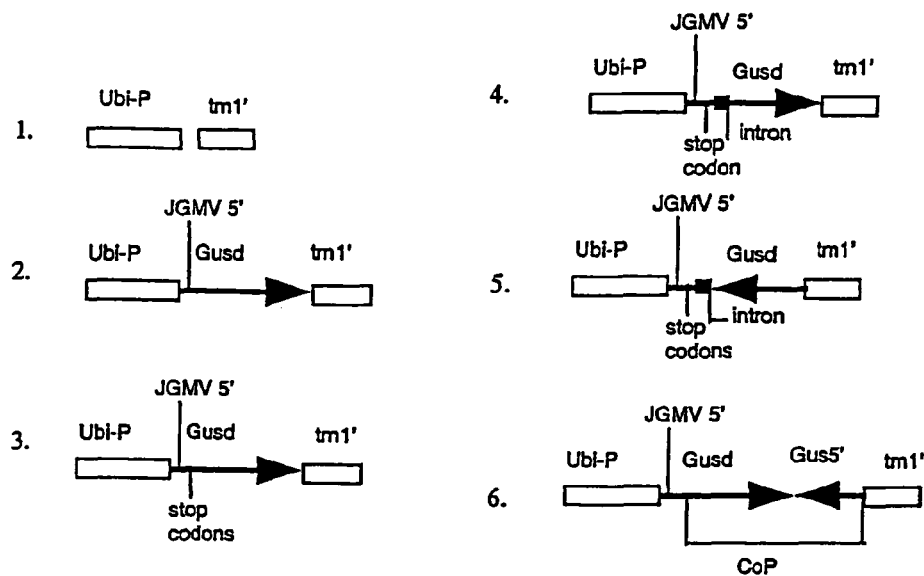
Figure 1A: Schematic representation of the chimeric genes used in Example 1
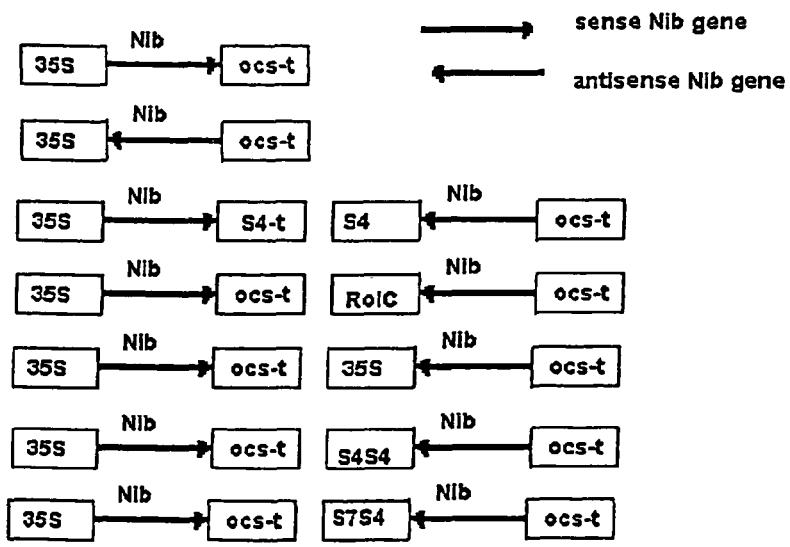
Figure 1B: Schematic representation of the chimeric genes used in Examples 2 and 4

METHODS AND MEANS FOR OBTAINING MODIFIED PHENOTYPES

CROSS-REFERENCE TO RELATED APPLICATIONS

This application is a continuation of U.S. application Ser. No. 10/755,328, filed Jan. 13, 2004, which is a continuation of U.S. application Ser. No. 09/287,632, filed Apr. 7, 1999, which claims the benefit of Provisional Application No. 60/198,254, filed Aug. 3, 1998 and Provisional Application No. 60/198,240, filed Apr. 8, 1998. The contents of each of these applications are hereby incorporated by reference in their entirety for all purposes.

FIELD OF THE INVENTION

The invention relates to methods for reducing the phenotypic expression of a nucleic acid sequence of interest in eucaryotic cells, particularly plant cells, by simultaneously providing the cells with chimeric genes encoding sense and anti sense RNA molecules comprising nucleotide sequences respectively homologous and complementary to at least part of the nucleotide sequence of the nucleic acid of interest. The sense and antisense RNA molecules may be provided as one RNA molecule, wherein the sense and antisense RNA may be linked by a spacer nucleotide sequence and are capable of forming a double stranded RNA molecule. In one aspect of the invention, the methods are directed towards reducing viral infection, resulting in extreme virus resistance. In another embodiment the methods are directed towards reducing the phenotypic expression of an endogenous gene in a plant cell. The invention further relates to high throughput screening methods for identifying the phenotype endowed by the nucleic acid of interest in plant cells. Also provided are plant cells comprising such RNA molecules, as well as plants consisting essentially of such plant cells.

BACKGROUND OF THE INVENTION

In 1985, Sanford and Johnston proposed the concept of parasite-derived resistance. They postulated that key gene products from a parasite expressed in the host in a dysfunctional form, in excess or at a wrong developmental stage, should disrupt the function of the parasite with minimal effect on the host (Sanford & Johnston, 1985). Using the QB bacteriophage as a model, they proposed that expression, in bacteria, of the bacteriophage coat protein or modified replicase or an antisense RNA complementary to the QB genome could all give resistance. They also proposed that such approaches would be applicable, in plants, to plant viruses and particularly the use of a modified plant virus replicase. The expression of the coat protein of the plant virus, tobacco mosaic virus (TMV), in tobacco was the first practical validation of this concept for plant virus resistance. This work (Powell-Abel et al., 1986) showed that the expression of the TMV coat protein, from a transgene under the control of the cauliflower mosaic virus 35S promoter, conferred on the plants resistance to TMV. The same group (Powell et al., 1990) showed that, generally, plants expressing higher levels of coat protein were more resistant to TMV than plants expressing low levels. Since this demonstration there have been very many examples of plants transformed with virus coat protein genes showing resistance (Table 1). There have also been a number of reports of plant virus resistance in plants expressing wild-type replicase (Braun and Hemenway, 1992, Brederode et al., 1995), truncated replicase (Carr et al. 1992), modified replicase (Longstaff et al. 1993), or antisense viral RNA (Kawchuck et al. 1991).

In 1992, Dougherty and colleagues were using different forms of the coat protein gene of tobacco etch virus (TEV) and discovered that some plants containing untranslatable "sense" coat protein genes and antisense coat protein genes showed extreme resistance (ER) to the virus (Lindbo & Dougherty, 1992 a,b). This resistance was functional at the whole plant level and at the single cell level. TEV was unable to replicate in protoplasts derived from ER plants but replicated to high levels in protoplasts from non-transgenic tobacco. Dougherty et al. concluded that the mechanism creating the extreme resistance for the untranslatable sense construct was not the same as the often reported coat protein-mediated strategy. They proposed that the mRNA of the untranslatable sense construct was hybridizing with the minus sense genome of the virus and interfering with the procession of replication complexes on the minus strand. They suggested that the use of viral sequence that could form intramolecular pairing should be avoided as this would interfere with their ability to hybridize to the target viral RNA.

TABLE 1

Plant species that have been genetically engineered for virus resistance (from Rebecca Grumet, Hort Science 30[3] 1995)

| Species | Viruses |
| --- | --- |
| Tobacco (Nicotiana tabacum L.) | AIMV, ArMV, CMV, PVX, PVY, TEV, TGMV, TMV, TRV, TSV, TSWV |
| Other Nicotiana spp. (N. debneyii, N. benthamiana, N. clevelandii) | ACMV, BYMV, CyMV, CyRSV, BCTV, PEBV, PPV, PVS, WMV |
| Potato (Solanum tuberusom L.) | PI, RV, PVY |
| Tomato (Lycopersicon esculentum L.) | AIMV, CMV, TMV, TYLCV |
| Cucumber (Cucumis sativus L.) | CMV |
| Melon (Cucumis melo L.) | CMV, ZYMV |
| Alfalfa (Medicago sativa L.) | AIMV |
| Papaya (Carica papaya L.) | PRSV |
| Corn (Zea mays L.) | MDMV |
| Rice (Oryza sativa L.) | RSV |
| Rapeseed (Brassica napus L.) | TYMV |

The Dougherty group expanded their investigations to plants containing untranslatable sense potato virus Y (PVY) coat protein genes. They obtained results similar to those with TEV and showed that the plants with ER had high transgene copy number, highly active transcription of the transgenes, and low levels of steady state mRNA from the PVY transgene (Lindbo et al. 1993, Smith et al. 1994). The following model for this mechanism of the resistance was proposed: the high level of transcription of the viral transgene triggers a cytoplasmic based, post transcriptional cellular surveillance system that targets specific RNAs for elimination. As the transgene encodes a transcript comprising viral sequences the mechanism not only degrades the transgene mRNA but also the same sequences in the viral genomic RNA. A key point in this model is the need for a high level of transcription of the transgene provided by high copy number (3-8; Goodwin et al. 1996). Alternatively, the RNA threshold required to trigger the mechanism can be reached by a more modest transcription level aided by the viral RNA from replication in early infection. This gives rise to a "recovery phenotype" where the plant is initially infected and shows symptoms but then produces new growth without virus symptoms and which are extremely resistant to infection.

This proposal was substantiated by the findings that gene silencing of non-viral transgenes could also be due to a post transcriptional mechanism (Ingelbrecht et al. 1994; de Carvalho Niebel et al., 1995) operating at an RNA level.

A link between non-viral gene silencing and this pathogen derived resistance was provided by inoculating transgenic plants, in which a GUS transgene was known to be silenced by a post transcriptional mechanism, with a virus containing GUS sequences (English et al. 1996). In this situation the plants were extremely resistant to the viral infection. However, the same plants were susceptible to the virus if they contained no GUS sequences.

The degree of viral resistance is not always directly related to the level of viral transgene transcription (Mueller et al., 1995; English et al., 1996) suggesting that there may be an alternative mechanism of inducing the resistance. To accommodate these discrepancies, an alternative model has been proposed in which the crucial factor affecting the resistance is not the level but the quality of the transgene mRNA (English et al. 1996). According to this model, the transgene can only induce resistance (or gene silencing) if it is transcribed to produce "aberrant" RNA. There have been many examples of post-transcriptional gene silencing and methylation of the transgene (Hobbs et al. 1990; Ingelbrecht et at 1994) and methylation of the transgene has also been found to be associated in some cases of extreme viral resistance (Smith et al. 1994, English 1996). In the proposed model, methylation of the transgene leads to the production of aberrant RNAs which induce the cytoplasmic RNA surveillance system. Baulcombe and English have suggested that this method of induction may be the same as that found for the silencing of met2 in *A. immersus*. In this system transcription of the met2 RNA was terminated in the methylated regions of the endogenous gene thus producing aberrant truncated RNAs. It was suggested that the methylation was a consequence of ectopic interaction between the transgene and a homologous region of a corresponding region of the endogenous gene (Barry et al. 1993). The presence of multiple transgenes would create an increased likelihood of ectopic pairing and is therefore consistent with the correlation between high copy number and extreme viral resistance (Mueller et al., 1995; Goodwin et al. 1996; Pang et al., 1996).

This whole area has been reviewed recently (e.g. Baulcombe (1996) and Stam et al. (1997)) and several models were presented. All models call for a high degree of sequence specificity because the resistance is very (strain) specific and therefore invoke base pairing interaction with an RNA produced from the transgene. One explanation for the induction of the virus resistance or gene silencing with sense transgenes is that the plant's RNA dependent RNA polymerase generates complementary RNAs using the transgene mRNA as a template (Schiebel et al. 1993a,b). This hypothetical complementary RNA (cRNA) has not been detected (Baulcombe 1996) but it is expected that the cRNAs will be small and heterodisperse RNAs rather than full complements (Schiebel 1993ab, Baulcombe 1996) and therefore difficult to detect.

The possible methods of action of the cRNA in mediating the virus resistance or gene silencing (as proposed by Baulcombe, 1996) are:

1: The cRNA hybridizes with transgene mRNA or viral RNA and the duplex becomes a target for dsRNases;
2: The cRNA hybridizes with target RNA to form a duplex which can arrest translation and consequently have an indirect effect on stability (Green, 1993);
3: The duplex formed between the cRNA and viral RNA causes hybrid arrest of translation of co-factors required for viral replication; and
4. The hybridization of the cRNA affects intra-molecular base pairing required for viral replication.

The current models for virus resistance or gene silencing thus involve the induction of a cytoplasmic surveillance system by either high levels of transgene transcription or by the production of aberrant single stranded mRNA. Once the system is triggered, RNA dependent RNA polymerase makes cRNA from the transgene mRNA. These cRNAs hybridize to the target RNA either directly affecting its translatability or stability, or marking the RNA for degradation.

U.S. Pat. No. 5,190,131 and EP 0 467 349 A1 describe methods and means to regulate or inhibit gene expression in a cell by incorporating into or associating with the genetic material of the cell a non-native nucleic acid sequence which is transcribed to produce an mRNA which is complementary to and capable of binding to the mRNA produced by the genetic material of that cell.

EP 0 223 399 A1 describes methods to effect useful somatic changes in plants by causing the transcription in the plant cells of negative RNA strands which are substantially complementary to a target RNA strand. The target RNA strand can be a mRNA transcript created in gene expression, a viral RNA, or other RNA present in the plant cells. The negative RNA strand is complementary to at least a portion of the target RNA strand to inhibit its activity in vivo.

EP 0 240 208 describes a method to regulate expression of genes encoded for in plant cell genomes, achieved by integration of a gene under the transcriptional control of a promoter which is functional in the host and in which the transcribed strand of DNA is complementary to the strand of DNA that is transcribed from the endogenous gene(s) one wishes to regulate.

EP 0 647 715 A1 and U.S. Pat. Nos. 5,034,323, 5,231,020 and 5,283,184 describe methods and means for producing plants exhibiting desired phenotypic traits, by selecting transgenotes that comprise a DNA segment operably linked to a promoter, wherein transcription products of the segment are substantially homologous to corresponding transcripts of endogenous genes, particularly endogenous flavonoid biosynthetic pathway genes.

W0 93/23551 describes methods and means for the inhibition of two or more target genes, which comprise introducing into the plant a single control gene which has distinct DNA regions homologous to each of the target genes and a promoter operative in plants adapted to transcribe from such distinct regions RNA that inhibits expression of each of the target genes.

WO92/13070 describes a method for the regulation of nucleic acid translation, featuring a responsive RNA molecule which encodes a polypeptide and further includes a regulatory domain, a substrate region and a ribosome recognition sequence. This responsive RNA molecule has an inhibitor region in the regulatory domain, which regulatory domain is complementary to both a substrate region of the responsive RNA molecule and to an anti-inhibitor region of a signal nucleic acid such that, in the absence of the signal nucleic acid, the inhibitor and substrate regions form a base-paired domain the formation of which reduced the level of translation of one of the protein-coding regions in the responsive RNA molecule compared to the level of translation of that one protein-coding region observed in the presence of the signal nucleic acid.

Metzlaff et al., 1997 describe a model for the RNA-mediated RNA degradation and chalcone synthase A silencing in Petunia, involving cycles of RNA-RNA pairing between complementary sequences followed by endonucleolytic RNA cleavages to describe how RNA degradation is likely to be promoted. Fire et al., 1998 describe specific genetic interference by experimental introduction of double-stranded RNA in *Caenorhabditis elegans*. The importance of these findings for functional genomics is discussed (Wagner and Sun, 1998).

Que et al., 1998 describe distinct patterns of pigment suppression which are produced by allelic sense and antisense chalcone synthase transgenes in petunia flowers and have also analyzed flower color patterns in plants heterozygous for sense and antisense chalcone synthase alleles.

WO 98/05770 discloses antisense RNA with special secondary structures which may be used to inhibit gene expression.

WO 94/18337 discloses transformed plants which have increased or decreased linolenic acids as well as plants which express a linoleic acid desaturase.

U.S. Pat. No. 5,850,026 discloses an endogenous oil from *Brassica* seeds that contains, after crushing and extracting, greater than 86% oleic acid and less than 2.5% α-linolenic acid. The oil also contains less than 7% linoleic acid. The *Brassica* seeds are produced by plants that contain seed-specific inhibition of microsomal oleate desaturase and microsomal linoleate desaturase gene expression, wherein the inhibition can be created by cosuppression or antisense technology.

U.S. Pat. No. 5,638,637 discloses vegetable oil from rapeseeds and rapeseed producing the same, the vegetable oil having an unusually high oleic acid content of 80% to 90% by weight based on total fatty acid content.

SUMMARY OF THE INVENTION

The present invention provides methods for reducing the phenotypic expression of a nucleic acid of interest, which is normally capable of being expressed in a eucaryotic cell, particularly for reducing the phenotypic expression of a gene, particularly a endogenous gene or a foreign transgene, integrated in the genome of a eucaryotic cell or for reducing the phenotypic expression of nucleic acid of interest which is comprised in the genome of an infecting virus, comprising the step of introducing, preferably integrating, in the nuclear genome of the eucaryotic cell, a chimeric DNA comprising a promoter, capable of being expressed in that eucaryotic cell, and optionally a DNA region involved in transcription termination and polyadenylation and in between a DNA region, which when transcribed, yields an RNA molecule with a nucleotide sequence comprising a sense nucleotide sequence of at least 10 consecutive nucleotides, particularly at least about 550 consecutive nucleotides, having between 75 and 100% sequence identity with at least part of the nucleotide sequence of the nucleic acid of interest, and an antisense nucleotide sequence including at least 10 consecutive nucleotides, having between about 75% to about 100% sequence identity with the 10 nucleotide stretch of the complement of the sense nucleotide sequence, wherein the RNA is capable of forming an artificial hairpin RNA structure with a double stranded RNA stem by base-pairing between the regions with sense and antisense nucleotide sequence such that at least the 10 consecutive nucleotides of the sense sequence base pair with the 10 consecutive nucleotides of the antisense sequence, resulting in, preferably an artificial hairpin structure. Preferably the chimeric DNA is stably integrated in the genome of the DNA.

The invention also provides a method for reducing the phenotypic expression of a nucleic acid of interest, which is normally capable of being expressed in a eucaryotic cell comprising the step of introducing a chimeric RNA molecule with a nucleotide sequence comprising a sense nucleotide sequence of at least 10 consecutive nucleotides having between 75 and 100% sequence identity with at least part of the nucleotide sequence of the nucleic acid of interest; and an antisense nucleotide sequence including at least 10 consecutive nucleotides, having between about 75% to about 100% sequence identity with 10 nt stretch of the complement of the sense nucleotide sequence; wherein the RNA is capable of forming a double stranded RNA region by base-pairing between the regions with sense and antisense nucleotide sequence such that at least the 10 consecutive nucleotides of the sense sequence base pair with the 10 consecutive nucleotides of the antisense sequence, resulting in a (n artificial) hairpin RNA structure.

The invention further provides a method for reducing the gene expression of a gene of interest in plant cells, comprising the step of introducing a first and second chimeric DNA, linked on one recombinant DNA such that both chimeric DNAs are integrated together in the nuclear genome of the transgenic plant cells; wherein the first chimeric DNA comprises a plant-expressible promoter, a first DNA region capable of being transcribed into a sense RNA molecule with a nucleotide sequence comprising a sense nucleotide sequence of at least 10 consecutive nucleotides having between 75 and 100% sequence identity with at least part of the nucleotide sequence of the gene of interest and optionally a DNA region involved in transcription termination and polyadenylation functioning in plant cells. The second chimeric DNA comprises a plant-expressible promoter, a second DNA region capable of being transcribed into an antisense RNA molecule with a nucleotide sequence comprising an antisense nucleotide sequence including at least 10 consecutive nucleotides, having between about 75% to about 100% sequence identity with the complement of the at least 10 consecutive nucleotides of the sense nucleotide sequence and optionally a DNA region involved in transcription termination and polyadenylation functioning in plant cells. The sense and antisense RNA molecules are capable of forming a double stranded, duplex RNA by base-pairing between the regions which are complementary.

Also provided by the invention is a method for obtaining virus resistant organisms, particularly plants, comprising the steps of providing cells of the organism with a first and second chimeric DNA, wherein the first chimeric DNA comprises a promoter, a first DNA region capable of being transcribed into a sense RNA molecule with a nucleotide sequence comprising a sense nucleotide sequence of at least 10 consecutive nucleotides having between 75 and 100% sequence identity with at least part of the nucleotide sequence of the genome of a virus, capable of infecting the plant and a DNA region involved in transcription termination and polyadenylation functioning in plant cells. The second chimeric DNA comprises a promoter, a second DNA region capable of being transcribed into an antisense RNA molecule with a nucleotide sequence comprising an antisense nucleotide sequence including at least 10 consecutive nucleotides, having between about 75% to about 100% sequence identity with the complement of at least 10 consecutive nucleotides of the sense nucleotide sequence and a DNA region involved in transcription termination and polyadenylation functioning in plant cells. The sense and antisense RNA molecules are capable of forming a double stranded RNA region by base-pairing between the regions which are complementary.

The first and second chimeric DNA are either integrated separately in the nuclear genome of the transformed plant cell or they are linked on one recombinant DNA such that both chimeric DNAs are integrated together in the nuclear genome of the transgenic plant cells.

The invention also provides a method for identifying a phenotype associated with the expression of a nucleic acid of interest in a eucaryotic cell, comprising the steps of selecting within the nucleotide sequence of interest, a target sequence of at least 10 consecutive nucleotides; designing a sense nucleotide sequence corresponding to the length of the selected target sequence and which has a sequence identity of at least about 75% to about 100% with the selected target sequence, designing an antisense nucleotide sequence which has a sequence identity of at least about 75% to about 100% with the complement of the sense nucleotide sequence and comprises a stretch of at least about 10 consecutive nucleotides with 100% sequence identity to the complement of a part of the sense nucleotide sequence. The method further comprises the steps of introducing an RNA molecule comprising both the designed sense and antisense nucleotide sequences into a suitable eucaryotic host cell comprising the nucleic acid including the nucleotide sequence with hitherto unidentified phenotype; and observing the phenotype by a suitable method.

The invention also provides a eucaryotic cell, comprising a nucleic acid of interest which is normally capable of being phenotypically expressed, further comprising a chimeric DNA molecule comprising a promoter, capable of being expressed in that eucaryotic cell, a DNA region, which when transcribed, yields an RNA molecule with a nucleotide sequence comprising a sense nucleotide sequence of at least 10 consecutive nucleotides having between 75 and 100% sequence identity with at least part of the nucleotide sequence of the nucleic acid of interest and an antisense nucleotide sequence including at least 10 consecutive nucleotides, having between about 75% to about 100% sequence identity with the complement of the at least 10 consecutive nucleotides of the sense nucleotide sequence wherein the RNA molecule is capable of forming a double stranded RNA region by base-pairing between the regions with sense and antisense nucleotide sequence such that at least said 10 consecutive nucleotides of the sense sequence base pair with said 10 consecutive nucleotides of the antisense sequence, resulting in a hairpin RNA structure, preferably an artificial hairpin structure and a DNA region involved in transcription termination and polyadenylation, wherein the phenotypic expression of the nucleic acid of interest is significantly reduced.

Also provided by the invention is a eucaryotic cell, comprising a nucleic acid of interest, which is normally capable of being phenotypically expressed, further comprising a chimeric RNA molecule with a nucleotide sequence comprising a sense nucleotide sequence of at least 10 consecutive nucleotides having between 75 and 100% sequence identity with at least part of the nucleotide sequence of the nucleic acid of interest and an antisense nucleotide sequence including at least 10 consecutive nucleotides, having between about 75% to about 100% sequence identity with the complement of the at least 10 consecutive nucleotides of the sense nucleotide sequence wherein the RNA is capable of forming a double stranded RNA region by base-pairing between the regions with sense and antisense nucleotide sequence such that at least said 10 consecutive nucleotides of the sense sequence basepair with said 10 consecutive nucleotides of the antisense sequence, resulting in an artificial hairpin RNA structure.

It is another objective of the invention to provide a eucaryotic cell, comprising a gene of interest, which is normally capable of being phenotypically expressed, further comprising a first and second chimeric DNA, linked on one recombinant DNA such that both chimeric DNAs are integrated together in the nuclear genome of that eucaryotic cell wherein the first chimeric DNA comprises the following operably linked parts a promoter capable of being expressed in the eucaryotic cell a first DNA region capable of being transcribed into a sense RNA molecule with a nucleotide sequence comprising a sense nucleotide sequence of at least 10 consecutive nucleotides having between 75 and 100% sequence identity with at least part of the nucleotide sequence of the gene of interest; and a DNA region involved in transcription termination and polyadenylation; and wherein the second chimeric DNA comprises the following operably linked parts: a promoter operative in the eucaryotic cell; a second DNA region capable of being transcribed into an antisense RNA molecule with a nucleotide sequence comprising an antisense nucleotide sequence including at least 10 consecutive nucleotides, having between about 75% to about 100% sequence identity with the complement of the at least 10 consecutive nucleotides of the sense nucleotide sequence; a DNA region involved in transcription termination and polyadenylation; wherein the sense and antisense RNA molecules are capable of forming a double stranded RNA region by base-pairing between the regions which are complementary.

It is yet another objective of the invention to provide a virus resistant plant, comprising a first and second chimeric DNA integrated in the nuclear genome of its cells, wherein the first chimeric DNA comprises a plant-expressible promoter, a first DNA region capable of being transcribed into a sense RNA molecule with a nucleotide sequence comprising a sense nucleotide sequence of at least 10 consecutive nucleotides having between 75 and 100% sequence identity with at least part of the nucleotide sequence of the genome of a virus, capable of infecting the plant, and a DNA region involved in transcription termination and polyadenylation functioning in plant cells. The second chimeric DNA comprises a plant-expressible promoter, a second DNA region capable of being transcribed into an antisense RNA molecule with a nucleotide sequence comprising an antisense nucleotide sequence including at least 10 consecutive nucleotides, having between about 75% to about 100% sequence identity with the complement of the at least 10 consecutive nucleotides of the sense nucleotide sequence, and a DNA region involved in transcription termination and polyadenylation functioning in plant cells. The sense and antisense RNA molecules are capable of forming a double stranded RNA region by base-pairing between the regions which are complementary. The first and second chimeric DNA are integrated either in one locus or in different loci in the nuclear genome.

The invention also provides a method for modifying the fatty acid profile in oil, preferably increasing the oleic acid content, from a plant, preferably from oilseed rape, the method comprising the step of introducing a chimeric DNA into the cells of the plant, comprising the following operably linked parts: a). a plant-expressible promoter, preferably a seed-specific promoter; b). a DNA region, particularly with the nucleotide sequence of SEQ ID No 6, which when transcribed yields an RNA molecule comprising an RNA region capable of forming an artificial stem-loop structure, wherein one of the annealing RNA sequences of the stem-loop structure comprises a nucleotide sequence essentially similar to at least part of the nucleotide sequence of a Δ12 desaturase encoding open reading frame, and wherein the second of the annealing RNA sequences comprises a sequence essentially similar to at least part of the complement of at least part of the nucleotide sequence of the Δ12 desaturase encoding open reading frame; and optionally; c) a DNA region involved in transcription termination and polyadenylation. Plants with modified fatty acid profile, particularly with increased oleic acid content, comprising the mentioned chimeric genes are also provided by the invention. Also encompassed are oils obtained from such plants or seed.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1 represents schematically the different sense and antisense constructs, as well as the so-called CoP (complementary pair) constructs used for obtaining virus resistance (FIG. 1B) or for reducing the phenotypic expression of a transgenic Gus gene (FIG. 1A).

DETAILED DESCRIPTION OF THE PREFERRED EMBODIMENTS OF THE INVENTION

Figure 2:
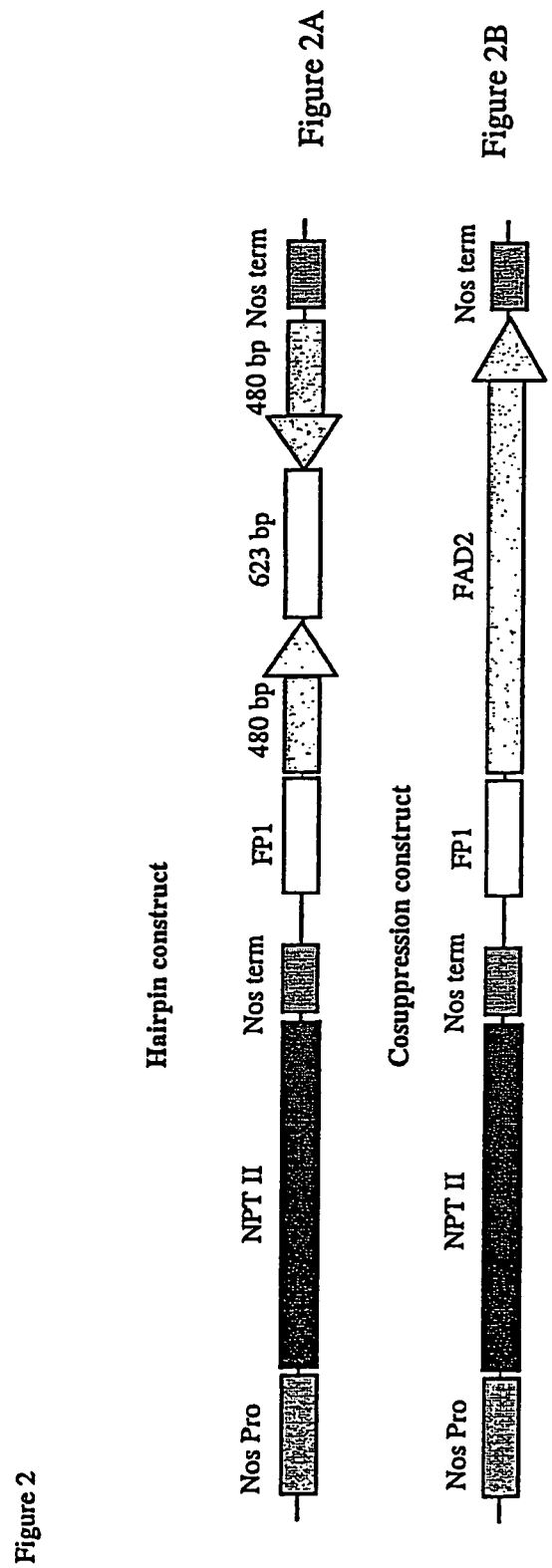
FIG. 2A represents schematically the so-called panhandle construct or CoP constructs used for reducing the phenotypic expression of a Δ12 desaturase gene in *Arabidopsis* (Nos Pro: nopaline synthase gene promoter; nptII neomycin phosphotransferase coding region; Nos term: nopaline syntase gene terminator; FP1: truncated seed specific napin promoter; 480 bp: 5' end of the Fad2 gene of *Arabidopsis thaliana* in sense orientation; 623 bp: spacer; 480 bp: 5' end of the Fad2 gene of *Arabidopsis thaliana* in antisense orientation.
FIG. 2B represents schematically a common cosuppression construct for for reducing the phenotypic expression of a Δ12 desaturase gene in *Arabidopsis thaliana*.

One of the objectives of the invention is to provide a eucaryotic cell, particularly a plant cell with an RNA molecule which comprises a hairpin structure including a determined sense part and a determined antisense part. Potentially, an RNA molecule is capable of forming several secondary structures, some of which may contain the desired hairpin. It is expected that the real secondary structure of the RNA in the cell, will have the lowest free energy. In accordance with the invention, the RNA molecule to be produced in the cell is designed in such a way that at least in its lowest free energy state, which it can assume within that cell, it will comprise the desired hairpin.

As used herein "hairpin RNA" refers to any self-annealing double stranded RNA molecule. In its simplest representation, a hairpin RNA consists of a double stranded stem made up by the annealing RNA strands, connected by a single stranded RNA loop, and is also referred to as a "pan-handle RNA". However, the term "hairpin RNA" is also intended to encompass more complicated secondary RNA structures comprising self-annealing double stranded RNA sequences, but also internal bulges and loops. The specific secondary structure adapted will be determined by the free energy of the RNA molecule, and can be predicted for different situations using appropriate software such as FOLDRNA (Zuker and Stiegler, 1981).

As used herein, "sequence identity" with regard to nucleotide sequences (DNA or RNA), refers to the number of positions with identical nucleotides divided by the number of nucleotides in the shorter of the two sequences. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can, e.g., be conveniently performed using the programs of the Intelligenetics™ Suite (Intelligenetics Inc., CA). Sequences are indicated as "essentially similar" when such sequence have a sequence identity of at least about 75%, particularly at least about 80%, more particularly at least about 85%, quite particularly about 90%, especially about 95%, more especially about 100%, quite especially are identical. It is clear than when RNA sequences are said to be essentially similar or have a certain degree of sequence identity with DNA sequences, thymine (T) in the DNA sequence is considered equal to uracil (U) in the RNA sequence.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S, the subterranean clover virus promoter No 4 or No 7, or T-DNA gene promoters.

The term "expression of a gene" refers to the process wherein a DNA region which is operably linked to appropriate regulatory regions, particularly to a promoter, is transcribed into an RNA which is biologically active i.e., which is either capable of interaction with another nucleic acid or which is capable of being translated into a polypeptide or protein. A gene is said to encode an RNA when the end product of the expression of the gene is biologically active RNA, such as e.g. an antisense RNA, a ribozyme or a replicative intermediate. A gene is said to encode a protein when the end product of the expression of the gene is a protein or polypeptide.

A nucleic acid of interest is "capable of being expressed", when said nucleic acid, when introduced in a suitable host cell, particularly in a plant cell; can be transcribed (or replicated) to yield an RNA, and/or translated to yield a polypeptide or protein in that host cell.

The term "gene" means any DNA fragment comprising a DNA region (the "transcribed DNA region") that is transcribed into a RNA molecule (e.g., an mRNA) in a cell operably linked to suitable regulatory regions, e.g., a plant-expressible promoter. A gene may thus comprise several operably linked DNA fragments such as a promoter, a 5' leader sequence, a coding region, and a 3' region comprising a polyadenylation site. A plant gene endogenous to a particular plant species (endogenous plant gene) is a gene which is naturally found in that plant species or which can be introduced in that plant species by conventional breeding. A chimeric gene is any gene which is not normally found in a plant species or, alternatively, any gene in which the promoter is not associated in nature with part or all of the transcribed DNA region or with at least one other regulatory region of the gene.

As used herein, "phenotypic expression of a nucleic acid of interest" refers to any quantitative trait associated with the molecular expression of a nucleic acid in a host cell and may thus include the quantity of RNA molecules transcribed or replicated, the quantity of post-transcriptionally modified RNA molecules, the quantity of translated peptides or proteins, the activity of such peptides or proteins.

A "phenotypic trait" associated with the phenotypic expression of a nucleic acid of interest refers to any quantitative or qualitative trait, including the trait mentioned, as well as the direct or indirect effect mediated upon the cell, or the organism containing that cell, by the presence of the RNA molecules, peptide or protein, or posttranslationally modified peptide or protein. The mere presence of a nucleic acid in a host cell, is not considered a phenotypic expression or a phenotypic trait of that nucleic acid, even though it can be quantitatively or qualitatively traced. Examples of direct or indirect effects mediated on cells or organisms are, e.g., agronomically or industrial useful traits, such as resistance to a pest or disease; higher or modified oil content etc.

As used herein, "reduction of phenotypic expression" refers to the comparison of the phenotypic expression of the nucleic acid of interest to the eucaryotic cell in the presence of the RNA or chimeric genes of the invention, to the phenotypic expression of the nucleic acid of interest in the absence of the RNA or chimeric genes of the invention. The phenotypic expression in the presence of the chimeric RNA of the invention should thus be lower than the phenotypic expression in absence thereof, preferably be only about 25%, particularly only about 10%, more particularly only about 5% of the phenotypic expression in absence of the chimeric RNA, especially the phenotypic expression should be completely inhibited for all practical purposes by the presence of the chimeric RNA or the chimeric gene encoding such an RNA.

A reduction of phenotypic expression of a nucleic acid where the phenotype is a qualitative trait means that in the presence of the chimeric RNA or gene of the invention, the phenotypic trait switches to a different discrete state when compared to a situation in which such RNA or gene is absent. A reduction of phenotypic expression of a nucleic acid may thus, a.o., be measured as a reduction in transcription of (part of) that nucleic acid, a reduction in translation of (part of) that nucleic acid or a reduction in the effect the presence of the transcribed RNA(s) or translated polypeptide(s) have on the eucaryotic cell or the organism, and will ultimately lead to altered phenotypic traits. It is clear that the reduction in phenotypic expression of a nucleic acid of interest, may be accompanied by or correlated to an increase in a phenotypic trait.

As used herein "a nucleic acid of interest" or a "target nucleic acid" refers to any particular RNA molecule or DNA sequence which may be present in a eucaryotic cell, particularly a plant cell.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined, may comprise additional DNA regions etc.

It has unexpectedly been found by the inventors, that introduction of a chimeric gene capable of being transcribed into an RNA molecule with a nucleotide sequence comprising both the sense and antisense nucleotide sequence of a target gene, or part thereof, integrated in the nuclear genome of a plant cell, could efficiently and specifically reduce the phenotypic expression of that target gene. The reduction in phenotypic expression was more efficient and more predictable than observed when separate chimeric genes were introduced in similar cells with the target gene, encoding either sense or antisense RNA molecules.

At the same time, it has also been found that simultaneously introducing separate chimeric genes in one cell encoding RNA molecules with nucleotide sequences comprising sense and antisense respectively, resulted in extreme virus resistance, even when the chimeric genes were transcribed from weaker promoters. It is well known that gene silencing and virus resistance can be mediated by similar phenomena.

In one embodiment of the invention, a method for reducing the phenotypic expression of a nucleic acid of interest, which is normally capable of being expressed in a eucaryotic cell, particularly a plant cell, is provided, comprising the steps of introducing a chimeric DNA comprising the following operably linked parts:
  a) a promoter, operative in that cell, particularly a plant-expressible promoter;
  b) a DNA region capable of being transcribed into an RNA molecule with a nucleotide sequence comprising
    i. a sense nucleotide sequence of at least 10 nt, preferably 15 nt consecutive nucleotides having between 75 and 100% sequence identity with at least part of the nucleotide sequence of the nucleic acid of interest; and
    ii. an antisense nucleotide sequence including at least 10, preferably 15 nt consecutive nucleotides, having between about 75% to about 100% sequence identity with the complement of the at least 10, preferably 15 nt consecutive nucleotides of the sense nucleotide sequence;
  wherein the RNA is capable of forming a double stranded RNA by base-pairing between the regions with sense and antisense nucleotide sequence resulting in a hairpin RNA structure; and
  c) a DNA region involved in transcription termination and polyadenylation functioning in the suitable eucaryotic cells, particularly functioning in plant cells.

In a preferred embodiment of the invention, the RNA molecule transcribed from the chimeric gene, consists essentially of the hairpin RNA.

The order of the sense and antisense nucleotide sequence in the RNA molecule is thought not be critical.

Thus, in other words, the chimeric DNA has a transcribed DNA region, which when transcribed, yields an RNA molecule comprising an RNA region capable of forming an artificial stem-loop structure, wherein one of the annealing RNA sequences of the stem-loop structure comprises a sequence, essentially similar to at least part of the nucleotide sequence of the nucleic acid of interest, and wherein the second of the annealing RNA sequences comprises a sequence essentially similar to at least part of the complement of at least part of the nucleotide sequence of the nucleic acid of interest.

The RNA molecule may comprise several artificial hairpin structures, which may be designed to reduce the phenotypic expression of different nucleic acids of interest.

In one preferred embodiment, the nucleic acid of interest, whose phenotypic expression is targeted to be reduced, is a gene incorporated in the genome of a eucaryotic cell, particularly a plant cell. It will be appreciated that the means and methods of the invention can be used for the reduction of phenotypic expression of a gene which belongs to the genome of the cell as naturally occurring, (an endogenous gene), as well as for the reduction of phenotypic expression of a gene which does not belong to the genome of the cell as naturally occurring, but has been introduced in that cell (a transgene). The transgene can be introduced stably or transiently, and can be integrated into the nuclear genome of the cell, or be present on a replicating vector, such as a viral vector.

In another preferred embodiment, the nucleic acid of interest, whose phenotypic expression is targeted to be reduced is a viral nucleic acid, particularly a viral RNA molecule, capable of infecting a eucaryotic cell, particularly a plant cell. In this case, the phenotype to be reduced is the replication of the virus, and ultimately, the disease symptoms caused by the infecting virus.

Preferably, the nucleotide sequence of the target nucleic acid corresponding to the sense nucleotide sequence is part of a DNA region which is transcribed, particularly a DNA region which is transcribed and translated (in other words a coding region). It is particularly preferred that the target sequence corresponds to one or more consecutive exons, more particularly is located within a single exon of a coding region.

The length of the sense nucleotide sequence may vary from about 10 nucleotides (nt) up to a length equaling the length (in nucleotides) of the target nucleic acid. Preferably the total length of the sense nucleotide sequence is at least 10 nt, preferably 15 nt, particularly at least about 50 nt, more particularly at least about 100 nt, especially at least about 150 nt, more especially at least about 200 nt, quite especially at least about 550 nt. It is expected that there is no upper limit to the total length of the sense nucleotide sequence, other than the total length of the target nucleic acid. However for practical reason (such as e.g. stability of the chimeric genes) it is expected that the length of the sense nucleotide sequence should not exceed 5000 nt, particularly should not exceed 2500 nt and could be limited to about 1000 nt.

It will be appreciated that the longer the total length of the sense nucleotide sequence is, the less stringent the requirements for sequence identity between the total sense nucleotide sequence and the corresponding sequence in the target gene become. Preferably, the total sense nucleotide sequence should have a sequence identity of at least about 75% with the corresponding target sequence, particularly at least about 80%, more particularly at least about 85%, quite particularly about 90%, especially about 95%, more especially about 100%, quite especially be identical to the corresponding part of the target nucleic acid. However, it is preferred that the sense nucleotide sequence always includes a sequence of about 10 consecutive nucleotides, particularly about 20 nt, more particularly about 50 nt, especially about 100 nt, quite especially about 150 nt with 100% sequence identity to the corresponding part of the target nucleic acid. Preferably, for calculating the sequence identity and designing the corresponding sense sequence, the number of gaps should be minimized, particularly for the shorter sense sequences.

The length of the antisense nucleotide sequence is largely determined by the length of the sense nucleotide sequence, and will preferably correspond to the length of the latter sequence. However, it is possible to use an antisense sequence which differs in length by about 10%. Similarly, the nucleotide sequence of the antisense region is largely determined by the nucleotide sequence of the sense region, and preferably is identical to the complement of the nucleotide sequence of the sense region. Particularly with longer antisense regions, it is however possible to use antisense sequences with lower sequence identity to the complement of the sense nucleotide sequence, preferably with at least about 75% sequence identity, more preferably with at least about 80%, particularly with at least about 85%, more particularly with at least about 90% sequence identity, especially with at least about 95% sequence to the complement of the sense nucleotide sequence. Nevertheless, it is preferred that the antisense nucleotide sequences always includes a sequence of about 10, preferably 15 consecutive nucleotides, particularly about 20 nt, more particularly about 50 nt, especially about 100 nt, quite especially about 150 nt with 100% sequence identity to the complement of a corresponding part of the sense nucleotide sequence. It is clear that the length of the stretch of the consecutive nucleotides with 100% sequence identity to the complement of the sense nucleotide sequence cannot be longer than the sense nucleotide sequence itself. Again, preferably the number of gaps should be minimized, particularly for the shorter antisense sequences. Further, it is also preferred that the antisense sequence has between about 75% to 100% sequence identity with the complement of the target sequence.

The RNA molecule resulting from the transcription of the chimeric DNA may comprise a spacer nucleotide sequence located between the sense and antisense nucleotide sequence. In the absence of such a spacer sequence, the RNA molecule will still be able to form a double-stranded RNA, particularly if the sense and antisense nucleotide sequence are larger than about 10 nucleotides and part of the sense and/or antisense nucleotide sequence will be used to form the loop allowing the base-pairing between the regions with sense and antisense nucleotide sequence and formation of a double stranded RNA. It is expected that there are no length limits or sequence requirements associated with the spacer region, as long as these parameters do not interfere with the capability of the RNA regions with the sense and antisense nucleotide sequence to form a double stranded RNA. In a preferred embodiment, the spacer region varies in length from 4 to about 200 bp, but as previously mentioned, it may be absent.

In a preferred embodiment, the hairpin RNA formed by the sense and antisense region and if appropriate the spacer region, is an artificial hairpin RNA. By "artificial hairpin RNA" or "artificial stem-loop RNA structure", is meant that such hairpin RNA is not naturally occurring in nature, because the sense and antisense regions as defined are not naturally occurring simultaneously in one RNA molecule, or the sense and antisense regions are separated by a spacer region which is heterologous with respect to the target gene, particularly, the nucleotide sequence of the spacer has a sequence identity of less than 75% with the nucleotide sequence of the target sequence, at the corresponding location 5' or 3' of the endpoints of the sense nucleotide sequence. A hairpin RNA can also be indicated as artificial, if it is not comprised within the RNA molecule it is normally associated with. It is conceivable to use in accordance with the invention a chimeric DNA whose transcription results in a hairpin RNA structure with a naturally occurring nucleotide sequence (which otherwise meets the limits as set forth in this specification) provided this hairpin RNA is devoid of the surrounding RNA sequences (not involved in the hairpin structure formation).

Although it is preferred that the RNA molecule comprising the hairpin RNA does not further comprise an intron sequence, it is clear that the chimeric DNA genes encoding such RNAs may comprise in their transcribed region one or more introns.

In fact, the inventors have unexpectedly found that inclusion of an intron sequence in the chimeric DNA genes encoding an RNA molecule comprising the hairpin RNA, preferably in the spacer region, and preferably in sense orientation, enhances the efficiency of reduction of expression of the target nucleic acid. The enhancement in efficiency may be expressed as an increase in the frequency of plants wherein silencing occurs or as an increase in the level of reduction of the phenotypic trait. In a particularly preferred embodiment, the intron is essentially identical in sequence to the *Flaveria trinervia* pyruvate orthophosphate dikinase 2 intron 2, more particularly, it comprises the sequence of SEQ ID No 7.

It has been observed that contrary to methods using either antisense or sense nucleotide sequences alone to reduce the phenotypic expression of a target nucleic acid (which generally depend on the dosage of sense or antisense molecule, and thus the chimeric genes encoding the sense and antisense molecules need to be under the control of relatively strong promoters) the method of the current invention does not rely on the presence of such strong promoter regions to drive the transcriptional production of the RNA comprising both the sense and antisense region. In other words, a whole range of promoters, particularly plant expressible promoters, is available to direct the transcription of the chimeric genes of the invention. These include, but are not limited to strong promoters such as CaMV35S promoters (e.g., Harpster et al., 1988). In the light of the existence of variant forms of the CaMV35S promoter, as known by the skilled artisan, the object of the invention can equally be achieved by employing these alternative CaMV35S promoters and variants. It is also clear that other plant-expressible promoters, particularly constitutive promoters, such as the opine synthase promoters of the *Agrobacterium* Ti- or Ri-plasmids, particularly a nopaline synthase promoter, or subterranean clover virus promoters can be used to obtain similar effects. Also contemplated by the invention are chimeric genes to reduce the phenotypic expression of a nucleic acid in a cell, which are under the control of single subunit bacteriophage RNA polymerase specific promoters, such as a T7 or a T3 specific promoter, provided that the host cells also comprise the corresponding RNA polymerase in an active form.

It is a further object of the invention, to provide methods for reducing the phenotypic expression of a nucleic acid in specific cells, particularly specific plant cells by placing the chimeric genes of the invention under control of tissue-specific or organ-specific promoters. Such tissue-specific or organ-specific promoters are well known in the art and include but are not limited to seed-specific promoters (e.g., WO89/03887), organ-primordia specific promoters (An et al., 1996), stem-specific promoters (Keller et al., 1988), leaf specific promoters (Hudspeth et al., 1989), mesophyl-specific promoters (such as the light-inducible Rubisco promoters), root-specific promoters (Keller et al., 1989), tuber-specific promoters (Keil et al., 1989), vascular tissue specific promoters (Peleman et al., 1989), stamen-selective promoters (WO 89/10396, WO 92/13956), dehiscence zone specific promoters (WO 97/13865) and the like.

In another embodiment of the invention, the expression of a chimeric gene to reduce the phenotypic expression of a target nucleic acid can be controlled at will by the application of an appropriate chemical inducer, by operably linking the transcribed DNA region of the chimeric genes of the invention to a promoter whose expression is induced by a chemical compound, such as the promoter of the gene disclosed in European Patent publication ("EP") 0332104, or the promoter of the gene disclosed in WO 90/08826.

It has been found that a similar reduction in phenotypic expression of a nucleic acid of interest in a eucaryotic cell, particularly in a plant cell, can be obtained by providing the sense and antisense RNA encoding transcribable DNA regions as separate transgenes, preferably located in one locus, particularly as one allele.

Thus, in another embodiment of the invention a method for reducing the phenotypic expression of a nucleic acid which is normally capable of being expressed in a eucaryotic cell, particularly a plant cell, is provided, comprising the steps of introducing a first and second chimeric DNA, linked on one recombinant DNA such that both chimeric DNAs are integrated together in the nuclear genome of the transgenic cells;

wherein the first chimeric DNA comprises the following operably linked parts:
  a) a promoter, operative in the cell, particularly a plant-expressible promoter;
  b) a DNA region capable of being transcribed into a sense RNA molecule with a nucleotide sequence comprising a sense nucleotide sequence of at least 10, preferably 15 consecutive nucleotides having between 75 and 100% sequence identity with at least part of the nucleotide sequence of the nucleic acid of interest; and
  c) a DNA region involved in transcription termination and polyadenylation functioning in the corresponding eucaryotic cell; and wherein the second chimeric DNA comprises the following operably linked parts:
  a) a promoter, operative in the cell, particularly a plant-expressible promoter;
  b) a DNA region capable of being transcribed into an antisense RNA molecule with a nucleotide sequence comprising an antisense nucleotide sequence including at least 10, preferably 15 consecutive nucleotides, having between about 75% to about 100% sequence identity with the complement of the at least 10, preferably 15 consecutive nucleotides of the sense nucleotide sequence;
  c) a DNA region involved in transcription termination and polyadenylation functioning in the corresponding eucaryotic cell;

wherein the sense and antisense RNA are capable of forming a double stranded RNA by base-pairing between the regions which are complementary.

Preferred embodiments for the different structural and functional characteristics, such as length and sequence of sense, antisense and spacer regions, of this method are as described elsewhere in this specification.

The RNA molecule, comprising the sense and antisense nucleotide sequences capable of forming a hairpin structure, which are produced by the transcription of the chimeric genes, can also be introduced directly in a plant cell to reduce the phenotypic expression of the target nucleic acid, particularly to reduce the phenotypic expression of a targeted endogenous gene, or a targeted transgene. Such RNA molecules could be produced e.g. by 1. cloning the DNA region capable of being transcribed into an RNA molecule with a nucleotide sequence comprising a sense nucleotide sequence of at least 10 consecutive nucleotides having between 75 and 100% sequence identity with at least part of the nucleotide sequence of the nucleic acid of interest and an antisense nucleotide sequence including at least 10 consecutive nucleotides, having between about 75% to about 100% sequence identity with the complement of the at least 10 consecutive nucleotides of the sense nucleotide sequence, whereby the RNA is capable of forming a double stranded RNA by base-pairing between the regions with sense and antisense nucleotide sequence resulting in a hairpin RNA structure, under control of a promoter suitable for recognition by a DNA-dependent RNA polymerase in an in vitro transcription reaction, such as but not limited to a T7-polymerase specific promoter;

2. performing an in vitro transcription reaction by adding inter alia the suitable DNA-dependent RNA polymerase as well as the required reagents to generate the RNA molecules; and 3. isolating the RNA molecules.

In vitro transcription methods as well as other methods for in vitro RNA production are well known in the art and commercial kits are available. Methods for direct introduction of RNA in plant cells are also available to the skilled person and include but are not limited to electroporation, microinjection and the like.

The chimeric gene(s) for reduction of the phenotypic expression of a target nucleic acid of interest in a cell, may be introduced either transiently, or may be stably integrated in the nuclear genome of the cell. In one embodiment, the chimeric gene is located on a viral vector, which is capable of replicating in the eucaryotic cell, particularly the plant cell (see e.g., WO 95/34668 and WO 93/03161).

The recombinant DNA comprising the chimeric gene to reduce the phenotypic expression of a nucleic acid of interest in a host cell, may be accompanied by a chimeric marker gene, particularly when the stable integration of the transgene in the genome of the host cell is envisioned. The chimeric marker gene can comprise a marker DNA that is operably linked at its 5' end to a promoter, functioning in the host cell of interest, particularly a plant-expressible promoter, preferably a constitutive promoter, such as the CaMV 35S promoter, or a light inducible promoter such as the promoter of the gene encoding the small subunit of Rubisco; and operably linked at its 3' end to suitable plant transcription 3' end formation and polyadenylation signals. It is expected that the choice of the marker DNA is not critical, and any suitable marker DNA can be used. For example, a marker DNA can encode a protein that provides a distinguishable color to the transformed plant cell, such as the A1 gene (Meyer et al., 1987), can provide herbicide resistance to the transformed plant cell, such as the bar gene, encoding resistance to phosphinothricin (EP 0,242,246), or can provide antibiotic resistance to the transformed cells, such as the aac(6') gene, encoding resistance to gentamycin (WO94/01560).

A recombinant DNA comprising a chimeric gene to reduce the phenotypic expression of a gene of interest, can be stably incorporated in the nuclear genome of a cell of a plant. Gene transfer can be carried out with a vector that is a disarmed Ti-plasmid, comprising a chimeric gene of the invention, and carried by *Agrobacterium*. This transformation can be carried out using the procedures described, for example, in EP 0 116 718.

Alternatively, any type of vector can be used to transform the plant cell, applying methods such as direct gene transfer (as described, for example, in EP 0 233 247), pollen-mediated transformation (as described, for example, in EP 0 270 356, WO85/01856 and U.S. Pat. No. 4,684,611), plant RNA virus-mediated transformation (as described, for example, in EP 0 067 553 and U.S. Pat. No. 4,407,956), liposome-mediated transformation (as described, for example, in U.S. Pat. No. 4,536,475), and the like.

Other methods, such as microprojectile bombardment as described for corn by Fromm et al. (1990) and Gordon-Kamm et al. (1990), are suitable as well. Cells of monocotyledonous plants, such as the major cereals, can also be transformed using wounded and/or enzyme-degraded compact embryogenic tissue capable of forming compact embryogenic callus, or wounded and/or degraded immature embryos as described in WO92/09696. The resulting transformed plant cell can then be used to regenerate a transformed plant in a conventional manner.

The obtained transformed plant can be used in a conventional breeding scheme to produce more transformed plants with the same characteristics or to introduce the chimeric gene for reduction of the phenotypic expression of a nucleic acid of interest of the invention in other varieties of the same or related plant species, or in hybrid plants. Seeds obtained from the transformed plants contain the chimeric genes of the invention as a stable genomic insert.

It is a further object of the invention to provide eucaryotic cells, preferably plant cells and organisms (preferably plants) comprising the chimeric genes for the reduction of the phenotypic expression of a target nucleic acid as described in the invention.

It is a yet a further object of the invention to provide plant cells, comprising a nucleic acid of interest, which is normally capable of being expressed phenotypically, further comprising an RNA molecule with a nucleotide sequence which includes:

i. a sense nucleotide sequence of at least 10 consecutive nucleotides having between 75 and 100% sequence identity with at least part of the nucleotide sequence of the nucleic acid of interest; and ii. an antisense nucleotide sequence including at least 10 consecutive nucleotides, having between about 75% to about 100% sequence identity with the complement of the at least 10 consecutive nucleotides of the sense nucleotide sequence and capable of forming a double stranded RNA by association with the sense nucleotide sequence;

wherein the phenotypic expression of the nucleotide acid of interest is significantly reduced by the presence of the RNA molecule, when compared to the phenotypic expression of the nucleic acid of interest in the absence of the RNA molecule. The RNA molecule may be encoded by chimeric DNA. Preferred embodiments for the sense and antisense nucleotide sequence, particularly concerning length and sequence, are as mentioned elsewhere in this specification.

It will be appreciated that the methods and means described in the specification can also be applied in High Throughput Screening (HTS) methods, for the identification or confirmation of phenotypes associated with the expression of a nucleic acid sequence with hitherto unidentified function in a eucaryotic cell, particularly in a plant cell. Such a method comprises the steps of 1. selecting a target sequence within the nucleic acid sequence of interest with unidentified or non-confirmed function/phenotype when expressed. Preferably, if the nucleic acid has putative open reading frames, the target sequence should comprise at least part of one of these open reading frames. The length of the target nucleotide sequence may vary from about 10 nucleotides up to a length equaling the length (in nucleotides) of the nucleic acid of interest with unidentified function.

2. designing an RNA molecule comprising sense nucleotide sequence and antisense nucleotide sequence in accordance with the invention.

3. introducing the RNA molecule comprising both the sense and antisense nucleotide sequences designed on the basis of the target sequence, into a suited host cell, particularly a plant cell, comprising the nucleic acid with the nucleotide sequence with hitherto unidentified phenotype. The RNA can either be introduced directly, or can be introduced by means of a chimeric DNA comprising a promoter operative in the host cell of interest, particularly a plant-expressible promoter, and a DNA region functioning as a suitable 3' end formation and polyadenylation signal (terminator) functioning in the host cell, with in-between a DNA region which can be transcribed to yield the RNA molecule comprising the sense and antisense nucleotide sequence. The chimeric DNA can either be introduced transiently or integrated in the nuclear genome. The chimeric DNA can also be provided on a viral vector (see, e.g., WO 95/34668 and WO 93/03161)
4. observing the phenotype by a suitable method. Depending on the phenotype expected, it may be sufficient to observe or measure the phenotype in a single cell, but it may also be required to culture the cells to obtain an (organized) multicellular level, or even to regenerate a transgenic organism, particularly a transgenic plant.

In its most straightforward embodiment, the RNA molecule comprising both the sense and antisense nucleotide sequences to at least part of a nucleic acid of interest, suitable for the methods of the invention, can be obtained by cloning two copies of a DNA region with the selected target sequence in inverted repeat orientation (preferably separated by a short DNA region which does not contain a transcription termination signal, and encodes the spacer sequence) under a suitable promoter. This chimeric DNA is then either used as template DNA in an in vitro transcription method to generate the RNA molecule, which is introduced in the host cell, or the chimeric DNA itself is introduced in the host cell.

The methods and means of the invention can thus be used to reduce phenotypic expression of a nucleic acid in a eucaryotic cell or organism, particularly a plant cell or plant, for obtaining shatter resistance (WO 97/13865), for obtaining modified flower color patterns (EP 522 880, U.S. Pat. No. 5,231,020), for obtaining nematode resistant plants (WO 92/21757, WO 93/10251, WO 94/17194), for delaying fruit ripening (WO 91/16440, WO 91/05865, WO 91/16426, WO 92/17596, WO 93/07275, WO 92/04456, U.S. Pat. No. 5,545,366), for obtaining male sterility (WO 94/29465, WO89/10396, WO 92/18625), for reducing the presence of unwanted (secondary) metabolites in organisms, such as glucosinolates (WO97/16559) or chlorophyll content (EP 779 364) in plants, for modifying the profile of metabolites synthesized in a eucaryotic cell or organisms by metabolic engineering e.g. by reducing the expression of particular genes involved in carbohydrate metabolism (WO 92/11375, WO 92/11376, U.S. Pat. No. 5,365,016, WO 95/07355) or lipid biosynthesis (WO 94/18337, U.S. Pat. No. 5,530,192), for delaying senescence (WO 95/07993), for altering lignification in plants (WO 93/05159, WO 93/05160), for altering the fibre quality in cotton (U.S. Pat. No. 5,597,718), for increasing bruising resistance in potatoes by reducing polyphenoloxidase (WO 94/03607), etc.

The methods of the invention will lead to better results and/or higher efficiencies when compared to the methods using conventional sense or antisense nucleotide sequences and it is believed that other sequence-specific mechanisms regulating the phenotypic expression of target nucleic acids might be involved and/or triggered by the presence of the double-stranded RNA molecules described in this specification.

A particular application for reduction of the phenotypic expression of a transgene in a plant cell, inter alia, by antisense or sense methods, has been described for the restoration of male fertility, the latter being obtained by introduction of a transgene comprising a male sterility DNA (WO 94/09143, WO 91/02069). The nucleic acid of interest is specifically the male sterility DNA. Again, the processes and products described in this invention can be applied to these methods in order to arrive at a more efficient restoration of male fertility.

The methods and means of the invention, particularly those involving RNA molecules comprising a hairpin RNA and the encoding chimeric genes, have proven to be particularly suited for the modification of the composition of oil content in plants, particularly in seeds. Particularly preferred plants are crop plants used for oil production such as but not limited to oilseed rape (*Brassica juncea, napus, rapa, oleracea, campestris*), corn, cotton, groundnut, sunflower, castor beans, flax, coconut, linseed, soybean. Preferred target genes are the desaturase genes, particularly Δ12 desaturase encoding genes such as those encoded by the Fad2 genes, especially the genes whose nucleotide sequence can be found in the Genbank Database under accession number AF123460 (from *Brassica carinata*), AF12042841 (*Brassica rapa*), L26296 (*Arabidopsis thaliana*) or A65102 (*Corylus avellana*). It is clear that it is well within the reach of the person skilled in the art to obtain genes homologous to the disclosed fad2 genes from other species e.g. by hybridization and/or PCR techniques.

Preferred embodiments for the configuration of sense and antisense nucleotide sequences, particularly concerning length and sequence are as mentioned elsewhere in this specification. Also, preferred embodiments for chimeric genes encoding hairpin containing RNA molecules, particularly concerning promoter elements are as described elsewhere in the specification. For this application, it is particularly preferred that the promoters are seed-specific promoters.

In a preferred embodiment, the artificial hairpin RNA comprising RNA molecule thus comprises part of a Δ12 desaturase encoding ORF in sense orientation and a similar part in antisense orientation, preferably separated by a spacer sequence. In a particularly preferred embodiment the artificial hairpin RNA (or its encoding chimeric gene) comprises the nucleotide sequence of SEQ ID No 6 or a similarly constructed nucleotide sequence based on the aforementioned *Brassica* fad2 genes.

Preferably the chimeric gene encoding the artificial hairpin RNA is transcribed under control of a seed-specific promoter, particularly under control of the FPI promoter as described elsewhere in this application.

A reduction of the expression of Δ12 desaturase gene in oil containing plants leads to increase in oleic acid and a concomitant decrease in linolenic acid and linoleic acid. A higher frequency of plants with oil wherein the increase in oleic acid and concomitant decrease in linolenic and linoleic acid is significant is found using the means and methods of the invention than in transgenic plants harboring common cosuppression constructs. Moreover the absolute levels of increase, respectively decrease are higher respectively lower than in transgenic plants harboring common cosuppression constructs.

Using the means and methods of the invention, it is thus possible to obtain plants and seeds, comprising an oil of which the composition after crushing and extracting has an increased oleic acid content (expressed as a percentage of the total fatty acid composition), particularly a three fold increase, when compared with control plants.

It is expected that using the methods and means of the invention, transgenic *Brassica* plant can be obtained, whose seeds comprise an oil wherein the oleic acid content exceeds 90% of the total fatty acid contents.

The methods and means of the invention will be especially suited for obtaining virus resistance, particularly extreme virus resistance, in eucaryotic cells or organisms, particularly in plant cells and plants. A non-limiting list of viruses for plants against which resistance can be obtained, is represented in Table I.

The methods and means of the invention further allow the use of viral genes, hitherto unused for obtaining virus resistant plants in addition to the commonly used coat protein genes or replicase genes. Such different viral genes include protease encoded genes (Pro) genome linked protein (Vpg) encoding genes, cytoplasmic inclusion body encoding genes (CI) as target nucleic acid sequences for obtaining virus resistant plants.

It is clear that the invention will be especially suited for the reduction of phenotypic expression of genes belonging to multigene families.

It is also clear that the methods and means of the invention are suited for the reduction of the phenotypic expression of a nucleic acid in all plant cells of all plants, whether they are monocotyledonous or dicotyledonous plants, particularly crop plants such as but not limited to corn, rice, wheat, barley, sugarcane, cotton, oilseed rape, soybean, vegetables (including chicory, brassica vegetables, lettuce, tomato), tobacco, potato, and sugarbeet, but also plants used in horticulture, floriculture or forestry. The means and methods of the invention will be particularly suited for plants which have complex genomes, such as polyploid plants.

It is expected that the chimeric RNA molecules produced by transcription of the chimeric genes described herein, can spread systemically throughout a plant, and thus it is possible to reduce the phenotypic expression of a nucleic acid in cells of a non-transgenic scion of a plant grafted onto a transgenic stock comprising the chimeric genes of the invention (or vice versa) a method which may be important in horticulture, viticulture or in fruit production.

The following non-limiting Examples describe the construction of chimeric genes for the reduction of the phenotypic expression of a nucleic acid of interest in a eucaryotic cell and the use of such genes. Unless stated otherwise in the Examples, all recombinant DNA techniques are carried out according to standard protocols as described in Sambrook et al. (1989) *Molecular Cloning: A Laboratory Manual*, Second Edition, Cold Spring Harbor Laboratory Press, NY and in Volumes 1 and 2 of Ausubel et al. (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

Throughout the description and Examples, reference is made to the following sequences:

SEQ ID No 1: sequence of the Potato virus Y fragment of the Nia gene used for the construction of various sense and antisense constructs, for obtaining virus resistance.

SEQ ID No 2: sequence of the coding region of the Gusd CoP construct of Example 1.

SEQ ID No 3: sequence of a modified 5' untranslated region (5'UTR) from Johnsongrass mosaic virus SEQ ID No 4: sequence of the Subterranean clover virus promoter No 4 with S7 enhancer.

SEQ ID No 5: sequence of the Subterranean clover virus double enhancer promoter No 4.

SEQ ID No 6: sequence of the CoP construct for the Δ12 desaturase gene expression inhibition.

SEQ ID No 7: sequence of the *Flaveria trinervia* pyruvate orthophosphate dikinase intron The following free text is included in the sequence listing:

| | |
|---|---|
| <223> | fragment of the NIa ORF |
| <223> | Description of Artificial Sequence: coding region of the Gusd CoP construct |
| <223> | deficient Gus coding region |
| <223> | antisense to the 5' end of the Gus coding region |
| <223> | Description of Artificial Sequence: 5' UTR of Johnson mosaic virus |
| <223> | Description of Artificial Sequence: Subterannean clover virus S4 promoter with S7 enhancer |
| <223> | Description of Artificial Sequence: subterranean clover virus promoter S4 with S4 enhancer |
| <223> | Description of Artificial Sequence: coding sequence of the desaturase CoP construct |
| <223> | corresponding to the 5' end of the delta12-desaturase (fad2) coding region, in sense orientation |
| <223> | corresponding to the 5' end of the delta12-desaturase (fad2) coding region, in anti sense orientation |
| <223> | Description of Artificial Sequence: intron 2 of the *Flaveria trinervia* puryvate orthophosphate dikinase |

The following examples are presented in order to more fully illustrate the preferred embodiments of the invention. They should in no way be construed, however, as limiting the broad scope of the invention.

Example 1

Experimental Procedures

Gene Construction

Standard gene cloning methods (Sambrook et al. 1989) were used to make the chimeric genes. A schematic representation of the constructs used is shown in FIGS. 1A and 1B.

The components for these constructs were:

Cauliflower mosaic virus 35S promoter from the Cabb-JI isolate(35S) (Harpster et al., 1988)

Octopine synthase terminator (ocs-t) (MacDonald et al., 1991)

Subterranean clover virus promoter No 4 (S4) (WO 9606932)

Subterranean clover virus terminator No 4 (s4t) (WO 9606932)

Subterranean clover virus double enhancer promoter No 4 (S4S4) (SEQ ID No 5)

Subterranean clover virus promoter No 4 with S7 enhancer (S7S4) (SEQ ID No 4)

Maize ubiquitin promoter (Ubi) (Christensen and Quail, 1996)

*Agrobacterium* tumour morphology 1 gene terminator (tm1') (Zheng et al., 1991)

the Nia gene of an Australian strain of Potato virus Y (Nia) (SEQ ID N° 1)

a dysfunctional β-glucuronidase open reading frame encoding DNA (Gusd)(SEQ ID No 2 from nucleotide 1 to nucleotide 1581)

a modified 5' untranslated region (5'UTR) from Johnsongrass mosaic virus (JGMV5') (SEQ ID No 3).

This contains insertion of a NcoI site at the ATG start codon followed by three stop codons in frame, and a PstI site (for insertion of the intron as in constructs 4 and 5 of FIG. 1A). In vector constructs 2 and 6 of FIG. 1A, the Gusd open reading frame is inserted in at the NcoI site, removing the stop codons; in all other constructs of FIG. 1A it is inserted downstream of the PstI site.

a castor bean catalase intron (Ohta et al., 1990) as modified by Wang et a. (1997) ("intron").

The chimeric genes were constructed by operably assembling the different parts as schematically indicated in FIG. 1A or FIG. 1B and inserting the obtained chimeric genes in the T-DNA vectors pART27 and pART7 vectors (Gleave, 1992) between the left T-DNA border and the chimeric plant expressible neo gene.

The DNA encoding a dysfunctional-glucuronidase open reading frame (GUSd) was obtained by deleting from a gus coding region the sequence between the two EcoRV restriction sites. For the construction of the chimeric gene encoding the RNA molecule comprising both sense and antisense nucleotide sequence to a β-glucuronidase gene, a sequence was added to the Gusd gene to be allow base pairing the 5'end over 558 bases resulting in a sequence as represented in SEQ ID No 2. This sequence was cloned between the maize ubiquitin promoter and the tm1' terminator and inserted in a T-DNA vector.

T-DNA vectors were constructed which comprised a first and a second chimeric virus resistance gene, wherein the first chimeric gene consisted of:
1. a CaMV 35S promoter sequence, coupled to
2. in sense orientation, the nucleotide sequence from PVY encoding either
   Vpg protein (see e.g., Genbank Accession Nr ZZ9526 from nucleotide 1013 to nucleotide 1583), or
   part of the Cl protein (see e.g., Genbank Accession Nr M95491 from nucleotide 3688 to nucleotide 4215) or
   Protease (Pro) (see e.g., EMBL Accession Nr D00441 from nucleotide 5714 to nucleotide 7009), followed by
3. the S4 terminator from subterranean clover mosaic virus, as described above.

The second chimeric gene consists of
1. a S4 promoter as described above, coupled to
2. in anti-sense orientation, the nucleotide sequence from PVY encoding either
   Vpg protein, or
   Cl protein or
   Protease, followed by
3. the octopine synthase terminator as described above.

The sense and antisense sequences within one T-DNA vector were derived from the same PVY coding region.

Also, T-DNA vectors were constructed for use in altering the fatty acid composition in oil (see FIG. 2), comprising
1. a FP1 promoter (truncated seed specific napin promoter, containing sequences between −309 and +1, as described in Stalberg et al; linked to
2. the nucleotide sequence of SEQ ID No 6, comprising the 480 bp located 5' in the ORF encoding the Δ12 desaturase from *Arabidopsis thaliana* (Fad2) in sense orientation and in antisense orientation, linked by a 623 bp spacer sequence; followed by
3. the terminator from the nopaline synthase gene.

In addition, T-DNA vectors were constructed to evaluate the influence of a presence of an intron sequence in the chimeric genes encoding CoP constructs. To this end, constructs were made comprising:

1. a CamV35S promoter, followed by
2. the protease encoding ORF from PVY (see above) in sense orientation;
3. the sequence of SEQ ID No 7 (encoding the *Flaveria trinervia* pyruvate orthophospate dikinase intron 2)
4. the protease encoding ORF from PVY in antisense orientation; and
5. the octopine synthase gene terminator.

Plant Transformation

*Nicotiana tabacum* (W38) tissue was transformed and regenerated into whole plants essentially as described by Landsman et al. (1988). Rice (*Oryza sativa*) was transformed essentially as described by Wang et al. (1997).

Rice Supertransformation

Mature embryos from a rice plant expressing GUS and hygromycin phosphotransferase (HPT) activity were excised from mature seed and placed on callus inducing media for 7 weeks. Calli were recovered from these cultures, incubated with *Agrobacteria* containing various binary vector constructs for 2 days, then placed on callusing media containing hygromycin, bialaphos and Timentin™. During the next four weeks hygromycin and bialaphos resistant calli developed. These callus lines were maintained on hygromycin and bialaphos containing media for a further 2 months before being assayed for GUS activity.

GUS Assay

Rice calli were tested for GUS activity using the histochemical stain X-glucuronide or the fluorogenic substrate 4-methyl-umbeliferone glucuronide (MUG) essentially as described by Jefferson et al. (1987).

Example 1

Comparison of Chimeric Genes Comprising Only Antisense, Only Sense, or Both Sense and Antisense (Complimentary Pair (CoP)) Sequence for Reduction in Phenotypic Expression of an Integrated β-Glucuronidase Gene Transgenic rice tissue expressing β-glucuronidase (GUS) from a single transgene (and hygromycin resistance from a hph gene) (lines V10-28 and V10-67) was supertransformed using vectors that contained the bar gene conferring phosphinothricin resistance and various sense, antisense and CoP constructs (see FIG. 1A) derived from a crippled GUS (GUSd) gene. The supertransformed tissue was maintained on hygromycin and bialaphos selection media for 3 weeks then analyzed for GUS activity. A crippled GUS gene was used so that expression from this gene would not be superimposed on the endogenous GUS activity.

The figures in Table 2 represent the rate of MU production measured by absorption at 455 nm, with excitation at 365 nm of 1.5 µg of total protein in a reaction volume of 200 µl. The rate was measured over 30 min at 37° C. The reading for non-transgenic rice calli was 0.162. The figures in bracket which follow the description of the introduced construct refer to FIG. 1A.

The results (Table 2) showed that supertransformation with the binary vector containing the bar gene without the GUSd gene had no silencing effect on the endogenous GUS activity. Supertransformation with GUSd in a sense or antisense orientation, with or without an intron or an early stop codon, showed some degree of reduction (in about 25% of the analyzed calli) of the endogenous GUS activity (see last two rows in Table 2 representing the percentage of analyzed calli with a MUG assay reading of less than 2.000). However, supertransformation with a CoP construct gave in about 75% to 100% of the analyzed calli, reduction of the endogenous GUS activity. This CoP construct was designed so that the 3' end of the mRNA produced could form a duplex with the 5' end of the transcript to give a "panhandle" structure.

These data show that a complimentary pair can be made using one self-annealing transcript, that this design is much more effective than a conventional sense or antisense construct, and that the approach can be used to reduce the phenotypic expression of genes present in a plant cell.

TABLE 2

MUG assay of Supertransformed Rice Calli

| | Vector cassette (1) | Sense (2) | Sense + Stop (3) | Sense + stop + intron (4) | Antisense + stop + intron (5) | Inverted repeat CoP (6) |
|---|---|---|---|---|---|---|
| V10-28 | 121.0 | 97.45 | 38.43 | 38.88 | 0.290 | 0.565 |
| | 45.58 | 6.637 | 64.16 | 115.5 | 0.572 | 0.316 |
| | 99.28 | 71.60 | 149.2 | 133.0 | 37.2 | 0.351 |
| | 26.17 | 0.224 | 0.955 | 98.46 | 53.94 | 0.210 |
| | 92.21 | 0.321 | 68.32 | 0.502 | 105.5 | 0.701 |
| | 108.8 | 5.290 | 105.6 | 39.35 | 56.73 | 0.733 |
| | 6.432 | 0.9460 | 136.6 | 1.545 | 60.36 | 2.103 |
| | 90.80 | 32.44 | 140.4 | 10.36 | 71.12 | 119.8 |
| | 98.24 | 128.8 | 62.38 | 111.6 | 13.17 | 0.717 |
| | 93.76 | 31.28 | 17.79 | 14.42 | 0.424 | 0.398 |
| | | 5.023 | | 88.06 | 26.98 | 0.315 |
| | | 40.27 | | 52.28 | 115.5 | 0.270 |
| | | 36.40 | | 30.26 | 149.7 | 16.78 |
| | | 53.24 | | 107.5 | 66.75 | 67.28 |
| | | 29.97 | | 26.75 | 145.8 | 0.217 |
| | | 89.06 | | 105.1 | 0.534 | 0.208 |
| | | 0.256 | | 135.1 | 9.4 | |
| | | 68.23 | | 95.04 | 35.33 | |
| | | 5.481 | | 71.5 | | |
| V10-67 | 318.8 | 93.43 | 0.199 | 31.82 | 1.395 | 0.472 |
| | 109.5 | 73.19 | 0.197 | 58.08 | 152.4 | 0.256 |
| | 30.35 | 128.1 | 0.157 | 56.32 | 67.42 | 0.296 |
| | 40.04 | 1.506 | 128 | 44.62 | 12.11 | 0.452 |
| | 228 | 140.6 | 130.3 | 0.454 | 0.668 | 0.422 |
| | 23.05 | 1.275 | 196.2 | 17.32 | 23.34 | 0.196 |
| | 241.2 | 0.272 | 12.43 | 73.2 | 76.10 | 0.294 |
| | 118.5 | 0.209 | 140.0 | 20.32 | 130.1 | 0.172 |
| | 11.27 | 42.05 | 90.13 | 107.4 | 0.841 | 0.436 |
| | 110.6 | 117.5 | 157.4 | 0.453 | 66.12 | 0.398 |
| | 19.29 | 118.9 | 0.518 | 87.81 | 136.9 | 0.242 |
| | 121.0 | 21.44 | 0.231 | 0.299 | 67.92 | |
| | 115.1 | 155.0 | 116.1 | 0.206 | 50.32 | |
| | 77.1 | 190.9 | 43.18 | 12.47 | 170.3 | |
| | 106.1 | 0.773 | 31.06 | 0.213 | 108.9 | |
| | 73.12 | 0.146 | | 11.15 | 1.241 | |
| | 29.97 | | | 19.22 | 4.092 | |
| | 50.11 | | | | 169.6 | |
| | 80.34 | | | | 76.88 | |
| | 117.8 | | | | 22.08 | |
| | 159.1 | | | | 91.6 | |
| | 67.52 | | | | 7.855 | |
| | 92.32 | | | | 69.76 | |
| | 27.97 | | | | 0.822 | |
| V10-28 | 0% | 21% | 10% | 10.5% | 22% | 75% |
| V10-67 | 0% | 37.5% | 33% | 29.5% | 21% | 100% |

Example 2

Comparison of the Efficiency of Using Chimeric Genes Comprising Only Antisense Genes, Only Sense Genes, or Both Genes Simultaneously for Obtaining Virus Resistance in Transgenic Plants Gene constructs were made using the PVY protease encoding sequence (SEQ ID No 1) in a sense orientation, an antisense orientation and in a complimentary pair (CoP) orientation, where the T-DNA comprised both the sense and antisense chimeric genes each under control of their own promoter. In all three arrangements the CaMV35S promoter was used. Five different versions of CoP constructs were made in which the second promoter was either the CaMV35S promoter, the S4 promoter, the double S4 promoter, the S7 enhanced S4 promoter, or the vascular specific rolC promoter (see FIG. 1B).

These constructs were transformed into tobacco (via Agrobacterium mediated DNA transfer) and approximately 25 independently transformed plants were recovered per chimeric gene construct. The transgenic plants were transferred to soil and maintained in the greenhouse. About 1 month after transplanting to soil, the plants were inoculated manually with potato virus Y, using standard application methods. Two and four weeks later the plants were scored for virus symptoms. The results (Table 3) showed that after 1 month, 2 on 27 plants comprising only the sense gene, and 1 on 25 plants comprising only the antisense gene showed no symptoms.

In contrast respectively 11 on 24 (35S-Nia/S4-antisense-Nia construct), 7 on 25 (35S-Nia/RolC-antisenseNia construct), 10 on 27 (35S-Nia/35S-antisenseNia), 7 on 26 (35S-Nia/S4S4-antisenseNia construct), and 7 on 25 (35S-Nia/S7S4-antisenseNia construct) plants which contained both the sense and antisense genes, showed no symptoms. Plants that showed no symptoms were considered to be showing extreme resistance to PVY. They continued to show no symptoms for a further 2 months of monitoring (indicated as Extreme Resistant (ER) in Table 3). Some other plants, particularly those containing CoP constructs, showed a delay and restriction of symptoms. They showed no symptoms 2 weeks after inoculation but showed some minor lesions in some plants after 4 weeks. These plants were clearly much less effected by PVY than non-transgenic or susceptible tobaccos and were scored as resistant (indicated as ER* in Table 3).

TABLE 3

Resistance to PVY infection of transgenic tobacco plants comprising either the sense chimeric PVY protease construct, the antisense chimeric PVY protease construct, or both (different CoP constructs).

| Sense gene | Antisense gene | Extreme Resistant plants (ER) | "Resistant" plants (ER*) | Total number of transgenic plants |
|---|---|---|---|---|
| 35S-Nia | | 2 | 2 | 27 |
| | 35S-AntisenseNia | 1 | 0 | 25 |
| 35S-Nia | 35S-AntisenseNia | 10 | 2 | 27 |
| 35S-Nia | S4-AntisenseNia | 11 | 2 | 24 |
| 35S-Nia | RolC-AntisenseNia | 7 | 3 | 25 |
| 35S-Nia | S4S4-AntisenseNia | 7 | 7 | 26 |
| 35S-Nia | S7S4-AntisenseNia | 7 | 4 | 25 |

The data show that using CoP constructs results in a much higher frequency of transgenic plants with extreme resistance and resistance than by using either sense or antisense constructs alone.

Next, the copy number of the transgenes in the virus resistant transgenic plants was determined. Therefore, DNA was extracted from all the transgenic plants showing extreme resistance or resistance. DNA was also extracted from five susceptible plants for each construct. The DNA was examined for gene copy number using Southern analysis. The data (Table 4) showed that the genomes of some of the CoP plants showing extreme resistance, particularly the 35S-Nia/S4-AntisenseNia plants, only contained a single copy of the gene construct.

TABLE 4

Copy number of transgenes comprising sense chimeric PVY protease construct, the antisense chimeric PVY protease construct, or both (different CoP constructs) in extreme resistant, resistant and susceptible plants.

| Sense gene | Antisense gene | Extreme Resistant plants (ER) | "Resistant" plants (ER*) | Susceptible plants |
|---|---|---|---|---|
| 35S-Nia | | 6 | 1 | 1/1/1/1/1 |
| | 35S-AntisenseNia | 4 | — | 1/8/0/2/1 |
| 35S-Nia | 35S-AntisenseNia | 3/1/2/3/6/3/2/4/2/3 | 1/1 | 1/2/2/6/1 |
| 35S-Nia | S4-AntisenseNia | 2/4/1/3/2/4/6/1/1/3/1 | 2/6 | 5/8/2/3 |
| 35S-Nia | RoIC-AntisenseNia | 6/7/6/7/7/7/6 | 2/1 | 2/2/2/1/2 |
| 35S-Nia | S4S4-AntisenseNia | 1/2/4/5/2/2/2 | 1/1/2/1/1/1 | 1/1/7/1/1 |
| 35S-Nia | S7S4-AntisenseNia | 2/4/12/5/2/2/7 | 3/2/1/2 | 1/1/3/1/1 |

Example 3

Inheritance of Extreme Resistance in Plants from Example 2

Plants from Example 2 were allowed to self-fertilize and their seeds were collected. Seeds originating from plants showing extreme resistance and low transgene copy number for CoP constructs 35S-Nia/S4-AntisenseNia and 35S-Nia/35S-AntisenseNia, and seeds from the sense and the antisense plants showing extreme resistance, were germinated and grown in the glasshouse. Plants were also grown from seed collected from two susceptible CoP lines, two susceptible sense gene only lines and two susceptible antisense gene only lines. Twenty plants from each line were selected for overall uniformity of size and development stage, put into individual pots, allowed to recover for one week, then inoculated with PVY. The plants were scored for virus symptoms 2, 4, and 7 weeks after inoculation. The results (Table 5) showed that all eight plant lines of 35S-Nia/S4-antisenseNia and 35S-Nia/35S-antisenseNia containing one or two gene copies showed an about 3:1 segregation ratio of extreme resistance:susceptible. The progeny of the single antisense gene only line that had given extreme resistance at $T_0$, and the progeny of the extremely resistant sense plant containing one gene copy, gave abnormal segregation ratios (2:18; ER:susceptible). The progeny of the one sense plant that gave extreme resistance and contained 6 gene copies gave a ~3:1 ratio (ER:susceptible). All the progeny of the susceptible $T_0$ plants showed complete susceptibility to PVY.

These data show extreme resistance from CoP constructs gives stable expression of the resistance which is inherited in a Mendelian way. This also indicates that, in these lines the PVY CoP gene loci are ~100% effective at conferring extreme resistance whereas the transgene loci in the antisense line and one of the two sense lines are only partially effective at conferring extreme resistance.

Example 4

Extreme Virus Resistant Transgenic Tobacco with Different Components (Sense Gene and Antisense Gene) in Different Loci within the Transgenic Plant PVY susceptible plants containing the sense transgene (which contained single transgene copies; see Table 6) were crossed with PVY susceptible plants containing the antisense transgene (which had also been analyzed for copy number by Southern analysis; see Table 6). Twenty of the resulting progeny per cross were propagated in the glasshouse, then inoculated with PVY and scored for virus infection as described in Example 2. The progeny from the crosses (between single gene/loci containing plants) would be expected to be in the following ratio: ¼ sense gene alone, ¼ antisense gene alone, ¼ comprising both sense and antisense genes, and ¼ comprising no genes at all. The results (Table 4) show that, with one exception, a proportion of the progeny from all the successful crosses showed extreme resistance, whereas none of the progeny from selfed sense or selfed antisense plants showed extreme resistance. The one cross that gave no extremely resistant progeny was derived from the parent plant Antisense 2 (As2) which contained 8 copies of the antisense gene. All twenty progeny plants from crosses Sense 1 (S1)(male)×Antisense 1 (As1) (female) and Sense 3 (S3) (female)×Antisense 4 (As4) (male) were examined by Southern analysis. The results showed that in both crosses, the plants that showed extreme resistance (or in one case resistance) contained both the sense and antisense genes, whereas plants with no transgenes (nulls), or sense or antisense genes alone, were all susceptible to PVY. To further confirm this absolute correlation between the presence of a complimentary pair (sense with antisense genes) within a plant and extreme resistance, all progeny plants showing extreme resistance were ana-

TABLE 5

| | | 35S Sense Nia and S4 Antisense Nia | | 35S Sense Nia and S4 Antisense Nia | | 35S Sense Nia | | 35S Antisense Nia | |
|---|---|---|---|---|---|---|---|---|---|
| | | Copy N° | T1 ER:S | Copy N° | T1 ER:S | Copy N° | T1 ER:S | Copy N° | T1 ER:S |
| ER plant | 1 | 1 | 15:5 | 1 | 16:4 | 6 | 17:3 | 4 | 2:18 |
| | 2 | 1 | 12:8 | 2 | 15:5 | 1 | 2:18 | | |
| | 3 | 1 | 14:6 | 2 | 16:4 | | | | |
| | 4 | 1 | 15:5 | 2 | 16:4 | | | | |
| Susceptible Plant | 1 | 8 | 0:20 | 1 | 0:20 | 1 | 0:20 | 1 | 0:20 |
| | 2 | 2 | 0:20 | 1 | 0:20 | 1 | 0:20 | 8 | 0:20 | lyzed by Southern blots. The results showed that every extremely resistant or resistant plant contained both sense and antisense genes.

These data show that a complimentary pair gives resistance or extreme resistance even when the genes encoding the sense and antisense genes are not co-located in the genome. The "complimentary pair phenomenon" is not simply due to increased transgene dosage as it would be expected that ¼ of the selfed progeny would be homozygous and thus have double the gene dosage, yet they were susceptible.

TABLE 6

PVY resistance of the progeny plants resulting from crosses between susceptible transgenic tobacco plants comprising the 35S-senseNia gene (S-lines) and susceptible transgenic tobacco plants comprising the 35S-antisenseNia gene (As-lines).

| Male parent | Female parent | Extreme Resistant plants (ER) | "Resistant" plants (ER*) |
|---|---|---|---|
| S1 | As1 | 8 | |
| S1 | As4 | 6 | 5 |
| S2 | As4 | 1 | 3 |
| S3 | As4 | 3 | 3 |
| S4 | As1 | 7 | 1 |
| S3 | As5 | 1 | 2 |
| S4 | As2 | 0 | |
| S4 | As4 | 2 | 0 |
| S5 | As4 | 9 | 4 |
| S5 | As5 | 2 | 3 |
| As4 | As4 | 0 | |
| As5 | As5 | 0 | |
| S2 | S2 | 0 | |
| S4 | S4 | 0 | |

Extreme resistant plants showed no symptoms of PVY infection after 7 weeks. Resistant plants showed very minor lesions 7 weeks after PVY infection. S1, S2, S3, S4 and S5 are PVY susceptible transgenic tobacco plants comprising the 35S-senseNia gene construct which all have one copy of the transgene integrated.

As1, As2, As4 and As5 are PVY susceptible transgenic tobacco plants comprising the 35S-antisenseNia gene construct which have respectively 1, 8, 2 and 1 copies of the transgene integrated.

Example 5

Evaluation of the Use of Different Viral Genes as Target Nucleic Acid Sequences in obtaining Extreme Virus Resistant Genes The T-DNA vectors comprising first and second chimeric virus resistance genes based on sequences derived from the coding region for protease, Vpg or Cl proteins from PVY as described in this application, were used to obtain transformed tobacco plants, which were subsequently challenged with PVY. The results are summarized in the following table:

TABLE 7

| Construct | Number of immune plants/Number of independent transgenic plants | |
|---|---|---|
| | Replica 1 | Replica 2 |
| 35S-Pro sense/S4-Pro antisense | 11/24 | 7/25 |
| 35S-Vpg sense/S4-Vpg antisense | 8/20 | 6/18 |
| 35S-Cl sense/S4-Cl antisense | 2/23 | 1/20 |

Example 6

Intron Enhanced Silencing

The T-DNA vectors comprising the chimeric genes encoding the CoP constructs wherein an intron (*Flaveria trinervia* pyruvate orthophosphate dikinase intron 2) has been inserted in either the sense orientation or the antisense orientation, between the sense and antisense sequences corresponding to the protease encoding ORF from PVY (as described elsewhere in this application) were used to obtain transformed tobacco plants, which were subsequently challenged with PVY. The results are summarized in the following table:

TABLE 8

| Construct | Number of immune plants/Number of independent transgenic plants |
|---|---|
| 35S-Pro(sense)-intron(sense)-Pro(antisense)-Ocs-t | 22/24 |
| 35S-Pro(sense)-intron(antisense)-Pro(antisense)-Ocs-t | 21/24 |

Example 7

Modifying Oil Profile Using CoP Constructs in *Arabidopsis*

T-DNA vectors for modifying the fatty acid composition in oil, extracted from crushed seeds as described elsewhere in this application were used to introduce the chimeric gene encoding the CoP construct for reducing the expression (see FIG. 2A; SEQ ID No 6) the Δ12 desaturase gene (Fad2) in *Arabidopsis thaliana*.

For comparison of the efficiency, transgenic *Arabidopsis* plants were generated wherein the Fad2 gene expression was reduced by a plain cosuppression construct, comprising the FPI seed-specific promoter coupled to the complete ORF from the Δ12 desaturase gene (Fad2) in *Arabidopsis thaliana* and the nopaline synthase promoter (see FIG. 2B).

As control plants, transgenic *Arabidopsis* transformed by unrelated T-DNA constructs were used.

Seeds were harvested, crushed and extracted and the percentage of the major fatty acids in the oil was determined by methods available in the art. The results, which are the mean of two readings, are summarized in Table 9.

TABLE 9

| | Peak Names | | | | | | | | | | | | |
|---|---|---|---|---|---|---|---|---|---|---|---|---|---|
| Sample Name | Myristic | Palmitic | Palmitoleic | Stearic | Oleic | Linoleic | Linolenic | 20:0 | 20:1 | 22:0 | 22:1 | 24:0 | C18:1/(C18:2 + C18:3) |
| Hairpin 1.1 | 0.00 | 6.06 | 0.52 | 3.21 | 56.65 | 7.50 | 6.82 | 1.46 | 16.02 | 0.00 | 1.76 | 0.00 | 3.95 |
| Hairpin 1.2 | 0.12 | 6.86 | 0.39 | 3.40 | 51.28 | 10.00 | 8.73 | 1.64 | 15.60 | 0.00 | 1.97 | 0.00 | 2.74 |

TABLE 9-continued

| Sample Name | Myristic | Palmitic | Palmitoleic | Stearic | Oleic | Linoleic | Linolenic | 20:0 | 20:1 | 22:0 | 22:1 | 24:0 | C18:1/(C18:2 + C18:3) |
|---|---|---|---|---|---|---|---|---|---|---|---|---|---|
| Hairpin 1.3 | 0.11 | 8.47 | 0.50 | 3.49 | 21.64 | 28.99 | 18.51 | 2.02 | 14.19 | 0.00 | 2.09 | 0.00 | 0.46 |
| Hairpin 1.4 | 0.00 | 6.14 | 0.50 | 3.37 | 51.70 | 9.77 | 8.02 | 1.73 | 16.04 | 0.00 | 2.05 | 0.67 | 2.91 |
| Hairpin 2.1 | 0.06 | 5.19 | 0.43 | 3.33 | 54.84 | 5.52 | 7.76 | 1.77 | 18.50 | 0.34 | 1.83 | 0.45 | 4.13 |
| Hairpin 2.2 | 0.04 | 7.67 | 0.46 | 3.75 | 19.60 | 28.29 | 18.64 | 2.55 | 15.96 | 0.19 | 2.28 | 0.56 | 0.42 |
| Hairpin 3.1 | 0.00 | 7.99 | 0.53 | 3.62 | 19.52 | 28.41 | 19.24 | 2.32 | 15.14 | 0.00 | 2.23 | 0.99 | 0.41 |
| Hairpin 3.2 | 0.09 | 7.00 | 0.54 | 3.69 | 49.02 | 11.03 | 9.64 | 1.71 | 14.94 | 0.00 | 1.72 | 0.62 | 2.37 |
| Hairpin 3.3 | 0.00 | 5.68 | 0.49 | 3.98 | 46.19 | 12.82 | 9.71 | 2.10 | 16.70 | 0.00 | 1.94 | 0.39 | 2.05 |
| Hairpin 3.4 | 0.17 | 7.19 | 0.77 | 3.69 | 45.90 | 11.86 | 10.65 | 1.84 | 15.39 | 0.00 | 1.90 | 0.65 | 2.04 |
| Hairpin 3.5 | 0.00 | 6.45 | 0.48 | 3.26 | 51.76 | 8.13 | 10.04 | 1.51 | 16.08 | 0.00 | 1.92 | 0.36 | 2.85 |
| Hairpin 3.6 | 0.08 | 7.51 | 0.23 | 3.59 | 19.97 | 29.13 | 20.12 | 2.15 | 14.54 | 0.29 | 2.02 | 0.36 | 0.41 |
| Hairpin 3.7 | 0.14 | 7.20 | 0.78 | 2.90 | 26.37 | 24.81 | 17.18 | 1.92 | 15.50 | 0.36 | 2.30 | 0.53 | 0.63 |
| Hairpin 3.8 | 0.11 | 6.34 | 0.46 | 3.23 | 38.58 | 15.25 | 13.54 | 1.89 | 16.91 | 0.00 | 2.36 | 1.34 | 1.34 |
| Hairpin 3.9 | 0.00 | 6.47 | 0.49 | 3.32 | 47.59 | 11.44 | 9.63 | 1.68 | 15.96 | 0.00 | 1.88 | 1.55 | 2.26 |
| Hairpin 3.10 | 0.00 | 6.77 | 0.56 | 3.48 | 53.30 | 7.57 | 9.34 | 1.55 | 15.65 | 0.00 | 1.79 | 0.00 | 3.15 |
| Hairpin 3.11 | 0.00 | 7.05 | 0.59 | 3.61 | 53.62 | 8.87 | 8.36 | 1.55 | 14.35 | 0.00 | 1.99 | 0.00 | 3.11 |
| Hairpin 3.12 | 0.05 | 8.32 | 0.36 | 3.85 | 18.48 | 29.24 | 19.94 | 2.48 | 14.75 | 0.00 | 2.28 | 0.26 | 0.38 |
| Hairpin 4.1 | 0.09 | 6.97 | 0.59 | 3.61 | 53.64 | 8.40 | 8.44 | 1.60 | 15.00 | 0.00 | 1.66 | 0.00 | 3.19 |
| Hairpin 4.2 | 0.07 | 6.81 | 0.22 | 3.27 | 55.06 | 9.16 | 8.71 | 1.26 | 13.63 | 0.19 | 1.33 | 0.30 | 3.08 |
| Hairpin 4.3 | 0.04 | 6.81 | 0.50 | 3.47 | 46.21 | 10.67 | 11.52 | 1.81 | 16.50 | 0.00 | 1.88 | 0.58 | 2.08 |
| Hairpin 5.1 | 0.00 | 8.30 | 0.23 | 3.71 | 17.72 | 28.92 | 20.63 | 2.38 | 14.77 | 0.00 | 2.41 | 0.92 | 0.36 |
| Hairpin 5.2 | 0.19 | 7.15 | 1.55 | 3.56 | 44.58 | 11.44 | 11.59 | 1.77 | 15.67 | 0.00 | 1.84 | 0.65 | 1.94 |
| Hairpin 5.3 | 0.10 | 6.49 | 0.40 | 3.72 | 54.19 | 7.01 | 7.89 | 1.74 | 15.91 | 0.00 | 1.92 | 0.62 | 3.64 |
| Hairpin 5.5 | 0.12 | 6.58 | 0.51 | 3.84 | 54.48 | 6.16 | 7.23 | 1.77 | 16.50 | 0.42 | 1.90 | 0.48 | 4.07 |
| Hairpin 5.6 | 0.00 | 6.67 | 0.50 | 3.66 | 46.32 | 11.56 | 10.48 | 1.83 | 15.99 | 0.00 | 2.15 | 0.84 | 2.10 |
| Hairpin 5.7 | 0.00 | 5.50 | 0.51 | 3.58 | 57.33 | 4.75 | 5.91 | 1.75 | 18.03 | 0.00 | 1.88 | 0.76 | 5.38 |
| Hairpin 5.8 | 0.16 | 6.55 | 1.53 | 3.54 | 48.52 | 9.91 | 8.97 | 1.78 | 16.39 | 0.00 | 1.84 | 0.81 | 2.57 |
| Hairpin 6.1 | 0.10 | 6.35 | 0.57 | 3.48 | 59.00 | 4.77 | 6.26 | 1.48 | 15.95 | 0.00 | 1.80 | 0.25 | 5.35 |
| Hairpin 6.2 | 0.10 | 7.98 | 0.37 | 4.06 | 20.96 | 29.01 | 18.69 | 2.38 | 13.63 | 0.20 | 2.03 | 0.60 | 0.44 |
| Hairpin 6.5 | 0.08 | 6.21 | 0.63 | 3.61 | 60.05 | 5.07 | 5.27 | 1.55 | 15.20 | 0.00 | 1.69 | 0.66 | 5.81 |
| Columbia pBin 19 control | 0.08 | 8.81 | 0.47 | 3.51 | 17.07 | 30.31 | 20.94 | 1.78 | 14.56 | 0.00 | 2.17 | 0.28 | 0.33 |
| Cosuppresion 1.1 | 0.08 | 8.16 | 0.62 | 3.71 | 26.16 | 23.77 | 18.15 | 2.06 | 14.65 | 0.17 | 1.89 | 0.57 | 0.62 |
| Cosuppresion 1.2 | 0.00 | 8.49 | 0.53 | 3.65 | 17.90 | 29.93 | 20.36 | 2.34 | 14.25 | 0.00 | 2.33 | 0.23 | 0.36 |
| Cosuppresion 1.3 | 0.07 | 6.65 | 0.40 | 3.42 | 38.34 | 15.25 | 14.16 | 1.91 | 17.19 | 0.31 | 1.94 | 0.35 | 1.30 |
| Cosuppresion 1.4 | 0.00 | 8.22 | 0.57 | 3.82 | 18.27 | 28.82 | 19.63 | 2.56 | 14.83 | 0.00 | 2.46 | 0.83 | 0.38 |
| Cosuppresion 1.5 | 0.00 | 7.51 | 0.52 | 3.84 | 34.59 | 17.90 | 14.64 | 2.18 | 16.27 | 0.00 | 2.02 | 0.54 | 1.06 |
| Cosuppresion 1.6 | 0.07 | 7.44 | 0.47 | 3.16 | 23.97 | 27.32 | 17.29 | 2.03 | 15.52 | 0.18 | 2.22 | 0.33 | 0.54 |
| Cosuppresion 2.1 | 0.07 | 7.46 | 0.43 | 3.00 | 23.91 | 27.21 | 17.79 | 1.84 | 15.27 | 0.30 | 2.14 | 0.58 | 0.53 |
| Cosuppresion 2.2 | 0.00 | 8.19 | 0.55 | 4.22 | 18.59 | 28.31 | 18.80 | 2.77 | 15.51 | 0.00 | 2.46 | 0.58 | 0.39 |
| Cosuppresion 2.3 | 0.00 | 8.71 | 0.47 | 3.48 | 19.21 | 30.06 | 19.49 | 2.03 | 13.78 | 0.00 | 2.15 | 0.63 | 0.39 |
| Cosuppresion 3.1 | 0.06 | 7.57 | 0.50 | 3.83 | 32.24 | 20.00 | 15.66 | 2.06 | 15.65 | 0.34 | 1.85 | 0.23 | 0.90 |
| Cosuppresion 4.1 | 0.00 | 7.29 | 0.43 | 3.55 | 30.26 | 21.17 | 17.06 | 2.01 | 16.08 | 0.00 | 1.92 | 0.25 | 0.79 |
| Cosuppresion 4.2 | 0.08 | 8.02 | 0.53 | 3.62 | 33.04 | 20.04 | 15.68 | 1.80 | 14.72 | 0.00 | 1.88 | 0.58 | 0.92 |
| Cosuppresion 4.3 | 0.07 | 8.35 | 0.54 | 3.85 | 30.02 | 21.72 | 16.78 | 2.01 | 14.25 | 0.00 | 1.92 | 0.49 | 0.78 |
| Cosuppresion 4.4 | 0.06 | 6.98 | 0.53 | 3.62 | 43.38 | 13.24 | 12.77 | 1.74 | 15.37 | 0.30 | 1.67 | 0.33 | 1.67 |
| Cosuppresion 4.5 | 0.13 | 7.84 | 0.52 | 3.76 | 33.76 | 18.16 | 16.21 | 1.89 | 14.96 | 0.35 | 1.85 | 0.57 | 0.98 |
| Cosuppresion 4.6 | 0.11 | 8.18 | 0.32 | 3.58 | 19.72 | 29.19 | 20.26 | 2.04 | 13.92 | 0.29 | 1.84 | 0.55 | 0.40 |
| Cosuppresion 4.7 | 0.11 | 7.88 | 0.39 | 3.75 | 27.40 | 22.85 | 17.44 | 2.08 | 15.29 | 0.00 | 2.04 | 0.76 | 0.68 |
| Cosuppresion 4.8 | 0.13 | 7.56 | 0.41 | 3.46 | 32.27 | 20.50 | 15.45 | 1.90 | 15.47 | 0.00 | 2.02 | 0.83 | 0.90 |
| Cosuppresion 4.9 | 0.09 | 7.46 | 0.29 | 3.75 | 36.11 | 16.96 | 15.74 | 1.92 | 15.38 | 0.31 | 1.74 | 0.25 | 1.10 |
| Cosuppresion 5.1 | 0.10 | 7.68 | 0.34 | 3.88 | 36.00 | 16.77 | 15.38 | 1.90 | 15.44 | 0.32 | 1.82 | 0.36 | 1.12 |
| Cosuppresion 5.2 | 0.08 | 7.56 | 0.25 | 3.58 | 26.10 | 25.11 | 17.79 | 1.96 | 15.03 | 0.30 | 1.72 | 0.54 | 0.61 |
| Cosuppresion 5.3 | 0.08 | 7.38 | 0.20 | 3.56 | 42.24 | 13.33 | 13.32 | 1.76 | 15.19 | 0.16 | 1.61 | 1.18 | 1.59 |
| Cosuppresion 6.1 | 0.08 | 8.04 | 0.50 | 3.68 | 31.37 | 20.29 | 17.17 | 1.84 | 14.31 | 0.00 | 1.76 | 0.95 | 0.84 |
| Cosuppresion 6.2 | 0.00 | 8.50 | 0.51 | 3.91 | 18.59 | 29.33 | 19.66 | 2.46 | 14.75 | 0.00 | 2.28 | 0.00 | 0.38 |
| Control c24 pGNAP-p450 | 0.07 | 8.30 | 0.10 | 4.78 | 19.68 | 25.91 | 20.56 | 2.97 | 15.29 | 0.31 | 1.79 | 0.24 | 0.42 |

Analysis of the results indicates that transgenic plants harboring a CoP construct (indicated as "hairpin x.x" in the table) have a higher frequency of plants with oil wherein the increase in oleic acid and concomitant decrease in linolenic and linoleic acid is significant than in transgenic plants harboring cosuppression constructs. Moreover the absolute levels of increase, respectively decrease are higher respectively lower than in transgenic plants harboring cosuppression constructs.

Example 7

Modifying Oil Profile Using CoP Constructs in *Brassica*

The T-DNA vector harboring the chimeric gene encoding the CoP construct described in Example 6 is introduced in *Brassica* oilseed rape. Seeds harvested from the transgenic *Brassica* sp. are crashed and oil extracted and the composition of the fatty acids in the oil is analyzed.

Oil from transgenic *Brassica* sp. harboring the CoP construct have significantly increased oleic acid content and decreased linoleic and linolenic acid content. A T-DNA vector harboring a chimeric gene encoding a CoP construct similar to the one described in Example 6, but wherein the sequence of the sense and antisense region corresponding to the Δ12 desaturase encoding ORF is based on a homologous ORF from *Brassica* spp. is constructed and introduced in *Brassica* oilseed rape.

The sequence of *Brassica* spp ORFs homologous to Δ12 desaturase encoding ORF from *Arabidopsis* are available from Genbank database under Accession nrs AF042841 and AF124360.

Seeds harvested from the transgenic *Brassica* sp. are crashed and oil extracted and the composition of the fatty acids in the oil is analyzed. Oil from transgenic *Brassica* sp. harbouring the CoP construct have significantly increased oleic acid content and decreased linoleic and linolenic acid content.

Example 8

Suppression of an Endogenous Rust Resistance Gene in Flax

A CoP construct for suppression of the endogenous rust resistance gene was made consisting of
1. a CaMV35S promoter; operably linked to
2. part of an endogenous rust resistance gene (n) from flax (about 1500 bp long) in the sense orientation; ligated to
3. a similar part of the endogenous rust resistance gene from flax (about 1450 bp long) in antisense orientation so that a perfect inverted repeat without spacer sequence is generated wherein each repeat is about 1450 bp long; followed by
4. a nos terminator.

Plain antisense constructs were made using a similar fragment as described sub 3 above inserted between a CaMV35S promoter and a nos terminator.

Flax plants containing the n gene (which gives resistance to a strain of flax rust) were transformed by these CoP and antisense constructs. If suppression occurs, the plants become susceptible to the rust strain. If the construct has no effect, the transformed plants remain resistant to the rust strain.

Results

| | |
|---|---|
| ngc-b sense/antisense | 3 suppressed out of 7 |
| ngc-b antisense | 0 suppressed out of 12 |

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

REFERENCES

An et al. (1996) *The Plant Cell* 8, 15-30
Barry et al. (1993) *Proc Natl Acad Sci* 90, 4557-4561
Baulcombe (1996) *Plant Cell* 8, 1833-1844
Braun and Hemenway (1992) *Plant Cell* 4, 735-744
Brederode et al. (1995) *Virology* 207, 467-474
Carr et al. (1992) *Mol. Plant-Microb. Interact.* 5, 397-404
Christensen and Quail (1996) *Transgenic Research* 5, 213-218
Croy Plant Molecular Biology Labfax (1993) BIOS Scientific Publications Ltd (UK) and Blackwell Scientific Publications, UK.
de Carvalho Niebel et al. (1995) *Plant Cell* 7, 347-358
English et al. (1996) *Plant Cell* 8, 179-188
Fire et al. (1998) *Nature* 391, 806-811
Fromm et al. (1990) *Bio/Technology* 8: 833
Gleave, (1992) *Plant Mol. Biol.* 20: 1203-1207
Goodwin et al. (1996) *Plant Cell* 8, 95-105
Gordon-Kamm et al. (1990) *The Plant Cell* 2: 603
Harpster et al. (1988) *Mol. Gen. Genet.* 212, 182-190
Hobbs et al. (1990) *Plant Mol. Biol.* 15, 851-864
Hudspeth et al. (1989) *Plant Mol Biol* 12: 579-589
Ingelbrecht et al. (1994) *Proc. Natl. Acad. Sci. USA* 91, 10502-10506
Jefferson et al. (1987) *EMBO J.* 6, 3901-3907
Kawchuck et al. (1991) *Molecular plant-microbe interactions* 4, 247-253.
Keil et al. (1989) *EMBO J.* 8: 1323-1330
Keller et al. (1988) *EMBO J.* 7: 3625-3633
Keller et al. (1989) *Genes Devel.* 3: 1639-1646
Landsman et al. (1988) *Mol Gen Genet* 214, 68-73
Lindbo & Dougherty (1992a) Mol. *Plant Micr. Int* 5, 144-153
Lindbo & Dougherty (1992b) *Virology* 189, 725-733
Lindbo et al. (1993) *Plant Cell* 5, 1749-1759
Longstaff et al., (1993) *EMBO J.* 12, 379-386
MacDonald et al. (1991) *Nucl. Acids Res.* 19, 5575-5581
Metzlaff et al. (1997) *Cell* 88, 845-854
Meyer et al. (1987) *Nature* 330: 677
Mueller et al. (1995) *Plant J.* 7, 1001-1003
Ohta et al. (1990) *Plant Cell. Physiol.* 31, 805-813
Pang et al. (1996) *Plant J.* 9, 899-909
Peleman et al. 1989 *Gene* 84: 359-369
Powell-Abel et al. (1986) *Science* 232, 738-743
Powell et al. (1990) *Virology* 175, 124-130
Que et al. (1998) *The Plant Journal* 13, 401-409
Sambrook et al. (1989) *Molecular Cloning: A Laboratory Manual*, Second Edition, Cold Spring Harbor Laboratory Press, NY
Sanford and Johnston, (1985) *J. Theor. Biol.* 113, 395-405
Schiebel et al. (1993a) *Journal of Biological Chemistry* 268: 11851-11857

Schiebel et al. (1993b) *Journal of Biological Chemistry* 268: 11858-11867
Smith et al. (1994) *Plant Cell* 6, 1441-1453
Stalberg et al., *Plant Molecular Biol.* 23, 671-683
Stam et al. (1997) *Ann. Botan.* 79, 3-12
Wagner and Sun (1998) *Nature* 391, 744-745
Wang et al. (1997) *Journal of Genetics and Breeding* 3
Wilbur and Lipmann (1983) *Proc. Nat. Acad. Sci. U.S.A.* 80: 726
Zheng et al., (1991) *Plant Physiol.* 97, 832-835
Zuker and Stiegler (1981) *Nucl. Acids Res.* 9, 133-148

What is claimed is:

1. A method for reducing the phenotypic expression of a nucleic acid of interest, which is normally capable of being expressed in a plant cell comprising the step of introducing into the plant cell a chimeric DNA comprising the following operably linked parts:
   a. a promoter operative in the plant cell;
   b. a DNA region, which when transcribed, yields an RNA comprising an RNA region capable of forming an artificial hairpin RNA structure comprising two annealing RNA sequences, wherein one of the annealing RNA sequences of the hairpin RNA structure comprises a sense sequence that is identical to at least 100 consecutive nucleotides of a nucleotide sequence of the nucleic acid of interest and wherein the second of said annealing RNA sequences comprises an antisense sequence which is identical to at least 100 consecutive nucleotides of the complement of at least part of the nucleotide sequence of the nucleic acid of interest and wherein the sense and antisense sequences of the artificial hairpin structure are not naturally occurring in one RNA molecule, or the sense and antisense sequences are separated by a spacer region which is heterologous with respect to the target gene; and
   c. a DNA region involved in transcription termination and polyadenylation.

2. The method of claim 1 in which the nucleic acid of interest is an endogenous gene of the plant cell.

3. The method of claim 1 in which the nucleic acid of interest is a gene integrated in the genome of the plant cell.

4. The method of claim 1 in which the nucleic acid of interest is a viral gene.

5. The method of claim 1 in which the cell is comprised within a plant.

6. The method of claim 1, wherein the RNA molecule comprises a spacer nucleotide sequence located between the sense and antisense nucleotide sequences.

7. The method of claim 1, wherein the chimeric DNA is stably integrated into the genome of the plant cell.

8. The method of claim 1, wherein the nucleic acid of interest is a gene belonging to a multigene family.

9. The method of claim 1, wherein the RNA molecule reduces expression of more than one nucleic acid of interest.

10. The method of claim 1, wherein the promoter is a tissue-specific promoter, organ-specific promoter, or seed-specific promoter.

11. The method of claim 1, wherein the phenotypic expression of the nucleic acid of interest is reduced by 75% in the plant cell in the presence of the chimeric gene relative to the absence of the chimeric gene.

12. A method to inhibit expression of a target gene in a plant cell comprising introduction of a ribonucleic acid (RNA) into the cell in an amount sufficient to inhibit expression of the target gene, wherein the RNA is a double stranded molecule with a first strand having a ribonucleotide sequence which corresponds to a nucleotide sequence of the target gene and a second strand having a ribonucleotide sequence which is complementary to the nucleotide sequence of the target gene, wherein the first and the second ribonucleotide strands are separate complementary strands that hybridize to each other to form said double-stranded molecule, and the double-stranded molecule inhibits expression of the target gene.

13. The method of claim 12 in which the target gene is a cellular gene.

14. The method of claim 12 in which the target gene is an endogenous gene.

15. The method of claim 12 in which the target gene is a transgene.

16. The method of claim 12 in which the target gene is a viral gene.

17. A method to inhibit expression of a target gene in a plant cell in vitro comprising introduction of a ribonucleic acid (RNA) into the cell in an amount sufficient to inhibit expression of the target gene, wherein the RNA is a double stranded molecule with a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide strands are separate complementary strands that hybridize to each other to form said double-stranded molecule, and the double-stranded molecule inhibits expression of the target gene.

18. The method of claim 17 in which the target gene is a cellular gene.

19. The method of claim 17 in which the target gene is an endogenous gene.

20. The method of claim 17 in which the target gene is a transgene.

21. The method of claim 17 in which the target gene is a viral gene.

22. A method for reducing the gene expression of a gene of interest in plant cells, said method comprising the step of introducing a first and second chimeric DNA, linked on one recombinant DNA such that both chimeric DNAs are integrated together in the nuclear genome of the transgenic plant cells; wherein said first chimeric DNA comprises the following operably linked parts:
  a) a plant-expressible promoter;
  b) a first DNA region capable of being transcribed into a sense RNA molecule with a nucleotide sequence comprising a sense nucleotide sequence of at least 10 consecutive nucleotides having 100% sequence identity with at least part of the nucleotide sequence of said gene of interest; and
c) a DNA region involved in transcription termination and polyadenylation functioning in plant cells; and wherein said second chimeric DNA comprises the following operably linked parts:
  a) a plant-expressible promoter;
  b) a second DNA region capable of being transcribed into an antisense RNA molecule with a nucleotide sequence comprising an antisense nucleotide sequence including at least 10 consecutive nucleotides, having 100% sequence identity with the complement of said at least 10 consecutive nucleotides of said sense nucleotide sequence; and optionally
  c) a DNA region involved in transcription termination and polyadenylation functioning in plant cells; wherein said sense and antisense RNA molecules are capable of forming a double stranded RNA by base-pairing between the regions which are complementary.

23. A method for obtaining a virus resistant plant, said method comprising the steps of
  1) providing the cells of said organism with a first and second chimeric DNA wherein said first chimeric DNA comprises the following operably linked parts:
    a) a promoter operative in said cells;
    b) a first DNA region capable of being transcribed into a sense RNA molecule with a nucleotide sequence comprising a sense nucleotide sequence of at least 10 consecutive nucleotides having 100% sequence identity with at least part of the nucleotide sequence of the genome of a virus, capable of infecting said organism; and optionally
    c) a DNA region involved in transcription termination and polyadenylation functioning in said cells;
  and wherein said second chimeric DNA comprises the following operably linked parts:
    a) a promoter operative in said cells;
    b) a second DNA region capable of being transcribed into an antisense RNA molecule with a nucleotide sequence comprising an antisense nucleotide sequence including at least 10 consecutive nucleotides, having 100% sequence identity with the complement of said at least 10 consecutive nucleotides of said sense nucleotide sequence; and optionally
    c) a DNA region involved in transcription termination and polyadenylation functioning in said cells; and wherein said sense and antisense RNA are capable of forming a double stranded RNA by base-pairing between the regions which are complementary.

24. The method of claim 23, wherein said cells of said plants are provided with said first and second chimeric DNA by crossing parent plants comprising either said first or said second chimeric DNA.

25. The method of claim 23, wherein said cells of said plants are provided with said first and second chimeric DNA by transforming a plant cell with said first and second chimeric DNA, and regenerating a plant from said transformed plant cell.

26. The method of claim 23, wherein said first and second chimeric DNA are integrated separately in said nuclear genome of said plant cell.

27. The method of claim 23, wherein said first and second chimeric DNA are linked on one recombinant DNA such that both chimeric DNAs are integrated together in the nuclear genome of the transgenic plant cells.

28. The method of claim 1 in which said sense sequence is identical to at least 150 consecutive nucleotides of a nucleotide sequence of the nucleic acid of interest and said antisense sequence is identical to at least 150 consecutive nucleotides of the complement of at least part of the nucleotide sequence of the nucleic acid of interest.

29. A method to inhibit expression of a target gene in a cell from a plant in vitro comprising synthesizing at least two ribonucleic acid (RNAs) in the cell in an amount sufficient to inhibit the expression of a target gene, wherein the at least two RNAs form a double-stranded structure containing separate complementary strands, wherein the first RNA consists essentially of a ribonucleotide sequence which corresponds to a nucleotide sequence of the target gene and the second RNA consists essentially of a ribonucleotide sequence which is complementary to the nucleotide sequence of the target gene, wherein the first and the second ribonucleotide sequences are complementary sequences that hybridize to each other to form said double-stranded structure, and wherein the target gene is an endogenous gene.

30. A method to inhibit expression of a target gene in a cell from a plant in vitro comprising synthesizing at least two ribonucleic acids (RNAs) in the cell in an amount sufficient to inhibit the expression of a target gene, wherein the at least two RNAs form a double-stranded structure containing separate complementary strands, wherein the first RNA consists essentially of a ribonucleotide sequence which corresponds to a nucleotide sequence of the target gene and the second RNA consists essentially of a ribonucleotide sequence which is complementary to the nucleotide sequence of the target gene, wherein the first and the second ribonucleotide sequences are complementary sequences that hybridize to each other to form said double-stranded structure, and wherein the target gene is a transgene.

31. A method to inhibit expression of a target gene in a cell from a plant in vitro comprising synthesizing at least two ribonucleic acids (RNAs) in the cell in an amount sufficient to inhibit the expression of a target gene, wherein the at least two RNAs form a double-stranded structure containing separate complementary strands, wherein the first RNA consists essentially of a ribonucleotide sequence which corresponds to a nucleotide sequence of the target gene and the second RNA consists essentially of a ribonucleotide sequence which is complementary to the nucleotide sequence of the target gene, wherein the first and the second ribonucleotide sequences are complementary sequences that hybridize to each other to form said double-stranded structure, and wherein the target gene is a viral gene.

32. A method to inhibit expression of a target gene in a cell from a plant comprising synthesizing at least two ribonucleic acid (RNAs) in the cell in an amount sufficient to inhibit the expression of a target gene, wherein the at least two RNAs form a double-stranded structure containing separate complementary strands, wherein the first RNA has a ribonucleotide sequence which corresponds to a nucleotide sequence of the target gene and the second RNA has a ribonucleotide sequence which is complementary to the nucleotide sequence of the target gene, wherein the first and the second ribonucleotide sequences are complementary sequences that hybridize to each other to form said double-stranded structure, and wherein the target gene is an endogenous gene.

33. A method to inhibit expression of a target gene in a cell from a plant comprising synthesizing at least two ribonucleic acids (RNAs) in the cell in an amount sufficient to inhibit the expression of a target gene, wherein the at least two RNAs form a double-stranded structure containing separate complementary strands, wherein the first RNA has a ribonucleotide sequence which corresponds to a nucleotide sequence of the target gene and the second RNA has a ribonucleotide sequence which is complementary to the nucleotide sequence of the target gene, wherein the first and the second ribonucleotide sequences are complementary sequences that hybridize to each other to form said double-stranded structure, and wherein the target gene is a transgene.

34. A method to inhibit expression of a target gene in a cell from a plant comprising synthesizing at least two ribonucleic acids (RNAs) in the cell in an amount sufficient to inhibit the expression of a target gene, wherein the at least two RNAs form a double-stranded structure containing separate complementary strands, wherein the first RNA has a ribonucleotide sequence which corresponds to a nucleotide sequence of the target gene and the second RNA has a ribonucleotide sequence which is complementary to the nucleotide sequence of the target gene, wherein the first and the second ribonucleotide sequences are complementary sequences that hybridize to each other to form said double-stranded structure, and wherein the target gene is a viral gene.

35. A method to inhibit expression of a target gene in a cell in a plant comprising contacting the cell with a construct encoding at least one ribonucleic acid (RNA) in an amount sufficient to inhibit the expression of a target gene, wherein the RNA comprises or forms a double-stranded structure containing a first ribonucleotide strand which corresponds to a nucleotide sequence of the target gene and a second ribonucleotide strand which is complementary to the nucleotide sequence of the target gene, wherein the first and the second ribonucleotide strands are separate complementary sequences that hybridize to each other to form said double-stranded structure, and the RNA comprising the double-stranded structure inhibits expression of the target gene.

36. The method of claim 35, wherein said plant is selected from the group consisting of monocots, dicots and gymnosperms.

37. The method of claim 35, wherein said plant is selected from the group consisting of *Arabidopsis*, field crops, vegetable crops, fruit crops, nut crops and ornamentals.

38. The method of claim 35, wherein said cell is transfected with said construct.

39. The method of claim 35, wherein said cell is transformed with said construct.

40. The method of claim 35, wherein said construct is an expression construct.

41. The method of claim 38 wherein said construct is introduced into said target cell by a method selected from the group consisting of particle bombardment, electroporation, lipid-mediated carrier transport and chemical-mediated transport.

42. The method of claim 38 wherein said target cell is at risk for infection by a pathogen.

43. The method of claim 36 wherein inhibition of expression of said target gene provides a plant with altered fruit ripening characteristics.

44. The method of claim 39 wherein said RNA is synthesized in said cell in response to a condition selected from the group consisting of infection, stress, temperature and chemical induction.

45. The method of claim 42, wherein said infection is caused by a pathogen selected from the group consisting of arachnids, insects, nematodes, protozoans, bacteria and fungi.

46. The method of claim 39 wherein said RNA is synthesized in said cell at a specific development stage or age.

47. The method of claim 39 wherein said RNA is synthesized in said plant in a tissue-specific manner.

48. The method of claim 47, wherein said tissue is selected from the group consisting of fruit seed, anther, flower, leaf and root.

49. A method to reduce the phenotypic expression of a nucleic acid of interest in a plant cell comprising introducing into the plant cell a construct encoding at least one ribonucleic acid (RNA), wherein the RNA comprises or forms a double-stranded structure containing a first strand comprising a ribonucleotide sequence which is essentially similar to a nucleotide sequence of the target gene and a second strand comprising a ribonucleotide sequence which is essentially similar to a nucleotide sequence which is complementary to the nucleotide sequence of the target gene, wherein the first and the second ribonucleotide sequences are separate complementary sequences that base-pair to each other to form said double-stranded structure, and the RNA comprising the double-stranded structure reduces the phenotypic expression of the target gene.

50. The method of claim 49, wherein said plant is selected from the group consisting of monocotyledonous and dicotyledonous plants.

51. The method of claim 49, wherein said plant is selected from the group consisting of *Arabidopsis*, crop plants including corn, rice, wheat, barley, sugarcane, cotton, oilseed rape, soybean, vegetables (including chicory, brassica vegetables, lettuce, tomato), tobacco, potato, sugarbeet, plants used in horticulture, floriculture or forestry, oilseed rape (*Brassica juncea, napus, rapa, oleracea, campestris*), corn, cotton, groundnut, sunflower, castor beans, flax, coconut, linseed, soybean and plants important in viticulture or in fruit production.

52. The method of claim 49, wherein said construct is introduced transiently into said plant cell.

53. The method of claim 49, wherein said cell is transformed with said construct.

54. The method of claim 49, wherein said construct is an expression construct.

55. The method of claim 49 wherein said construct is introduced into said target cell by a method selected from the group consisting of direct gene transfer, microprojectile bombardment, lipid-mediated carrier transport and chemical-mediated transport.

56. The method of claim 49 wherein said plant cell is a plant cell at risk for infection by a pathogen.

57. The method of claim 49 wherein inhibition of expression of said target gene provides a plant with shatter resistance, modified flower color patterns, nematode resistance, delayed fruit ripening or male sterility.

58. The method of claim 53 wherein the expression of said RNA from said construct in said cell is controlled at will by the application of an appropriate chemical inducer, by operably linking the transcribed DNA region of the chimeric genes of the invention to a promoter whose expression is induced by a chemical compound.

59. The method of claim 56, wherein said infection is caused by a pathogen selected from the group consisting of viruses and nematodes.

60. The method of claim 53 wherein the expression of said RNA from said construct in said cell is under control of an organ-specific promoter.

61. The method of claim 53 the expression of said RNA from said construct in said cell is under control of a tissue-specific promoter.

62. The method of claim 61, wherein said tissue-specific promoter is selected from the group consisting of a seed-specific promoter, an organ-primordia specific promoter, a leaf specific promoter, a mesophyl-specific promoters, a root specific promoter, a tuber-specific promoter, a vascular tissue specific promoter, a stamen-selective promoter and a dehiscence zone specific promoters.

63. The method of claim 35 or claim 49, wherein said sense nucleotide sequence includes at least 20 consecutive nucleotides having between 95% and 100% sequence identity with at least 20 consecutive nucleotides of the nucleotide sequence of said nucleic acid of interest, and said antisense nucleotide sequence includes at least 20 consecutive nucleotides having between 95% and 100% sequence identity with the complement of said at least 20 consecutive nucleotides of said sense nucleotide sequence.

64. The method of claim 35 or claim 49, wherein said sense nucleotide sequence includes at least 50 consecutive nucleotides having between 95% and 100% sequence identity with at least 50 consecutive nucleotides of the nucleotide sequence of said nucleic acid of interest, and said antisense nucleotide sequence includes at least 50 consecutive nucleotides having between 95% and 100% sequence identity with the complement of said at least 50 consecutive nucleotides of said sense nucleotide sequence.

65. The method of claim 35, wherein said target gene is comprised in the genome of an infecting virus.

66. The method of claim 35, wherein said construct encodes said at least one RNA molecule under control of a constitutive plant-expressible promoter.

\* \* \* \* \*

SEQUENCE LISTING

```
<160> NUMBER OF SEQ ID NOS: 7

<210> SEQ ID NO 1
<211> LENGTH: 854
<212> TYPE: DNA
<213> ORGANISM: Potato virus Y
<220> FEATURE:
<223> OTHER INFORMATION: fragment of the NIa ORF

<400> SEQUENCE: 1
aagctttgaa gattgatttg atgccacata acccactcaa aatttgtgac aaaacaaatg      60
gcattgccaa atttcctgag agagagttcg agctaaggca gactgggcca gctgtagaag     120
tcgacgtgaa ggacatacca gcacaggagg tggaacatga agctaaatcg ctcatgagag     180
gcttgagaga cttcaaccca attgcccaaa cagtttgtag gctgaaagta tctgttgaat     240
atgggacatc agagatgtac ggttttggat ttggagcgta cataatagcg aaccaccatt     300
tgttcaggag ttataatggt tccatggagg tacgatccat gcacggtaca ttcagggtaa     360
agaatctaca cagtttgagc gttctgccaa ttaaaggtag ggacatcatc ctcattaaaa     420
tgccaaaaga tttccctgtc tttccacaga aattgcattt ccgagctcct acacagaacg     480
aaagaatttg tttagttgga accaactttc aggagaagta tgcatcgtcg atcatcacag     540
aagcaagcac tacttacaat ataccaggca gcacattctg gaagcattgg attgaaacag     600
ataatggaca ctgtggacta ccagtggtga gcactgccga tggatgtcta gtcggaattc     660
acagtttggc aaacaatgca cacaccacga actactactc agccttcgat gaagattttg     720
aaagcaagta cctccgaacc aatgagcaca tgaatgggt caagtcttgg atttataatc     780
cagacacagt gttgtgggc ccgttgaaac ttaaagacag cactcctaaa gggttattta     840
aaacaacaaa gctt                                                         854

<210> SEQ ID NO 2
<211> LENGTH: 2186
<212> TYPE: DNA
<213> ORGANISM: Artificial Sequence
<220> FEATURE:
<223> OTHER INFORMATION: Description of Artificial Sequence:coding
      region of the Gusd CoP construct
<220> FEATURE:
<221> NAME/KEY: misc_structure
<222> LOCATION: ()..()
<223> OTHER INFORMATION: deficient Gus coding region
<220> FEATURE:
<221> NAME/KEY: misc_feature
<222> LOCATION: ()..(2186)
<223> OTHER INFORMATION: antisense to the 5' end of the Gus coding
      region

<400> SEQUENCE: 2
atggtacgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
```

```
aatcaggaag tgatggagca tcagggcggc tatacgccat ttgaagccga tgtcacgccg    360
tatgttattg ccgggaaaag tgtacgtatc accgtttgtg tgaacaacga actgaactgg    420
cagactatcc cgccgggaat ggtgattacc gacgaaaacg gcaagaaaaa gcagtcttac    480
ttccatgatt tctttaacta tgccggaatc catcgcagcg taatgctcta caccacgccg    540
aacacctggg tggacgatat ctacccgctt cgcgtcggca tccggtcagt ggcagtgaag    600
ggcgaacagt tcctgattaa ccacaaaccg ttctacttta ctggctttgg tcgtcatgaa    660
gatgcggact tgcgtggcaa aggattcgat aacgtgctga tggtgcacga ccacgcatta    720
atggactgga ttggggccaa ctcctaccgt acctcgcatt acccttacgc tgaagagatg    780
ctcgactggg cagatgaaca tggcatcgtg gtgattgatg aaactgctgc tgtcggcttt    840
aacctctctt taggcattgg tttcgaagcg ggcaacaagc cgaaagaact gtacagcgaa    900
gaggcagtca acgggaaaac tcagcaagcg cacttacagg cgattaaaga gctgatagcg    960
cgtgacaaaa accacccaag cgtggtgatg tggagtattg ccaacgaacc ggatacccgt   1020
ccgcaaggtg cacgggaata tttcgcgcca ctggcggaag caacgcgtaa actcgacccg   1080
acgcgtccga tcacctgcgt caatgtaatg ttctgcgacg ctcacaccga taccatcagc   1140
gatctctttg atgtgctgtg cctgaaccgt tattacggat ggtatgtcca aagcggcgat   1200
ttggaaacgg cagagaaggt actggaaaaa gaacttctgg cctggcagga gaaactgcat   1260
cagccgatta tcatcaccga atacggcgtg gatacgttag ccgggctgca ctcaatgtac   1320
accgacatgt ggagtgaaga gtatcagtgt gcatggctgg atatgtatca ccgcgtcttt   1380
gatcgcgtca gcgccgtcgt cggtgaacag gtatggaatt cgccgatttt tgcgacctcg   1440
caaggcatat tgcgcgttgg cggtaacaag aaagggatct tcactcgcga ccgcaaaccg   1500
aagtcggcgg cttttctgct gcaaaaacgc tggactggca tgaacttcgg tgaaaaaccg   1560
cagcagggag gcaaacaatg aaacagacgc gtggttacag tcttgcgcga catgcgtcac   1620
cacggtgata tcgtccaccc aggtgttcgg cgtggtgtag agcatacgct gcgatggatt   1680
ccggcatagt taaagaaatc atggaagtaa gactgctttt tcttgccgtt ttcgtcggta   1740
atcaccattc ccgcgggat agtctgccag ttcagttcgt tgttcacaca aacggtgata   1800
cgtacacttt tcccggcaat aacatacggc gtgacatcgg cttcaaatgg cgtatagccg   1860
ccctgatgct ccatcacttc ctgattattg acccacactt tgccgtaatg agtgaccgca   1920
tcgaaacgca gcacgatacg ctggcctgcc aaccttcg gtataaagac ttcgcgctga   1980
taccagacgt tgcccgcata attacgaata tctgcatcgg cgaactgatc gttaaaactg   2040
cctggcacag caattgcccg gctttcttgt aacgcgcttt cccaccaacg ctgatcaatt   2100
ccacagtttt cgcgatccag actgaatgcc cacaggccgt cgagtttttt gatttcacgg   2160
gttggggttt ctacaggacg taccat                                        2186
```

<210> SEQ ID NO 3
<211> LENGTH: 208
<212> TYPE: DNA
<213> ORGANISM: Artificial Sequence
<220> FEATURE:
<223> OTHER INFORMATION: Description of Artificial Sequence:5'UTR of
      Johnson mosaic virus

<400> SEQUENCE: 3

```
cgccccgggc caacacaac acaacagaac ctacgtcaat tgattttatc aatcgcaaag      60
ccttacaaag atcttcgcag tcgttcatca acagattcac cgaaccattc ttgttagctc    120
```

| | |
|---|---|
| tcgcacagag ataagcagga aaccatggca ggtgagtgga acacagtttg atagtaagag | 180 |
| aaaccagagg aagactgcag gtacccgc | 208 |

<210> SEQ ID NO 4
<211> LENGTH: 1150
<212> TYPE: DNA
<213> ORGANISM: Artificial Sequence
<220> FEATURE:
<223> OTHER INFORMATION: Description of Artificial Sequence:Subterannean clover virus S4 promoter with S7 enhancer

<400> SEQUENCE: 4

| | |
|---|---|
| aatctgcagc ggccgcttaa tagtaattat gattaattat gagataagag ttgttattat | 60 |
| gcttatgagg aataaagaat gattaatatt gtttaattt attccgcgaa gcggtgtgtt | 120 |
| atgttttgt tggagacatc acgtgactct cacgtgatgt ctccgcgaca ggctggcacg | 180 |
| gggcttagta ttaccccgtg ccggatcaga gacatttgac taaatattga cttggaataa | 240 |
| tagcccttgg attagatgac acgtggacgc tcaggatctg tgatgctagt gaagcgctta | 300 |
| agctgaacga atctgacgga agagcggaca tacgcacatg gattatggcc cacatgtcta | 360 |
| aagtgtatct ctttacagct atattgatgt gacgtaagat gctttacttc gcttcgaagt | 420 |
| aaagtaggaa attgctcgct aagttattct tttctgaaag aaattattta attctaatta | 480 |
| aattaaatga gtcgctataa atagtgtcga tgctgcctca catcgtattc ttcttcgcat | 540 |
| cgtctgttct ggttttaagc gggatccagg cctcgagata tcggtaccctt gttattatca | 600 |
| ataaaagaat tttattgtt attgtgttat ttggtaattt atgcttataa gtaattctat | 660 |
| gattaattgt gaattattaa gactaatgag gataataatt gaatttgatt aaattaactc | 720 |
| tgcgaagcta tatgtctttc acgtgagagt cacgtgatgt ctccgcgaca ggctggcacg | 780 |
| gggcttagta ttaccccgtg ccgggatcag agacatttga ctaaatgttg acttggaata | 840 |
| atagcccttg gattagatga cacgtggacg ctcaggatct gtgatgctag tgaagcgctt | 900 |
| aagctgaacg aatctgacgg aagagcggac aaacgcacat ggactatggc ccactgcttt | 960 |
| attaaagaag tgaatgacag ctgtctttgc ttcaagacga agtaaagaat agtggaaaac | 1020 |
| gcgtaaagaa taagcgtact cagtacgctt cgtggcttta tataaatagt gcttcgtctt | 1080 |
| attcttcgtt gtatcatcaa cgaagaagtt aagctttgtt ctgcgttta atgatcgatg | 1140 |
| gccagtcgac | 1150 |

<210> SEQ ID NO 5
<211> LENGTH: 1052
<212> TYPE: DNA
<213> ORGANISM: Artificial Sequence
<220> FEATURE:
<223> OTHER INFORMATION: Description of Artificial Sequence: subterranean clover virus promoter S4 with S4 enhancer

<400> SEQUENCE: 5

| | |
|---|---|
| ggatccaggc ctcgagatat cggtaccttg ttattatcaa taaaagaatt tttattgtta | 60 |
| ttgtgttatt tggtaattta tgcttataag taattctatg attaattgtg aattattaag | 120 |
| actaatgagg ataataattg aatttgatta aattaactct gcgaagctat atgtctttca | 180 |
| cgtgagagtc acgtgatgtc tccgcgacag gctggcacgg ggcttagtat taccccgtgc | 240 |
| cgggatcaga gacatttgac taaatgttga cttggaataa tagcccttgg attagatgac | 300 |
| acgtggacgc tcaggatctg tgatgctagt gaagcgctta agctgaacga atctgacgga | 360 |

| | |
|---|---|
| agagcggaca aacgcacatg gactatggcc cactgcttta ttaaagaagt gaatgacagc | 420 |
| tgtctttgct tcaagacgaa gtaaagaata gtggaaaacg cgtggatcca ggcctcgaga | 480 |
| tatcggtacc ttgttattat caataaaaga attttttattg ttattgtgtt atttggtaat | 540 |
| ttatgcttat aagtaattct atgattaatt gtgaattatt aagactaatg aggataataa | 600 |
| ttgaatttga ttaaattaac tctgcgaagc tatatgtctt tcacgtgaga gtcacgtgat | 660 |
| gtctccgcga caggctggca cggggcttag tattacccg tgccgggatc agagacattt | 720 |
| gactaaatgt tgacttggaa taatagccct tggattagat gacacgtgga cgctcaggat | 780 |
| ctgtgatgct agtgaagcgc ttaagctgaa cgaatctgac ggaagagcgg acaaacgcac | 840 |
| atggactatg gcccactgct ttattaaaga agtgaatgac agctgtcttt gcttcaagac | 900 |
| gaagtaaaga atagtggaaa acgcgtaaag aataagcgta ctcagtacgc ttcgtggctt | 960 |
| tatataaata gtgcttcgtc ttattcttcg ttgtatcatc aacgaagaag ttaagctttg | 1020 |
| ttctgcgttt taatgatcga tggccagtcg ac | 1052 |

<210> SEQ ID NO 6
<211> LENGTH: 1583
<212> TYPE: DNA
<213> ORGANISM: Artificial Sequence
<220> FEATURE:
<223> OTHER INFORMATION: Description of Artificial Sequence: coding
      sequence of the desaturase CoP construct
<220> FEATURE:
<221> NAME/KEY: misc_feature
<222> LOCATION: (1)..(480)
<223> OTHER INFORMATION: corresponding to the 5' end of the
      delta12-desaturase (fad2) coding region, in sense
      orientation
<220> FEATURE:
<221> NAME/KEY: misc_feature
<222> LOCATION: (1101)..(1583)
<223> OTHER INFORMATION: corresponding to the 5' end of the
      delta12-desaturase (fad2) coding region, in anti
      sense orientation

<400> SEQUENCE: 6

| | |
|---|---|
| atcattatag cctcatgctt ctactacgtc gccaccaatt acttctctct cctccctcag | 60 |
| cctctctctt acttggcttg gccactctat tgggcctgtc aaggctgtgt cctaactggt | 120 |
| atctgggtca tagcccacga atgcggtcac cacgcattca gcgactacca atggctggat | 180 |
| gacacagttg gtcttatctt ccattccttc ctcctcgtcc cttacttctc ctggaagtat | 240 |
| agtcatcgcc gtcaccattc caacactgga tccctcgaaa gagatgaagt atttgtccca | 300 |
| aagcagaaat cagcaatcaa gtggtacggg aaatacctca caacccctct ggacgcatc | 360 |
| atgatgttaa ccgtccagtt tgtcctcggg tggcccttgt acttagcctt taacgtctct | 420 |
| ggcagaccgt atgacgggtt cgcttgccat ttcttcccca acgctcccat ctacaatgac | 480 |
| cgagaacgcc tccagatata cctctctgat gcgggtattc tagccgtctg ttttggtctt | 540 |
| taccgttacg ctgctgcaca agggatggcc tcgatgatct gcctctacgg agtaccgctt | 600 |
| ctgatagtga atgcgttcct cgtcttgatc acttacttgc agcacactca tccctcgttg | 660 |
| cctcactacg attcatcaga gtgggactgg ctcaggggag cttttggctac cgtagacaga | 720 |
| gactacggaa tcttgaacaa ggtgttccac aacattacag acacacacgt ggctcatcac | 780 |
| ctgttctcga caatgccgca ttataacgca atggaagcta caaaggcgat aaagccaatt | 840 |
| ctgggagact attaccagtt cgatggaaca ccgtggtatg tagcgatgta tagggaggca | 900 |
| aaggagtgta tctatgtaga accggacagg gaaggtgaca agaaaggtgt gtactggtac | 960 |

```
aacaataagt tatgagcatg atggtgaaga aattgtcgac ctttctcttg tctgtttgtc    1020
ttttgttaaa gaagctatgc ttcgttttaa taatcttatt gtccattttg ttgtgttatg    1080
acattttggc tgctcattat gttcagtaac atctaccctc gcaacccctt ctttaccgtt    1140
cgcttgggca gtatgccaga cggtctctgc aatttccgat tcatgttccc ggtgggctcc    1200
tgtttgacct gccaattgta gtactacgca ggttctccca acaactccat aaagggcatg    1260
gtgaactaac gactaaagac gaaaccctgt ttatgaagta gagaaagctc cctaggtcac    1320
aaccttacca ctgccgctac tgatatgaag gtcctcttca ttccctgctc ctccttcctt    1380
accttctatt ctggttgaca cagtaggtcg gtaaccatca gcgacttacg caccactggc    1440
gtaagcaccc gatactgggt ctatggtcaa tcctgtgtcg gaactgtccg ggttatctca    1500
ccggttcggt tcattctctc tccgactccc tcctctctct tcattaacca ccgctgcatc    1560
atcttcgtac tccgatatta cta                                            1583

<210> SEQ ID NO 7
<211> LENGTH: 786
<212> TYPE: DNA
<213> ORGANISM: Artificial Sequence
<220> FEATURE:
<223> OTHER INFORMATION: Description of Artificial Sequence:  intron 2
      of the Flaveria trinervia puryvate orthophosphate dikinase

<400> SEQUENCE: 7
aagcttggta aggaaataat tattttcttt tttccttta gtataaaata gttaagtgat       60
gttaattagt atgattataa taatatagtt gttataattg tgaaaaaata atttataaat     120
atattgttta cataaacaac atagtaatgt aaaaaaatat gacaagtgat gtgtaagacg     180
aagaagataa aagttgagag taagtatatt attttttaatg aatttgatcg aacatgtaag    240
atgatatact agcattaata tttgttttaa tcataatagt aattctagct ggtttgatga     300
attaaatatc aatgataaaa tactatagta aaaataagaa taaataaatt aaaataatat     360
ttttttatga ttaatagttt attatataat taaatatcta taccattact aaatatttta    420
gtttaaaagt taataaatat tttgttagaa attccaatct gcttgtaatt tatcaataaa    480
caaaatatta aataacaagc taaagtaaca ataatatca aactaataga aacagtaatc     540
taatgtaaca aaacataatc taatgctaat ataacaaagc gcaagatcta tcattttata    600
tagtattatt ttcaatcaac attcttatta atttctaaat aatacttgta gttttattaa    660
cttctaaatg gattgactat taattaaatg aattagtcga acatgaataa acaaggtaac    720
atgatagatc atgtcattgt gttatcattg atcttacatt tggattgatt acagttggga    780
aagctt                                                                786
```